United States Patent [19]
Jalkanen et al.

[11] Patent Number: 6,017,727
[45] Date of Patent: *Jan. 25, 2000

[54] SYNDECAN ENHANCER ELEMENT AND SYNDECAN STIMULATION OF CELLULAR DIFFERENTIATION

[75] Inventors: Markku Jalkanen, Piispanristi; Panu Jaakkola; Tapani Vihinen, both of Turku, all of Finland

[73] Assignee: BioTie Therapies Ltd., Turku, Finland

[*] Notice: This patent is subject to a terminal disclaimer.

[21] Appl. No.: 08/760,534

[22] Filed: Dec. 2, 1996

Related U.S. Application Data

[63] Continuation-in-part of application No. 08/206,186, Mar. 7, 1994, abandoned, which is a continuation-in-part of application No. PCT/FI93/00514, Dec. 1, 1993.

[51] Int. Cl.[7] .......................... C12N 15/67; C12N 15/10; C12N 5/10; C12N 15/64
[52] U.S. Cl. ................... 435/69.1; 536/24.1; 536/22.1; 435/325; 435/320.1
[58] Field of Search ................. 536/24.1, 22.1; 435/69.1, 325, 320.1

[56] References Cited

U.S. PATENT DOCUMENTS 5,726,058  3/1998  Jalkanen et al. .................. 435/354

FOREIGN PATENT DOCUMENTS

| | | |
|---|---|---|
| 0 335 554 | 10/1989 | European Pat. Off. . |
| 0 455 422 | 11/1991 | European Pat. Off. . |
| 0 462 398 | 12/1991 | European Pat. Off. . |
| WO 90/12033 | 10/1990 | WIPO . |
| WO 92/13274 | 8/1992 | WIPO . |
| WO 93/05167 | 3/1993 | WIPO . |
| 94/12162 | 6/1994 | WIPO . |

OTHER PUBLICATIONS

Deutsch et al. Proc. Natl. Acad. Sci. USA 85, 7922–7926, 1988.

Vihinen et al., Structural organization and genomic sequence of mouse syndican–1 gene, J. Biol. Chem., 268(23):17261–17269, Aug. 1993.

Couchman, J. et al., "Changes in Microfilament And Focal Adhesion Distribution with Loss of Androgen Responsiveness in Cultured Mammary Tumor Cells," *Cancer Res.* 41:263–269 (1981).

Ekblom, P. et al., "Cell–Matrix Interactions and Cell Adhesion During Development," *Ann. Rev. Cell Biol.* 2:27–47 (1986).

Elenius, K. et al., "Binding of Human Syndecan to Extracellular Matrix Proteins," *J. Biol. Chem.* 265(29):17837–17843 (1990).

Elenius, K. et al., "Growth Factors Induce 3T3 Cells to Express bFGF–binding Syndecan," *J. Biol. Chem.* 267(9):6435–6441 (Mar. 1992).

Elenius, K. et al., "Induced Expression of Syndecan in Healing Wounds," *J. Cell Biol.* 114(3):585–595 (Aug. 1991).

(List continued on next page.)

*Primary Examiner*—Lila Feisee
*Assistant Examiner*—Claire M. Kaufman
*Attorney, Agent, or Firm*—Sterne, Kessler, Goldstein & Fox P.L.L.C.

[57] ABSTRACT

A DNA enhancer element and the use of this syndecan enhancer element to regulate the expression of genes are provided.

46 Claims, 47 Drawing Sheets

OTHER PUBLICATIONS

Inki, P. et al., "Immunohistochemical Localization of Syndecan in Mouse Skin Tumors Induced by UV Irradiation," *Amer. J. Pathology* 139(6):1333–1340 (Dec. 1991).

Inki, P. et al., "Syndecan in Carcinomas Produced from Transformed Epithelial Cells in Nude Mice," *Lab. Invest.* 66(3):314–323 (Mar. 1992).

Jalkanen, M. et al., "Binding of Extracellular Effector Molecules by Cell Surface Proteoglycans," in: *Receptors for Extracellular Matrix*, McDonald, J.S and Mecham, R.P., Eds., Academic Press, Inc., Pub., San Diego, CA; pp. 1–37 (Nov. 1991).

Jalkanen, M., "Biology of Cell Surface Heparan Sulfate Proteoglycans," *Medical Biology* 65:41–47 (1987).

Jalkanen, M. et al., "Cell Surface Proteoglycan of Mouse Mammary Epithelial Cells Is Shed by Cleavage of Its Matrix–binding Ectodomain from Its Membrane–associated Domain," *J. Cell Biol.* 105(6, pt. 2):3087–3096 (1987).

Jalkanen, M. et al., "Heparan Sulfate Proteoglycans from Mouse Mammary Epithelial Cells: Localization on the Cell Surface with a Monoclonal Antibody," *J. Cell Biol.* 101:976–984 (1985).

Jalkanen, M. et al., "Loss of Syndecan Expression in Mouse Mammary Epithelial Cells After Transformation With A Point–Mutated c–Ha–ras Proto–Oncogene," *J. Cell. Biochem. Suppl.* 13B:52, Abstract D317 (1989).

Jalkanen, M. et al., "Mouse Mammary Epithelial Cells Produce Basement Membrane And Cell Surface Heparan Sulfate Proteoglycans Containing Distinct Core Proteins,"*J. Cell Biol.* 106:953–962 (1988).

Jalkanen, M. et al., "Simultaneous Loss of Syndecan Expression and Epithelial Phenotype in S115 Carcinoma Cells Exposed to Steroids," *J. Cell Biochem. Suppl.* 14A:153, Abstract A113 (1990).

Jalkanen, M. et al., "Stimulation of syndecan gene expression in mesenchymal cells by bFGF and TGFβ," *J. Cell Biochem. Suppl.* 15F:223, Abstract CF115 (Oct. 1991).

Jalkanen, M. et al., "Syndecan, a regulator of cell behaviour, is lost in malignant transformation," *Biochem. Soc. Transactions* 19:1069–1072 (Nov. 1991).

Jalkanen, M. et al., "Syndecan Expression Is Suppressed In Steroid–Induced Transformation of Mouse Mammary Tumor Cell Line (S–115)," *J. Cell Biol.* 109:320a, Abstract No. 1758 (1989).

Kiefer, M. et al., "Ligand–affinity cloning and structure of a cell surface heparan sulfate proteoglycan that binds basic fibroblast growth factor," *Proc. Natl. Acad. Sci. USA* 87:6985–6989 (1990).

Leppä, S. et al., "Steroid–induced epithelial–fibroblastic conversion associated with syndecan suppression in S115 mouse mammary tumor cells," *Cell Regulation* 2:1–11 (Jan. 1991).

Leppä, S. et al., "Syndecan expression regulates cell morphology and growth of mouse mammary epithelial tumor cells," *Proc. Natl. Sci. Acad. USA* 89:932–936 (Feb. 1992).

Mali, M. et al., "Sequence of Human Syndecan Indicates a Novel Gene Family of Integral Membrane Proteoglycans," *J. Biol. Chem.* 265(12):6884–6889 (1990).

Rapraeger, A. et al., "Requirement of Heparan Sulfate for bFGF–Mediated Fibroblast Growth and Myoblast Differentiation," *Science* 252:1705–1708 (Jun. 1991).

Rapraeger, A. et al., "The Cell Surface Proteoglycan from Mouse Mammary Epithelial Cells Bears Chondroitin Sulfate and Heparan Sulfate Glycosaminoglycans," *J. Biol. Chem.* 260(20):11046–11052 (1985).

Rapraeger, A. et al., "Cell Surface Proteoglycan Associates with the Cytoskeleton at the Basolateral Cell Surface of Mouse Mammary Epithelial Cells," *J. Cell Biol.* 103(6, pt. 2):2683–2696 (1986).

Salmivirta, M. et al., "Syndecan from Embryonic Tooth Mesenchyme Binds Tenascin," *J. Biol. Chem.* 266(12):7733–7739 (Apr. 1991).

Salmivirta, M. et al., "Neurite Growth–Promoting Protein (Amphoterin, p30) Binds Syndecan," *Exp. Cell Res.* 200(2):444–451 (Jun. 1992).

Sanderson, R. et al., "Molecular polymorphism of a cell surface proteoglycan: Distinct structures on simple and stratified epithelia," *Proc. Natl. Sci. Acad. USA* 85:9562–9566 (1988).

Sanderson, R. et al., "B lymphocytes express and lose syndecan at specific stages of differentiation," *Cell Reg.* 1:27–35 (1989).

Saunders, S. et al., "Cell Surface Proteoglycan Binds Mouse Mammary Epithelial Cells to Fibronectin and Behaves as a Receptor for Interstitial Matrix," *J. Cell Biol.* 106:423–430 (1988).

Saunders, S. et al., "Mammary Epithelial Cells Transfected with Antisense cDNA Reduce Cell Surface Syndecan and Become Fibroblastic in Morphology," *J. Cell Biol.* 109:5a, Abstract No. 7 (1989).

Saunders, S. et al., "Molecular Cloning of Syndecan, an Integral Membrane Proteoglycan," *J. Cell Biol.* 108:1547–1556 (1989).

Thesleff, I. et al., "Cell Surface Proteoglycan Expression Correlates with Epithelial–Mesenchymal Interaction during Tooth Morphogenesis," *Dev. Biol.* 129:565–572 (1988).

Vaahtokari, A. et al., "Associations between transforming growth factor β1 RNA expression and epithelial–mesenchymal interactions during tooth morphogenesis," *Development* 113:985–994 (Nov. 1991).

Vainio, S. et al., "Epithelial–Mesenchymal Interactions Regulate the Stage–Specific Expression of a Cell Surface Proteoglycan, Syndecan, in the Developing Kidney," *Dev. Biol.* 134:382–391 (1989).

Vainio, S. et al., "Expression of Syndecan Gene is Induced Early, Is Transient, and Correlates with Changes in Mesenchymal Cell Proliferation during Tooth Organogenesis," *Dev. Biol.* 147:322–333 (Oct. 1991).

Vainio, S. et al., "Syndecan and Tenascin Expression Is Induced by Epithelial–Mesenchymal Interactions in Embryonic Tooth Mesenchyme," *J. Cell Biol.* 108:1945–1954 (1989).

Wilkinson, D. et al., "Expression pattern of the FGF–related proto–oncogene int–2 suggests multiple roles in fetal development," *Development* 105:131–136 (1989).

Yates, J. et al., "Correlation of Growth Properties and Morphology with Hormone Responsiveness of Mammary Tumor Cells in Culture," *Cancer Res.* 41:258–262 (1981).

Yayon, A. et al., "Cell Surface, Heparin–like Molecules Are Required for Binding of Basic Fibroblast Growth Factor to Its High Affinity Receptor," *Cell* 64:841–848 (Feb. 1991).

Arbeit, J.M. et al., "Upregulation of fibroblast growth factors and their receptors during multi–stage epidermal carcinogenesis in K14–HPV16 transgenic mice," *Oncogene* 13(9):1847–1857 (Nov. 1996).

Baiocchi, G. et al., "Expression of the Macrophage Colony–Stimulating Factor and Its Receptor in Gynecologic Malignancies," *Cancer* 67(4):990–996 (Feb. 1991).

Bennett, N.T. and Schulz, G.S., "Growth Factors and Wound Healing: Biochemical Properties of Growth Factors and Their Receptors," *Am. J. Surg.* 165(6):728–737 (Jun. 1993).

Gregor, P.D. et al., "The adenovirus major late transcription factor USF is a member of the helix–loop–helix group of regulatory proteins and binds to DNA as a dimer," *Genes Dev.* 4(10):1730–1740 (1990).

Heath, J.K. and Valancius–Mangel, V., "Embryonic growth factors," *Curr. Opin. Cell Biol.* 3(6):935–938 (Dec. 1991).

"Hormones and Related Agents," in: Goodman and Gilman's *The Pharmacological Basis of Therapeutics, Eighth Edition*, Pergamon Press, Pub., New York, NY; pp. 1256–1257 (Sep. 1990).

Inki, P. et al., "Expression of Syndecan in Transformed Mouse Keratinocytes," *Lab. Inves.* 62(2):225–233 (Aug. 1992).

Jaakkola, P., "Activation of an Enhancer on the Syndecan–1 Gene Is Restricted to Fibroblast Growth Factor Family Members in Mesenchymal Cells," *Mol. Cell. Biol.* 17(6):3210–3219 (Jun. 1997).

Jain, R.K., "Barriers to Drug Delivery in Solid Tumors," *Sci. Am.* 271(1):58–65 (Jul. 1994).

Janet, T. et al., "Mitogenic Growth Factors Regulate Differentially Early Gene mRNA Expression: A Study on Two Clones of 3T3 Fibroblasts," *Exp. Cell Res.* 198(2):305–314 (Feb. 1992).

Karin, M., "Signal transduction from the cell surface to the nucleus through the phosphorylation of transcription factors," *Curr. Opin. Cell Biol.* 6(3):415–424 (Jun. 1994).

Leask, A. et al., "Transcription factor AP2 and its role in epidermal–specific gene expression," *Proc. Natl. Acad. Sci. USA* 88(18):7948–7952 (Sep. 1991).

Marshall, G.M. et al., "Wounding Acts as a Tumor Promoter in Chickens Inoculated with Avian Sarcoma Virus 17," *Virology* 188(1):373–377 (May 1992).

Martin, P. and Nobes, C.D.,"An early molecular component of the wound healing response in rat embryos—induction of c–fos protein in cells at the epidermal wound margin," *Mechanisms Dev.* 38(3):209–215 (Sep. 1992).

Meier, P. et al., "Alternative mRNAs Encode Multiple Isoforms of Transcription Factor Ap–2 during Murine Embryogenesis," *Dev. Biol.* 169(1):1–14 (May 1995).

Miltenberger, R.J. et al., "An E–Box–Mediated Increase in cad Transcription at the G1/S–Phase Boundary Is Suppressed by Inhibitory c–Myc Mutants," *Mol. Cell. Biol.* 15(5):2527–2535 (May 1995).

Moser, M. et al., "Cloning and characterization of a second AP–2 transcription factor: AP–2β," *Development* 121(9):2779–2788 (Sep. 1995).

Saez, E. et al., "c–fos Is Required for Malignant Progression of Skin Tumors," *Cell* 82(5):721–732 (Sep. 1995).

Salmivirta, M. et al., "Basic Fibroblast Growth Factor–Syndecan Complex at Cell Surface or Immobilized to Matrix Promotes Cell Growth," *J. Biol. Chem.* 267(25):17606–17610 (Sep. 1992).

Sehgal, I. et al., "Transforming Growth Factor β1 Stimulates Contrasting Responses in Metastatic versus Primary Mouse Prostate Cancer–derived Cell Lines in Vitro," *Cancer Res.* 56(14):3359–3365 (Jul. 1996).

Vihinen, T. et al., "Functional Characterization of Mouse Syndecan–1 Promoter," *J. Biol. Chem.* 271(21):12532–12541 (May 1996).

Warren, R.S. et al., "Induction of Vascular Endothelial Growth Factor by Insulin–like Growth Factor 1 in Colorectal Carcinoma," *J. Biol. Chem.* 271(46):29483–29488 (Nov. 1996).

Werner, S. et al., "Large induction of keratinocyte growth factor expression in the dermis during wound healing," *Proc. Natl. Acad. Sci. USA* 89(15):6896–6900 (Aug. 1992).

Werner, S. et al., "The Function of KGF in Morphogenesis of Epithelium and Reepithelialization of Wounds," *Science* 266:819–822 (Nov. 1994).

Williams, T. and Tjian, R., "Characterization of a Dimerization Motif in AP–2 and its function in Heterologous DNA–Binding Proteins," *Science* 251:1067–1071 (Mar. 1991).

```
-4138                        tctagatattcaaactcac cagatgagtgatgtccacc cctattgtgggagtgacta
-4078 gtctttcctctgtcttctga ctcagatgcttagctagctc tttaggaccacctcacac  ctgcaaatatactttattt
-3998 gctctcttagtacctttaac ccagtggagttgacatgaga aattaactaccatatttat atatttcatttcataatg
-3918 aaagtaaaataaattaaaa  aatagaaaggtttgagcatg atgccagtggtaaaggcc  agtggctcaacgcaagtcc
-3838 tgacaaatgtaacgggcct  gttcttcaggcttgagggaa gtttattgattgagctaaa agcaaccaaaggctccact
-3758 tgcctagtgtgaagccctgg atgtgctctcccacactgca tgtccacctgtgtgtcagc acctgggaagctgaggatga
-3678 tggggagtccaagtcatta  gctacatagtataggctagc tggggtacatggtcacaaa aagaaaaaaataagcac
-3598 attgtaatccagcacttga  cagaccaatggggggggat  tgctgtgagtttaagacagc ctggcctacaagaaaaacc
-3518 ctacccaaaccaagaaaaa  tgaaaccagtaatataaata gctatttcatttaaatgc   tctaagacacagcgttaac
-3438 acaaaagctctcgtctgtgg ttcctattccctccttctcc cccagtctcttcttaatgta tactttttgtttgcttattt
-3358 gcttgtttttggattttggct tttaaagacaggtctcact  atgtagctccaactatttgg gaactcactatgtagaccag
-3278 gctagccaggacttataga  gatctacctaccactgcctc ccaagtgctgagactaaagg catgtgacctttgcttggt
-3198 tattacaaacatttaaaag  aacatttgaacattaatag  atgtatgtatatatcact  ctatgtagtatatgttag
-3118 acattttcactgagatac   atattactctcaaaataag  ttttttgttttttttctc  tttttaaattatttattt
-3038 tttttttatttattttatta ttatatgtaagtacactgta gctgtcttcagacanaccag aagagggagtcagatcttgt
-2958 tacggatggttgtgagcacc atgtggttgctgggattcga actctgggaccttccgaagag cagtcgggtgctcttaccca
-2878 ctgagccatctcaccagcc  cttaaattatttatctt    atgtccattggtgttttgcc tgcatgtatgtgtaaaagtg
-2798 tcagaaactgaagttacaga ctgttgtgagctaccattgt tgtgggtgctggacttgaa cctgggtcctctggaagagc
-2718 agtcattattcttaaccact gagccatctctctagccctc gtttttagtttttttttt  gttttgtttgttttttgtt
-2638 tttttaagatttttcttattt attatatgtaagtacactgt agctgtcttcagacactcca gaagagggcgccagatctcg
-2558 ttatggatggttgtgagcac catgtggttgctgggaattg aactccagacctttgaaga gcagtcagtgctcttaactg
-2478 ctgagccatctctccagccc cgtttttaggttttgaag   acagggtttcctgtgtagct ctagctgtccaggaactagc
-2398 tctgtagaccaggttgcct  caaattagagatttgcctg  tctctgcctctcgagagc  tgggattaaaagtgtgcagc
-2318 ccaacaatctactcaaagta ggttttgaaaaagctttcca tattaggagttaactagctt catttcagaaatactgcatg
-2238 gaattcaaatgtgggaccat tcatagctactttggttttc cttcagtgacaggcattcgg catgccttattagggaagtca
```

FIG.2a

```
-2158  aatggcctggagaagtcatc ctgggtgagaggctaatgc attttcagcttgacagacac tgtcaacctatgcagacagt
-2078  ctgctccagctcagatgtca attgcatgcagactgcagt cagacgctaagctccctacc tactctccatcagcttagat
-1998  gtaaggggtgctggaacaaa ggctctctctctctctctct ctctctctctctctctctct ttcttagaattagtattcta
-1918  ttttattttatgtaaattgg tacttcacttacatgtatgt ccgtgtgagatgttgtatc ctctgtactggagttatag
-1838  acagctgtaagtcgccatac agtgctgggaattgaaccc tgatcctgaagaatagt cagtgtcttaaccctgag
-1758  ccatctctccaacctcttgc atattgaggacaggaggaa tcacaagccatgtaggtgc ctgggctctgaggtcaacag
-1678  gaccatagcctcctttcttt atgtgcttttctggggtct ccctataggagtcgtcttcg ttgcctcttactgtctcat
-1598  tgatctgggctaaacttatg cagttgaaggaaagatcaa gctgttcatgtttaaaacat gaaacagcctcatcagttcc
-1518  cttcctgttccgtctcccc ccccctcccgcccccattt tgagaggacaggaaggtaaa ataccaaagtgtcctatttt
-1438  cctccaaatatcaggctcaa aggactgaagagctgacttc agatccaaagcccactgtgt taggaggcacctgcttttta
-1358  ggtcctaagccttcctgagc cttgctattgggtattcttt accaagaccctcaaggatct aggcaagaactgggcaggat
-1278  ctgtatgtagcccatagtta gacctagggcagctgagacg ccaaaaggagagtttcctg aggacaaaagtgttcaaaca
-1198  caactgggtgctggttgttg ggctactcgtggaggtgtgg tgtgtaaaggagggctgtt gaattcccagaaggctggtt
-1118  ccacagtgtagagtctacac tggggacttcccgagacgct gagcctcagatctagcttct cagtccaggccagctgatgt
-1038  gggctgaggaacaaggatg gatgccatctatggccctgc cttgcaggtgcaaagggcct ttggcaccatctacagattg
-958   agggcaagacagggctggtt cttcctccttgctctctcgctg ctatctgcctcgcctgtagg ctctctgggctcctttttgg
-878   actgacacgtctgaaggagc ttggaaactgtgaggtccag gcccatagagaatcatgaa ggaacaggaattcaactgga
-798   gctccgcagctgttaggcc tgcggtcacctggaaacaaa gaggccattatttttttcct ttggtcttgacaaggaaga
-718   gaagggctttctataaata gaaagacagcaaaaaagaa ataataataataataat aataataataataataaaa
-638   caataacaaagccagctctt ccagacagtgctcatgtctt taaaggtctttaaaggtctg gagttccagcaattaagta
-558   aaggaccaagacctcagggg tcccctatcctcagccctg gggaggtggaaccatacat cgatcctcggtttatatat
-478   agcctcatcgctgtgggct ccgaggttgccccaaaatc ttgctcacctggaggaccc tgggtgtcctcgcccagag
-398   gcgctgcagctcgcacgta gagaactaacatcgccttc tccagggcagtgcctccgga ctccgaccaggacatagta
-318   gcgagtgcacctggtctcc gtcagctacgcatcaaggaa ggtgcgacgcgggaattaca gattgccggcactcaccagt
-238   gctcaggggaggaagtggg actcagacctgcaagagctg aagagtgggtgggcttcga tcctaggagggcgtggaagg
```

FIG.2b

```
 -158 ggtgtggctggatccctggg gggtggggcgctccaaggggg cggggcaaccaggggggcgg ggcccgagggtggagattg
  -78 ggactaccccagcccgcgga gctgggggtgggcgctagt tttgcaactgcagagccttt gggtttattaaggcggAG
    3 CTCCGCGGAGAGGTGCGGG CCAGAGGAGACAGAGCCTAA CGCAGAGGAAGGACCTGGC AGTCGGGAGCTGACTCCAGC
   83 CGGGAAACCTACAGCCCTC GCTCGAGAGAGCAGGAGCT GGGCAGCAGAGCTGGACAGC AAAGGCAGAGCAATCAGCA
  163 GAGCCGGCCCGGAGCTCCGT GCAACCGGCCAACTCGGATCC ACGAAGCCCACCGAGCTCCC GCCGCCGGTCTGGGCAGCAT
                                                                                      Me
  243 GAGACGCGGCGGCTCTGGC TCTGGCTCTGCGCGCTGGCG CTGCGCCTGCAGCCTGCCCT CCCGgtgagtgtggcccggg
         tArgArgAlaAlaLeuTrpL euTrpLeuCysAlaLeuAla LeuArgLeuGlnProAlaLe uPro
  323 gcagggctgggaggcggcgg gaagccgggactcgccactc gccgatgccatgcaggcggc agcacgtggaggggagggg
  403 agcgggggactttctttcccgcg ctgcctggccggatcctgga tgtgagccctttaatgagg actcctgtcccaattcctct
  483 acggtccgtggatgccagga ggctatcccagctcgtgtc cgggcgtcctgcagagtgga acctccattggttcccgct
  563 cccattaagtaaaacgact ccacagggtctgagtcgcc ggcctaggcgctccgcgg ccttaggcgccgccttgagt
  643 tgctctctccgttgctgtc ttgctggccatctcagcggc ctgcctccgcagtgtccc ggaggatgcagtggccatgg
  723 ccaaacgcctttttccataga ccctaattcaaacagactg caggctgcaccccagcgcc gcggagtccgggcgctcggc
  803 cctttgcaccgggcaagtt tgggacacagaggggtggctc agggacttcggttttttctct cgttcggggtggcgggaggg
  883 acgggattaaggctgtttgt gggacacaagaggtggctc agggacttcggttttttctct ggctgcccagtgagccgg
  963 gccgagctgcagcgggagg ttccggaagttggcttcag aacgctgaagacccccgga cccaacttgggtggtcgctga
 1043 agttgtgctgccccccgagg gcctcctccgcatgccccgc gcggggaccctccccgca gtgacccgtacggctct
 1123 tcccctccccgactcggct ttgtgctgaagccgcgcgta gggaaggcgggtccccttggc ccgccagtagggccggg
 1203 gaaagagggacgaacgtgga gctggcgactggtgggggaa gcttctgggtaggatgcagc catccaccctttggtgggtc
 1283 ggtctctctaatcagcggct tggcgacaaagagcttggtc gaggtaccccagaaagtgc tctcccgcccaagccgcg
 1363 tcgctagccgccttcccaa cgggcgctttgttcctcgcc cctgtaacccctccctggga accgccccgcagcgctggtc
 1443 cttgacgtgggccgggtcct gggtcgccgccagtgtcagc gctgccctccgtgtccacg ccctagccccgcacccgc
 1523 tgtgaagtcccggtgtcct ttccactggcgctttgccca acccctgaaggcagagggcg aggtgcggagcctcaggctt
```

FIG.2c

```
1603 tatcctcccggaagtggcag tctcccaccgccacatctgg tctgcttaacttcgatagtc ctggcaaaggcagacacgtg
1683 cacagggaaggagagttgag cgctggtagataccaagtc gtgtacaaataaagtggcac acgacacgtccccagtcact
1763 gttaatgcattgcttcgct ccttcccagtggctggtgc tctccatcactctggagccc aagagagggcctccataatt
1843 gtattgccatgagttgggg ttgtgtgggggcgccaaatc agggttctctggagggcta tgaattcgaactgagtctc
1923 ctgtgcactcctggctttaa ggttcaagaaattgtttgag ggttgtgtttttgtgggac tcagattatgcctggaatca
2003 tagttaccactgtggagaag aaagtggagctacttagcat gcctcccgcccgcctggc attacctccggctctgttct
2083 ctaggcccaacgtgaggcct cactggggcagtacagatgc agtactgaatttctttccag ccaggatctggagaggtggt
2163 gtctcttcctgtgtctt tagagaggcagatattcctg tgacctaagccctcaagca cccattaataatgctgagta
2243 gacaactagaggtggcgttt tccggaacttcctgtgtgct ggcctggagttgaaccct ctaggaaacaggtctaggaa
2323 gtagaattatctcaatgaaa ggcttcctggagaagaaga tgagctgagccccagtca ctgtctgagctttaggatca
2403 gactcccacttggaggcaag agtgttcgttttactttttt tttttaagtttagtttattt tctctctaacagaaaacaaa
2483 caaacaaacaaaaaaaacc ccacattgtttaaaagtggg tgcataagagtgaggacata ttcagagcttcccctttcc
2563 tgaaaaatgaaggcagctgg gatttacttaaaatgagagc acatatcacaattgccagag agctggtccctttctcagg
2643 ctccctaagctcctgtggga agcaggtcagacagcctg ggaccagagagataggagt gcttttggtgctgcctt
2723 gaatggggaagggggggga gctgctgggatcagaggctg ctagcaactactctcccagag actgaagcaggtttgtcct
2803 cagtgtcctgtgtgtcttctg tttctcctatatagaatagg agaaatggttatttgtctg gaatagtgacttgctatttg
2883 ttccctttctttcctctcc ttactgtaatcatttggact agtagagacactttcccag gtctggcagaatgggagga
2963 gtggggaggcctgtgcttg catgatgtcactgctgctt cagctctccaggaggtgg agttggttgtaacctacctg
3043 tggctcttgatgggccacaa taaaacctcattaacacaca ttggtagggagaagggactg gaaagaatgatggaaagat
3123 tgatgtttttcctttttttt tttttttttttggcagta ctttctagatctccctcc ccttgctgcagcaaaattt
3203 ggattcctgaagtcctttga gaatgtataatgtagccag actttttttttcagtcag ctcaaaattgcctcctata
3283 aagtatccttgttgtttt tgttgttgttgttgttg ttttgttttgttttaagaca agtttctctgtatagtcct
3363 ggctgccctgaactcaata tgtagaccaggctggcctca aactcaagaaatccacta cttctaacttcagtgctgg
3443 gcctaaagtgtaggccacc aaaagtgctcaactttaca aagcagtcttacttgagca ggattctgaaccctattt
```

FIG.2d

```
3523  cctttctgttatcttcaaca atacactgctaggtgtattt agtccctcatgatgctgggc ctcctcaagtggcgccaggt
3603  caagcagtctcctgttttt  ggtggctctgaagaagactg tgtcccagtgactggcagtt tgaattcgagcttctctt
3683  tccttctcagtctttggcag gcagagtgacactggtgtgc ccaagcctggagcttctctg tttaattctagtttattttc
3763  tttatcagactgaaaaacaa atcaggttggttataattct tataaacacgaaggtctcac ctttgctgctgtctccgct
3843  gtgtgggtctgatgtccctc gggaatctctgttgaggctg ctgcagtgtgtgtgctgta  gaaagggcaaggtagaatgg
3923  acagaagcgtgctgcccacc ccactgtcctgttcctaaat gatgagcactggcccgtg   aagagcctagagaactccct
4003  cgtggggagatgcacacaat gccaggagcacacaggagc  ttgagttccagcttggcagt gtcttctcttggtgactt
4083  atcagctccagctgccctgg actaacaaacaagctagct  cactccagtattgataatc  gaaggtcctggttctgttt
4163  gagactgatcctcactcggt agccttgaactcttagcaat tctcctgtctcaactttcaa agagctgaattacagactc
4243  gagccaccatatgcgactga aaccttgttcctaatcctg  actgtgaacgactcttggt  ttggttctttctccatttct
4323  ttagtgtatgttttagttcg cgtcctacataatctattgc ccatacttagaaacaacagg ttagagacagcattgggtcc
4403  agcagagcctcacactgaag ctcagtcctgccactgattt accgtgtcagctcaagtgac tcacttccaactcctctgct
4483  cccatctgtagagtagaca  tcaccatacctgctcttttct gcccacattctgtcattaac atgttcattcataacgatg
4563  gtgcaaaagtgcttgtaag  taaagtgctggggaaatgtt agctgtcgataatggttagg gttaacttttattgagtgc
4643  ctgttgtgtgtgggttggg  tggggttttttagaggctt  ggtagttttctactttctt  cctacttagcttttctcct
4723  aagcctttatggtatgtatc attgcctgattgtttgagtg tgtgcactgaggcacgcctg tgcatgtttgagagtatgct
4803  tgtgcgtgctctcgtgctca catatgtatggtgtgaatac actgagagtgcaggccggc  acactgggctggctgttagc
4883  ctgtgagccctgcctacattgt ttgcagatcttccttggaca ctcctgcttgtgagcatttt gtgtggagtgactgtttagc
4963  tggctgtagcctacagctaag cctttggtaaaccctgagt  attgggaaacacccctgggct gtggctgtgtgtgccgacg
5043  gttgcttgggtacagctgga aactcttcatagaaagttga gctcacatgctattagtatt aactgagtgctaaggaacct
5123  gtcttgggtgtacctgctt  gccctctcatgcagtttatc ttgagcttggcgaacacact tacagattagtagagcttt
5203  tgtcagccctgggaggtggg tttcgtggccacaagtgggt agcttggaatccaagactcc tggcttctaggttgcattct
5283  cctgtggtctttcaaggg   aatgctaggggaacattttg gacattagattatttctagt cccaagcacacagaacata
5363  ctgttcctaattgcctttt  ttttgttttcctcctcaatct ggttttgaagtgttggtttt gaaattgccccctgagagc
5443  ctgcctagtgtgtgcagag  ggaagatagtgaacaggaa  gtctgtagaaagtatcttcc tttccaggaccttgtgcccc
```

FIG. 2e

```
5523  ggagcagagtcagcatggtg  tcatatcgcttttggctatt  ccagaaagagatgaggttta  ggtgagaatgaacctttag
5603  aacctttctagaacctttctgt  tgagtatgacaggaatgccc  tgaataggtccgaagtgca  tggccacttgtttgtcttt
5683  ccataagcaagcagcttcag  gtacagacaataagactagg  ttcttggagtgagaccctgc  acttggtgccatttcagctc
5763  cagatggacactggagtcc  ctacacagcaggctctggga  tggctggctttgctatgtac  tgttgcctgctctacaagag
5843  cttcccaggttactagcctt  tgtcgacgctgggctcgctg  gccaggcttggcattggag  aaggacaacttgccacctg
5923  gcataggctgtgtgtttgga  gagtcaggaggtctggtgaa  gcccgcaagtggaggcaagt  ttagtgggactgaggagag
6003  ctcagtaggaaatctctggg  ctagtgacaggcaggtgtgg  tggtggtggcgaggtggcgg  gtctagatctcctttagag
6083  atttgcctaggatcgtccc  tgctgactctggaactcaga  ggcctccagaggtgtctcct  ctgggagcctctcaaggtc
6163  tcccatctcctactgtttat  ggctttgtgggctacctaat  tacatagagaagatatgttc  ctctgcctccagccctgaa
6243  agttctgccagtgactcac  ctgagcctgcagccatgt  gtacacaggcgctctcagg  gcttctgtcctgctggcttc
6323  agcctttctagccctgtg  ttctcggcagtggtagcatc  tgggaaccggtcacctct  tatttgcagctcctccctt
6403  tcttggtgtcttccccttt  ttaactactggttctgatgc  cttagactcatgctgaaatt  ctccttcttttgtcctagc
6483  cttgtctctgacttcttgtg  atcctctgggcctgtgaaat  ccgctcagggcctccattt  ctaacagtcacacactgtg
6563  gagagaccgagtcctgggat  ggtgaagctaaccctgctgg  gcttctcaagcttcatttgg  tttctcttattccttctgg
6643  aggtactgcctgccccaggg  gagtccagactagaccact  ctggagttggaggtggggca  ggttttcagatcagtgccct
6723  tggcattcgttgtgggaatg  gggtggatgggccctctggg  caaggtcaggctggggtgg  aggccaggtgatgttctccg
6803  caccccaccccagacct  ggcaccctcccaagtccg  ctcatcagcaggaatgaaag  cagtgccgggcaggttgggg
6883  cagtgggcaggtgggcgtgt  ttatcgctgtgctcatcagc  tgagtcacgatgccaggccc  cacaagtcctccctggagc
6963  tcacccaccaccttgacc  caccagcaccactagcagg  aagtagggcaggcagtgag  acaagaccagctgggggtc
7043  tgagaggcaaaggggagttg  ttcatgacctggctgtgcat  ggggacttgtgggtgtctca  gatatctctgtctccagga
7123  ggaagctgtcttaagtgcca  acctgcctagagccctgct  gggtgcaggaaatgcacaag  ggagagtgccatccatgga
7203  ataggccatggagctagac  cagtgacagtgacagtgaag  tcagccccaccctgtctt  ccgagccagctggagggttt
7283  ttatctcagattctgcaaa  ccatagaatctagtcaggag  cctagactgcaaagcaggct  tcgttgatgcttttaacttgc
7363  aggcttcctgggtatgaggg  atacttagaaaggtcccgca  ggtaggagggcatcaggaa  gtagaagaggcaggcact
7443  tctatctcctcattgcccc  cttctcccatctccaaggat  ggtaaaagaaccccttccag  tacactgacagagaggaaaa
```

FIG.2f

```
7523  cccttcatctcacccattt  ggatctgtcgtatcagcatg  tgctggccctgcttccatac  cagaggtggctagagatgtt
7603  ccctggaattcactggttg  gggacttgatgtatcagag   gggcacaaagtaacattaac  tctggtatcctctgcagcaa
7683  atcggagatcccctctccta ggcgagttctcagtggatat  ggaggtcaggtttggcttg   tagggcccagcaagagtcg
7763  ttgatgtcactccagcttct cccgaggaagatgagggtgc  tgtgttgggatcacatctct  ccctgaatggcatgttgggg
7843  agggatggagccctttgcttc tgaccctaagcttgtctt   tagtggccacagtctctgg   gttctgtcctacctcctgc
7923  ccttgtgtgcttcaaaggca  tgctaaaggactctcggcc  attccgaatggcacagtgtt  ccttctgttctcccaccccc
8003  agaaggaggcaggcctggat  tgtagattcctagaagtaag  tggccctgagcatgctgttg  atgaactggaaccaggcag
8083  gctgggcatcctaggacctg  tcttccatagaagtctgaa  tcagtctacctttgggactg  agtaagggctcctcacata
8163  tcagctggctagtccatctt  ggctgatctaaaccacatta ggctgaagagaagcatggtg  tacagtctggtccaccgaa
8243  ccacatactggcttatcag   ttctcgtataatttttgcagg taacttttttagctctaagcc tgtctcctcatctgtgaaat
8323  cgggtccctcatatcctgcc  tagaaggcttttgaaaaga  ttaatgaagtagtatgccga  gtggttgggttctctcctt
8403  gactggagcaagtctctagg  agtactaaggatagcctgct gtgtgcagcacccccagga   ctgtgcctgagtaggaggt
8483  acagagtcttcatgtgaatg  gcccttctgtcttgccccg  aagttagtgttgatgtcata  gagtctacaaacatgccttt
8563  tgtccttcctcagaagtcca  agcctttcctggcagaccag acattcatctccactgagcc  tctatgtgagactggctcct
8643  ggcctgagctgtgtgggctg  agctgcgaatgggaaaact  agacacctgggcacctgggt  ggggctcgggacagcagtg
8723  tttcagttgtaggcactgtg  cccctgcctggagcttctga ctgaaggttaccctgagagg  aagcaggttccctatagaca
8803  ctaacatagctgggtcagag  tgcaaggtgggtgtgcccct gccctgaccattcagtgca   aaggctgctcttctgggagt
8883  gagagctctgacagagactgt gatggccgagggggtctcaga gcaaacctgcctggcctctc  cccactctgatggatatgtg
8963  ctcttaaacaagtgactgtc  cactttgcctcaatttcaac atctgtaagatagataggc   gttatggtctgaaaatgtt
9043  ttaaagattagttagctaat  acagggaaagtgctctgaca ggtactggcaccttactca   acaagtgctggtgcctg
9123  atttcctaaggtctcgacct  gtccctatgcttcaagtgcc cctacagccttggtcaggcc  cttaggttctccaccacc
9203  gctggcccagaacctagac   tgctggacctgaccctg    tttcctttaagccaccctg  cgtcaactctaaaaggcggt
9283  ggagttgtttatctaggctg  tgaggtgtcagagaaaggac ctgggccgcttttgttcctgt gtgggctgggccactccag
9363  gaactgagaaacccaccac   cttttcaaaaacagctctt  ctcagagtctggcacctcag  ctagccaccatgctgtggga
9443  ccactcccagcatgctctgc  ctttggtttgtttcccaggg gcctcagtgcctttaaaga   tgcacaggcatctttagttc
```

FIG.2g

```
9523   aagggaaagaggaaatgaa gtgtattgctgtggtggt attcctgtcacttgcattct cacagaggctaaagaaattt
9603   gctctttgtatcttctagtc tcttctttatgatctttcc catctgttgtatcccaactg cagggcccagttctagaat
9683   tagccctccccatagga gccgacttatgctataatgt gaatgacaagtatcctttag ccttccacagccattta
9763   atttcaaaagggcattgca caaccgcagagacactaaga agagaggtttgtgatcaga gttacagcccagcctccca
9843   gctggtggccggctgtgc agtgtgtcgaaagcagtag tttctgcttcagtgaaactt gagatccttattagcca
9923   gttcagggggcggaatgcca tgcgaagtctatgtgtcaca ggtgtcaggccccatatcc tgctgagtctagaatcagct
10003  acgtagcagttttgggggta ttgccagactgggagttac atcccagaagcgagaatggt ggggttcctatactgctcca
10083  gacaggatctttccccaag tttgtcagccaccctcttc aagtccctggctctgacca gcaagacgtatccaaagaa
10163  actgaggagccccttcactt ctttttaggatagtgtgggg ccagcatggtggggtttggg aatggctttctgtctcttcc
10243  atcatcacaggctacttccc agagacactttgattctggg catctccagcagtcacctgg cccacaatgctttgctgccc
10323  tttgcttcagccactgtatc tggttgtccctttgaaggtga gccagagctcctaggcagag agcatgtgctatacaaagcc
10403  gtaggctgggccctgggaac cttcttgctgtcatcctcct gtcaaccccctatggtatgg tagcccacataaggcttgtg
10483  caaaaaacaggccaaaacat aagttatctttttcactctat cggtctttctcatttttccca tgtacgttcggctggccag
10563  gcccaaaagatttgaagaga ggtggctggcaagtctaggg gaatagttctatctggttcc ctccaggagcagtgcctagt
10643  gagaggctgggctgggcagg gcagggcccctttgctccaca ttgcctgaagtcccgccctg cccgtcctggctgggatctg
10723  gcagtctttccagctccaca ccggtctccagctgagcct gctcagagactagtcctggc atgtggttgcaggctggt
10803  tccagctccaccaggaggta tgggcgtctggtactcatg ggacattgacctgtagtggg tatggagagtggaggaatgg
10883  tacaggcagtgtgctggtg ctgacggacttgactccggc attgaccttgcttgcagtc tgtgttaaactaacaggga
10963  atgctgacaaaaagacagt tattaaaacaagacaggat actgcttccactcagccc atcccaagaatcccaaga
11042  cgtacaggaatgtgcaaca gcagtggaattgctgagtt ggggatgtggtgagctgt gtgctccaggaattttgg
11123  gaaattccctccgttgaaa tgctgtcaggtctgagcct tggagtgttttttggggtgc tgtgctcccagctaagcag
11203  ctaacagtctctcttttactg cctgtcctccaccttgcccc acccctgggttgggcctctg ttcactcctgctggtcac
11283  cagtacttcagtgcaggtct cagcttgattcttgtggag agagaaaagttgataaatc agggtgcctgtcagccgaa
11363  atttgggtgtgtcctgaagg caccaatggggcccctccct tctggaggtgcctttaggaa ggggtttctggtcttgagg
11443  cctccttacagttttcttagc tccatgggagagaagtgagg agttgggtatcgtcacccca gcatgaatctctgtcacct
```

FIG.2h

```
11523  ctcagcatgcactgtccagc  ctgatctttgatgccataa  aagaacagaattatcctctc  agagcacttcatttccgcc
11603  agcacagtgggtacagagac  aagctgcccagactcccagc  gagggactagttgagcccca  gcatggactagttgagcta
11683  gacctgatacagtcccagag  agcctcgttgaggaagcttt  gggaaattcaccagcatt    tcagccaggactggaggaaa
11763  agtgattatgggaaagaga   gcagtcaagacccaggctg   taggacacaggatacaaact  gagagctaccgagataggagt
11843  agttttagtcacaatctct   cctgtccgccctaccctcca  ggagacattgcacctgtag   aacagctgcccggagtcca
11923  cctttgggccccctggta    gctcagtagtgtcagcatcc  tctcattgacatcagtcagg  ttacacagtgggcagctaa
12003  tgtgaaggcgctaggctggg  aagccagctacttgggaaaa  ctaggttgttcctggtaggc  cctagcaggaaggcagttcc
12083  tcctttcttgtggcttta    gggtcttttggaagctttga  atgttccctcagctcgttgg  tgaagcaggccctcctgta
12163  ctgtggtgtttgtcttcgaa  gagtgaaggcattggaagta  aagactgatggggcgccttc  ccaggatgctttgcttcttg
12243  cgctggcttacagagctctc  ttgctacctagtgccttgac  tttgaacaccagattcagtc  agggaacaggagtagaggtc
12323  ttgcctgctgctgagccctgc gcactgcaggaaaagactcc  tctgagtggagccttttcctc ctcaggtgactgctttcaaa
12403  gtacagcagcctctgagggg  gaagtgtcattgacattgt   ggtagttcttgggtccctg   gatacagatgtcatgcccag
12483  atcataggtctgtttgtaca  gagggaggcgagttctgtag  ctcagagtcctcagtacccc  agagttgtggctctagggt
12563  gagagagagactacagcc    cttcaatcacagtctgacc   tgtgggtagggtagatctc   ttgcatactatgaacctgtt
12643  tgaaaccctggtatttgc    tgtgaatagagtcttggtt   gggtaagaatgtggatgtt   tatcttggtgtgactctcgg
12723  gtggggtgggggatatgtc   cctgtctttccaatgtagt   atgctgagtggacagagacc  gtgtgactgaagctgggct
12803  cctggaacagtgtgtgttg   gtggggtggggcgcaact    atctggatccagactgctt   gggaatgctgtgaccagc
12883  tcctttgataacagcagctc  tttgtcactggatgttgtga  ctaatggactgttgttgattc agttactcggctcccaccca
12963  cagacgccgggcttctgtt   gtggcaccaggcagctgcag  acggcccacaagttgcctc   gctttcccactccacgaagg
13043  taagttccagcactgccca   aattagagacttgagtgg    tccctcatacccactccc    tgaggcttcctcctgaagc
13123  ctggaatgggcactgggtg   tgtacgtgctgtgttttctg  ttagggtcaagaccaggctg  tttcttacctggtcgtacc
13203  tccaagtttccagtgatga   gtcctgatttttgaagtgaa  ggaatcattttaatatcaaa  attctgtgacttaaatttt
13283  tttcttttattatgtgtcat  ttcatatgtacgcatatttt  tttgtctgtgtgtggacatg  cttgtggcgatcagaggaca
13363  cttcagaaaagtcagttctct cctgccgtgtgggtcctggg  gaatcaaatccaagttgtca  ggctttatcctgaaaataaa
13443  aagtagacagcccttgggat  ccaaagcttcttagggctgt  gtgtcttagacaccaccagt  gttgcacagctggtaacatg
```

FIG. 2i

```
13523  acagtgtcctggagtgctga ttggaagccacaggcctctg tgcagggcgtagacttcca gggtacggggcaggtgggcg
13603  ttctctacaaaaccttgta  atcgcggacgtcttggagat gccccctaggtatcatgatt ttggtgtgtgacacagctga
13683  actgtcttcatactcaggat atcatgaagtgctgggtgc  agaccactcagcctcagg   cagccaggacccgggctcc
13763  atcagattgcggtgactacc acagagggtggccttcctc  cgtcagtgtgggtgtggga  gctggcaggaagtggctcca
13843  ggcttccttaagcatcctc  tgcccacagcccaaacatg  ttctttggcaatggcttgca actagaggtgaactctctcc
13923  tgtactatgtcctgacccac gctgctgcatctattatacc tttcacacgcgtgatgggta cccagcggggctgctaggca
14003  gggttaagcactcatcttgt ttcctggtgctgaagctgtg gtaaagaaactgaggccatt ttcccttgagagagatggtc
14083  tcagccagtctcttctcggc ctggggagcccggaagaaag gatgtactacagtgagtgga cacttgttggctgatggcct
14163  tggtaggtccttcaccctgg gaagtgctgtttcttatctg ttagagatgctgacctcagc aggactggagaactgcatg
14243  ggaggtgtaggaatgaaagt gagtgggaaaattatctcc  agcccctagggaagtctgagg cctgtccctttgtcctg
14323  gactgggccctgccttggg  tgtctgtccaggtctttgc  tctacagcccagcggatgc  ccaaagtagacgagtcaact
14403  ggtccttctttcaccctgt  gtccactcttcatgtatcta ccttcataatccttctaggt aaaacaagcctctaactttg
14483  ggttttcaaatcagccagct tccaggctgatagtacgaa  ccatgaaaatcttttcttacc atgaggttgttttctagtgt
14563  gtgtgtgtgtgtgtgtgt   gtgtgtgtgtcaggcagct  gtacgtacacatatgtacct ctatcagtgtgtgctgtg
14643  taccacagactcgtgag    gaggtcaggcaaactttata aaatcttttttttgctt    cactgagtccaggtcac
14723  acagtggcaagtgctgagct ctgttctctgttcttgattt gttttgtgagcagctgatgt tcttaaggcttgcggaggg
14803  aaaggtagggctgcttgct  tcttcccgagtggccggtca atccctagacatctctaagc cgtggccacagtcctggaa
14883  ggaccagtcagaagtgat   actgagatggccctgtgagc cctctcgaacacacaggtt  gtaaatagtactgattgtt
14963  acattggagactcgtcagct gggtggagtcctgttcaga  gggagttattcctcccccca cattctttctttctgggc
15043  tgaagtctcttttccttctta ctgtgatgctgtcatgata gtccccagctgagagtggaag gcgggcagtcaggagctg
15123  cttctctttgcttagcaggg gttggagacttggggtgtag gggttggctccccctttccc tgccctggacctggtttctg
15203  gtttcagcagagattcgttc tagaaacttgttgcgtaaac aagatcacaaagcgataagc ttgagcaaaacccaggggaa
15283  caaattgcttccctgtgaag acccatctttagctcttaga gaagcctccctttggaaa   ttgctgactttcaggcttc
15363  tctgtgaggaagaggcta   gcgcgtatgtttgcctgg   attccaataatctttgcgg  ccttgctaccctgttga
15443  acaaggtctgcactcctaat gcgtgcctcaggtgtctga  gacctctacccatccag    cttccttcctatggaggg
```

FIG.2j

```
15523  agtcagtgggttaggagaga  atggagttgagtcctggaat  gaggaggaagctatgaactc  gggcctgttcctgtctggt
15603  gggtgctcttctcgccgct   gaaggagcagccgcagga    agactaccacaggaatccga  gtaccacctggagcagtgta
15683  tacaggatgtggctgatgt   gtggtaagggcatgatggc   tgatgtgtggtaagggcatg  ggatctgattgctctgtgga
15763  tgggccacagggaaatttt   gagtgtctactgcagtagtt  ctcaacctgtgggttgtgcg  cccctgtgtgggagttacat
15843  attagatatttacattatga  ttcataactgtagcaaaatt  acaattgtgaaagaaccaag  aaatcaccgcagcatgagaa
15923  cctgtattaaagggtcacgg  tgttaggagggttgagagcc  actcatcctctggtctagg   ccatgcgggctgtaactgc
16003  tctctggagttaagccacag  tgaaccagctgtctcttgca  atggacttgtggaggctcca  aacctttgtcccaggggaga
16083  agagcttgcttttgctttgt  acttttaaaggaagttcagt  ggtcttcgggcctttgtggct gctgtgtggaagtgcccc
16163  tgtacaataagctgtataga  tcgtgtacaactgcagtttt  cctccgtgggtccaccaacc  actcctgactccacggatga
16243  gtgaggccagtaggctgtg   tgtgggtcctaggccaagc   atcctggaccacgatgagcc  tcagctagaccactctggat
16323  ctttagcagaggctcctaga  gagctggctgcttcctcct   gccttcttttctcttaaaac  ttcgtctcaatcggaagctc
16403  ctctgtgcacgtgacctcca  gcctgggggtcgccacaaa   tccctcatcacaagacgag   cagctcgcatgagggacacg
16483  acacttgttacctaccagc   tgtgggtttttgttggttg   gttgttttgtttttgtttttgt tttttactgtacagaagt
16563  gttgtgacatcagatgtcag  ctgttagtgctggcaccatt  ttacaggtagggaactgagg  ctgtaagatgtgtagtgaca
16643  tcgctaaggccactcagttg  gtgaggcttaccaaggtca   ggtcttggagcctttgct    gaaccatgtacttctatctc
16723  tgtttttgtgaaacaaagtc  tatatggctctctggctagcct ataaccccatatgtagacga gctgacctcgaatacactg
16803  cagtctttatgtctgcctt   ctgggtggcaggattgaagg  catgtgattcctcctaactg  tacactttaaaaaaaaatc
16883  attcttttgttctggtctgtg ccaggcctgtaagatgtt    ctgtgctgagctggctatt   tgggttagtctcattgctga
16963  gcagggccctgtatcttcc   ttctctgtcacttgcttacc  tgggtcttcctctgcacta   gctatctagaaccagtact
17043  gagagcaactatgggcccaa  ctctgccctgccagcct     gcttagctggggcggtgtt   ccacttcctgccagtcc
17123  tgtgggactgtgtttgtact  ccaccacttcagttcctg    gagctggagcaggccaggcg  gctgcattcctgcagctgct
17203  gttgccagggagagcccatc  ccattcacttcagtctcctt  aatgtagaagccttgtcgaa  ttagcttccactgtcccaa
17283  cccaagagtaccctgtcctt  tcttcactaagaaggccagg  atacagtccttcctgtgct   gataagacaggcctgggac
17363  aaggcctgggaccacactgt  gtgggcaaagctgcttcagc  accgatggctcctccatgcc  aagcttggctctgtcttcta
17443  cagttgagacttctgtgcgc  acacccactgtctagctcag  ctggacactgattttcttta  aatgtatagatttgggtg
```

FIG.2k 17523 gggtgtgctgaaagctccca ctgatgcccaagctgagt ctcagagtatgatcaattga tggctttcatgggtatcaca
17603 gcttctgttccaggtcaga ctccctgaccagtcagagca tcctggggttagacaatgtc cccgtcacttgtgcctcac
17683 ctgcaccagctatgatgt tatgcattgagggtatgag aaggaccagggtttcccag agttacgccaggcgcacag
17763 gcaattgtttcctacatgtg tggctgaatgttggtga gcctttcagctgcctacaa taggaacccaggatactgg
17843 gcattgaccaaggcatatct cataccttttcttatcttt ctgcagCAAATTGTGGCTGT AAATGTTCCTCCTGAAGATC
                                                                    GlnIleValAlaVa lAsnValProProGluAspG 18923 AGGATGGCTCTGGGGATGAC TCTGACAACTTCTCTGGCTC TGGCACAGgtaagactgacc cagaacactgagatggcata
       lnAspGlySerGlyAspAsp SerAspAsnPheSerGlySe rGlyThrG 18003 gatcatggctgagtggtga gcaggcagtcaccagcttt tagtgaacccccttcttctc ccatccatcttagccatt
18083 ggagtcaggacagtgccaaa aggaagaatgtatccagct gcaagccactcagctaagag aaactctcagagaaatgaag
18163 gggttccaccaggccatggg cagccactagagccaaccct tggaggagtttgactccact gagccttgtgtgtggtgttc
18243 catctgtgagatgggaatac tttgcccaagacctgttag aagctgtaggaagcacagag tcggctagtagtagatttgc
18323 tctcacctccatctctcgat accagttctctgcagaagctt gggtttgtggaggggtggg gggtgagggagaaggctg
18403 tgagctgcagctagccagag gggtctcccagaagaatggg gagagctaagaaggaaagtt gaggtcacagtgggaaggag
18483 accagacaaaggttggaa ggtagtaaaatgcagccgt gtattcttgggagccttagg ccttgggcaagaggtagaa
18563 gagtgttttgtcctgggctg cagtcctgtatcagctctgg tgtcttgccccacgctcaca gcaggatcccttcccagatt
18643 cccgagaattttctcacagtt cagagagcacgctacttgta ggcaggtgaggctgcaaagg acagctttctggctaatt
18723 ttcaaagtgagttcagcctt tgctaggtcacctttgggt ctcagaaggcttcagctcct ggtagagcatgaatcacgtc
18803 aggcgtgatgctggagacct ctcctaccctgacacccccaa accccacctctgaccctgc agTGCTTTGCCAGATACTT
                                                                    lyAlaLeuProAspThrL 18883 TGTCACGGCAGACACCTTCC ACTTGGAAGGAGTGTGGCT GTTGACAGCCACGCCACAG CTCCAGAGCCCACCAGCAGC
       euSerArgGlnThrProSer ThrTrpLysAspValTrpLe uLeuThrAlaThrProThrA laProGluProThrSerSer

FIG. 21

```
19963  AACACCGAGACTGCTTTTAC CTCTGTCCTGCCAGCCGGAG AGAAGCCCGAGGAGGAGAG CCTGTGTCCATGTAGAAGC
       AsnThrGluThrAlaPheTh rSerValLeuProAlaGlyG luLysProGluGluGlyGlu ProValLeuHisValGluAl

19043  AGAGCCTGGCTTCACTGCTC GGGACAAGGAAAAGGAGGTC ACCACCAGGCCCAGGGAGAC CGTGCAGCTCCCATCACCC
       aGluProGlyPheThrAlaA rgAspLysGlyLysGluVal ThrThrArgProArgGluTh rValGlnLeuProIleThrG

19123  AACGGGCCTCAACAGTCAGA GTCACCACAGCCCAGGCAGC TGTCACATCTCATCCGCACG GGGGCATGCAACCTGGCCTC
       lnArgAlaSerThrValArg ValThrThrAlaGlnAlaAl aValThrSerHisProHisGl yGlyMetGlnProGlyLeu

19203  CATGAGACCTCGGCTCCCAC AGCACCTGGTCAACCTGACC ATCAGCCTCCAGTGTGGAG GGTGGGGCACTTCTGTCAT
       HisGluThrSerAlaProTh rAlaProGlyGlnProAspH isGlnProProArgValGlu GlyGlyGlyThrSerValIl

19283  CAAAGAGGTTGTCGAGGATG GAACTGCCAATCAGCTTCCC GCAGGAGAGGCTCTGGAGA ACAAgtgagtggctttgcat
       eLysGluValValGluAspG lyThrAlaAsnGlnLeuPro AlaGlyGluGlySerGlyGl uGln 19363  ttcctgggtggccactagtg cctgcacctgccgcctaat gtcctcattacagtgacagg tgacagggtcccaccttcct
19443  cctgcccgaaacagactgat tgcaagatcaggaggtgggc gactccttagatgtcattca ggagcttacagcagggtgaa
19523  ttttccgtcttagaccttca tgggaattttcacacaacaa tgtgtacgttgtgtcactgg aggcggtatctgtgtcttgg
19603  cctgccagggtcccagtgt gactgactgcattccttgac agatgctggtagattggc tacgtctgatggggtggca
19683  ggggatcccatcaggtatgg cactgctcaggttgctgttg tgtcagtggctccagctgac ctgatccaacctaccttc
19763  tgtagGACTTCACCTTTGAA ACATCTGGGGAGAACACAGC TGTGGCTGCCGTAGAGCCCG GCCTGCGGAATCAGCCCCG
       AspPheThrPheGlu ThrSerGlyGluAsnThrAl aValAlaAlaValGluProG lyLeuArgAsnGlnProPro 19843  GTGGACGAAGGAGCCACAGG TGCTTCTCAGAGCCTTTGG ACAGGAAGGAAGTGCTGGA Ggtgagtcttctttcaggtg
       ValAspGluGlyAlaThrGl yAlaSerGlnSerLeuLeuA spArgLysGlyValLeuGly G
```

FIG.2m

```
20923 gagaggaggaggcaggtggt ggctctgaggtagcctgggt tgctggggtgaagcatcttt agcagcaggtggggaagga
20003 ggagggtcaattctactcca ggccacctcctaggctgtcc gtctagtctggagagacta ccactgacccgtggacta
20083 ctgatctgagcctgcctctg ttcactcccctagGTGTCATT GCCGGAGGCCTAGTGGGCCT CATCTTGCTGTGCCTGG
                                                lyValIle AlaGlyGlyLeuValGlyLe uIlePheAlaValCysLeuV 20163 TGGCTTTCATGCTGTACCGG ATGAAGAAGAAGGACGAAGG CAGCTACTCCTTGGAGGAGC CCAAACAAGCCAATGCGGT
      alAlaPheMetLeuTyrArg MetLysLysLysAspGluGl ySerTyrSerLeuGluGluP roLysGlnAlaAsnGlyGly 20243 GCCTACCAGAAACCACCAA GCAGGAGGAGTTCTACGCCT GATGGGGAAATAGTTCTTTC TCCCCCACAGCCCCTGCCA
      AlaTyrGlnLysProThrLy sGlnGluGluPheTyrAla 20323 CTCACTAGGCTCCCCACTTGC CTCTTCTGTGAAAAACTTCA AGCCCTGGCCTCCCCACCAC TGGGTCATGTCCTCTGCACC
20403 CAGGCCCTTCCAGCTGTTCC TGCCCGAGCGGTCCCAGGGT GTGCTGGGAACTGATTCCCC TCCTTTGACTTCTGCCTAGA
20483 AGCTTGGGTGCAAAGGGTTT CTTGCATCTGATCTTTCTAC CACAACCACACCTGTTGTCC ACTCTTCTGACTTGGTTTCT
20563 CCAAATGGGAGGAGACCCAG CTCTGGACAGAAAGGGACC CGACTCTTTGGACCTAGATG GCCTATTGCGGCTGGAGGAT
20643 CCTGAGGACAGGAGAGGGGC TTCGGCTGACCAGCCATAGC ACTTACCCATAGAGACCGCT AGGTTGGCCGTGCTGTGGTG
20723 GGGGATGGAGGCCTGAGCTC CTTGGAATCCCACTTTTCATT GTGGGGAGGTCTACTTTAGA CAACTTGGTTTTGCACATAT
20803 TTTCTCTAATTTCTCTGTTC AGAGCCCCAGCAGACCTTAT TACTGGGGTAAGGCAAGTCT GTTGACTGGTGTCCCTCACC
20883 TCGCTTCCCTAATCTACATT CAGGAGACCGAATCGGGGGT TAATAAGACTTTTTTTGTTT TTTGTTTTGTTTTAACCT
21963 AGAAGAACCAAATCTGGACG GCAAAACGTAGGCTTAGTTT GTGTGTTGTCTCTGAGTTTG TCGCTCATGCGTACAACAGG
21043 GTATGGACTATCTGTATGGT GCCCCATTTTTGGCGGCCCG TAAGTAGGCTGGCTAGTCCA GGATACTGTGGAATAGCCAC
21123 CTCTTGACCAGTCATGCCTG TGTGCATGGACTCAGGGCCA CGGCCTTGGCCTGGGCCACC GTGACATTGGAAGAGCCTGT
21203 GTGAGAACTTACTCGAAGTT CACAGTCTAGGAGTGGAGGG GAGGAGACTGTAGAGTTTTG GGGGAGGGTGGCAAGGGTG
21283 CCCAAGCGTCTCCCACCTTT GGTACCATCTCTAGTCATCC TTCCTCCCGAAGTTGACAA GACACATCTTGAGTATGGCT
21363 GGCACTGGTTCCTCCCATCAA GAACCAAGTTCACCTTCAGC TCCTGTGGCCCCGCCCCCAG GCTGGAGTCAGAAATGTTTC
```

FIG.2n

| | | | |
|---|---|---|---|
| 21443 | CCAAAGAGTGAGTCTTTTGC | TTTTGGCAAAACGCTACTTA | ATCCAATGGGTTCTGTACAG | TAGATTTTGCAGATGTAATA |
| 21523 | AACTTTAATATAAAGGAGTC | CTATGAACTCTACTGCTTCT | GCTTCTTCTTCTCTGGACTG | GTGGTATAGATATAGCCACC |
| 21603 | CTTTGCCAAACCCTGGTAG | CTCGGGGAAGCTTGGCTTAA | GGCTGCACGCCTCCAATCCC | CCAAAGGTAGGATCCTGGCT |
| 21683 | GGGTCCAGGGTTCCTCTGAT | TTATTTGGTTTTGTTGTGTT | GTGTTGTGTTTTTCTTTTGG | CTAAACTTCTTTTGGAAGTT |
| 21763 | GGTAAGTTCAGCCAAGGTT | TACAGGCCCTGATGTCTGTT | CTTCTAAATGGTTTAAGTAA | TTGGGACTCTAGCACATCTT |
| 21843 | GACCTAGGGTCACTAGAGCT | AAGCTTGCTTTGCAGGGCAG | ACACCTGGGACAGCCTTCCT | CCCTCATGTTTGCTGGGACA |
| 21923 | CTGCTGAGCACCCCTTGCTT | ACTTAGCTCAGTGATGTTCC | AGCTCCTGGCTAGGCTGCTC | AGCCACTCAGCTAGACAAAA |
| 22003 | GATCTGTGCCCTGTGTTTCA | TCCCAGAGCTTGTTGCCAGA | TCACATGGCTGGATGTGATG | TGGGGTGGGGGTGGGGTCAT |
| 22083 | ATCTGAGACAGCCCTCAGCT | GAGGGCTTGTGGGACAGTGT | CAAGCCCTCAGGCTGGCGCTC | ATTCATATAATTGCAATAAA |
| 22163 | tggtacgtgtccattggac | agcagacacttggtgtact | tgtgcagtctcttttggtc | tggaccatgtccaactctat |
| 22243 | ctggttttggaatgggagc | ctaactggcctgtgttctgg | cttggtaccaaatagcaaca | gtcagtggcatcctgccca |
| 22323 | ggcccaggggcaggactatg | ctcttgccatatccaggact | cccgactttgcacctgtttt | ccctctgtgtagcatcat |
| 22403 | gaactccagctaggttgttc | ctttccctgggggtcaggagg | attctgctgactctgaatgt | caggatttgcttttgttctg |
| 22483 | tttgcttattgggcaattct | caaccttcactagcaacagt | ctcatgtgtcaggattacaa | gtattgcttgcacattgagg |

FIG. 2o

```
TCTAGAACAC TTATTAAGAG CCAGGCACTG AAAAGTGCAG ACTCCCTCAT TTCATCCTGG    60
CCGTGCTTAC AAGTAGTTTC CATGCTCTGG TAACCCTGTG CAGAGGGCAG CGTGGGAGGC   120
GGGCCGCTTG GTGGACGGTC ATGGGGGCTC TGCATGGGTG GTTGCCCTTG CCTCAGAAGA   180
ACTCCCTAAG TAAGAGCAAG TTAGCCTCCC TAACCCCTGG TGGGTTGTTG CTTCTTTTCT   240
CCTCTTGTTT CTGCCAAGAG AGGGTGGACC AAGAAGACCC CAGCCTACAG AACATGTGAT   300
CCAAATAAAC TTCTTTTTAG TATAAATGTC CTAGCCTGTG ACGTTCTGGT AGACTAGCAC   360
AAGATGGACC AAGACAACTC TCATCGAGAC TCTGAGGAAC GAACTGGCAT CACATGGGAA   420
CAGGAAATGA AGCTTAGAGA GAGGTTCTGT GGCTTGTCCA ACATGGCTGT AGTTTAAATC   480
CAGCTTGCCA CCAAAGCACA CACATTTCAC TGCTGTGCTG GGCCGGGCCT CAGATCCCAG   540
GGGCTCCGGA GCTAGAAGGA CACGTGTATC AGCCATGGCT TCAGTTTATT GCTGTATACT   600
CTGTGCTTCT GGCTCTCATG GAAAAGACAG ACATTGGGGT TCTTATAATC TCTCCCTCTC   660
CCCTCCCCAC ACTCTATCCC CAAAGGAGGC ACCACTTCTG CAGGTAAATG TTATCTTCAA   720
AGCGCTCACA TCGCAACCTT TGCCCACACC ATCTCATTAA AGGAATTGGC AGTGACTTTA   780
AGGTGAAAGA ACTCGGTGGC TACGTGTTAT ATAAATTTGC ATCTGGGTCT CAGAGCTGGA   840
AGGAAGGCAC TCCCATACAT GCAGTCTGTA CATGCAGTCG GATGATGGAC CAACAACACA   900
TTGTGATTTA TGCCCCTGCT GGTGAGCCCA GGAATCCCTG TAGCACTCTC TCTCAGCTCT   960
AGGGCCCTGC TTGTGTATGG AAAACGCTTA GTGTTTTATA GGTATTTTGT CAGAATACTT  1020
TAAGGAACTT GACCAAAGTT ACAGGGAGGT TAGACAGATT GTCATGGTAT ACTCACCTCT  1080
GTCTCTGACC CTCCTAACTG GGACCTCTTT AGTCTCCCTT GAGGCAGGGA GTGCCACATG  1140
CATGTGTCCA GGCACATGTC TCCTGGTTTA CCTCCCAACG CACCTCAAGT CCCCAAGGTA  1200
GGTAGGCACT TGTATTCTGT AATTCAGAGA GGCAAATCAA ACTGTTACAA TGTTTGCCCA  1260
AAGCTCCCCA AGCAAAGTGG CCCTAAGAGT GAGCAAAGAG ACTGCGTGCC TTCACTGCCT  1320
GTGTGAATCC CTGCAGATAG TCTCTCATCT TGGTGCCCTT CCCACAGAGG CTGGGGCGGC  1380
AGGAGGGAGC CTGGACAGCT CAGACACTGG GTCATTGATG ACTGTTGTGT GGGATACCTG  1440
CCGGGGCGCA GGAGTGAGCC ATGCCACCCC AGGAAGTGGT TCAGGGTGAC TCTTCTTGGC  1500
ACACCTGGGA GGATGTAGCT GGTGCTGGCA CACCCACCGT CACGAGAGCT TCCTGTCCAA  1560
ACCTTCAACA AAGGCGGCTT CTTGAGACAG GCTAGACTGA AGTCACCAGC CTTGGGTGGG  1620
GTCCACTATG TAACCTCAGT GCTCAGGAAC CCTTTCCCAT ACTGTCTGGA ACTATACTGT  1680
ATGTAGCTGG GTTTCCACGC ATGTGTGCCT GCACCCAGTC CATCTCATCT TCTATCTCCC  1740
TCCCCTTTCC CGCTTCCCCC CTCCCCACTC TCCATCTCAT CTTCCATCCC CACCTCTTCT  1800
GGTCCCTGCC CTGCTAAACT CAGGGTAGCT GCATTCCGCT GGCCTTCCCC ATGTTCCAGG  1860
CTTCAGTCCC TTCTCTGCAC CTGTCCTTTG TGAAGTGACC AGAGGATTTC TGATCCTGTC  1920
TCTGTCGCTC TGAAGGGTCA GGAGTTCCTC CTGCCTGGAC AAAGCCATCC TGACGCACAT  1980
AAATAAAACA AACATCAAAC TCTATTCAAC CCCCTGGAAC CCGTGTGTGT TACTTACAGG  2040
GCAAAAGAAT GGAGCAGGGG ATGGGTTGTG GGGGGGGGGG GTGGCATCTG GGTTGTCTAC  2100
AGTTGTGCAT TAAGTTGTAA TTAAGATGTG CATTTCTCCA AATAAGGGAA AATTATTCTG  2160
GATTATTTGA GTGAAGCTGA AAGGTGATCA TCTAGA                            2196
```

FIG.4

FIG.5a
FIG.5d
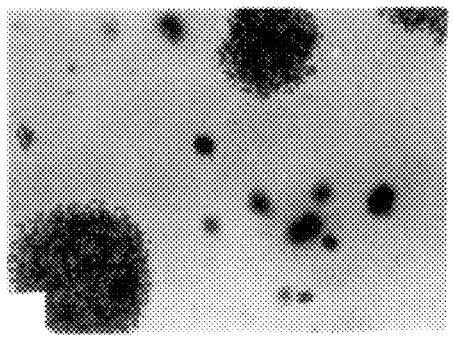
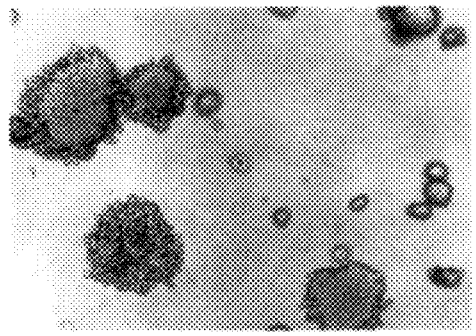
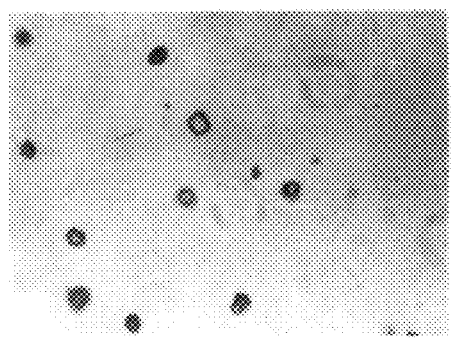
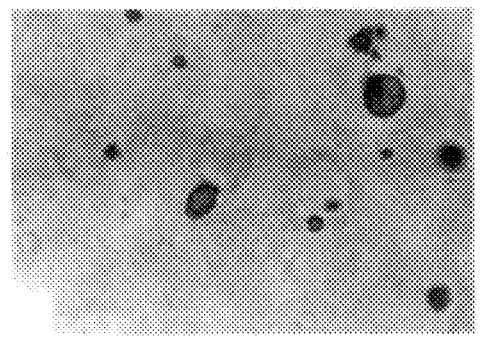
FIG.5c
FIG.5b
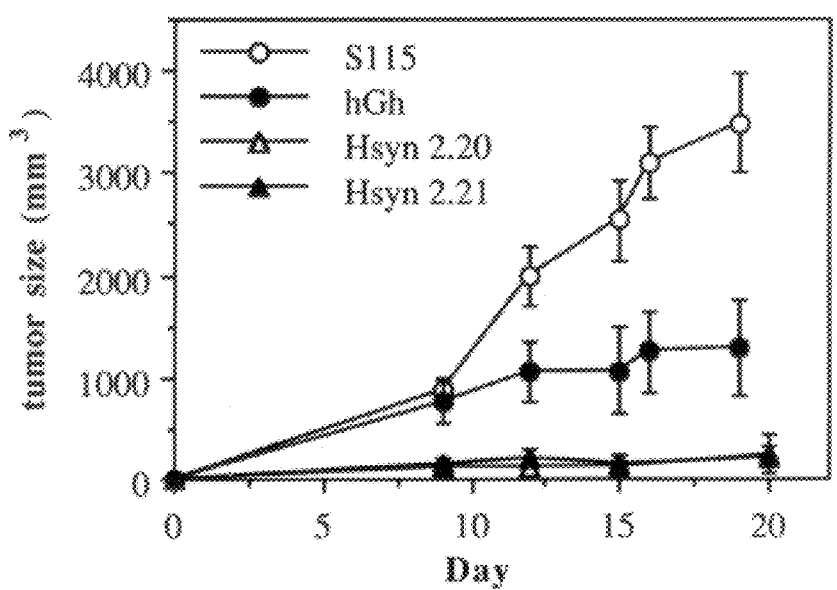
FIG.6

```
  1 TGCAGATAGT CTCTCATCTT GGTGCCCTTC CCACAGAGGC TGGGGCGGCA
 51 GGAGGGAGCC TGGACAGCTC AGACACTGGG TCATTGATGA CTGTTGTGTG
                                                       5
101 GGATACCTGC CGGGGGGCAG GAGTGAGCCA TGCCACCCCA GGAAGTGGTT
                                      4
151 CAGGGTGACT CTTCTTGGCA CACCTGGGAG GATGTAGCTG GTGCTGGCAC
      3                     2
201 ACCCACCGTC ACGAGAGCTT CCTGTCCAAA CCTTCAACAA AGGGGGCTTC
      1
251 TTGAGACAGG CTAGACTGAA GTCACCAGCCTTG
```

FIG.13b

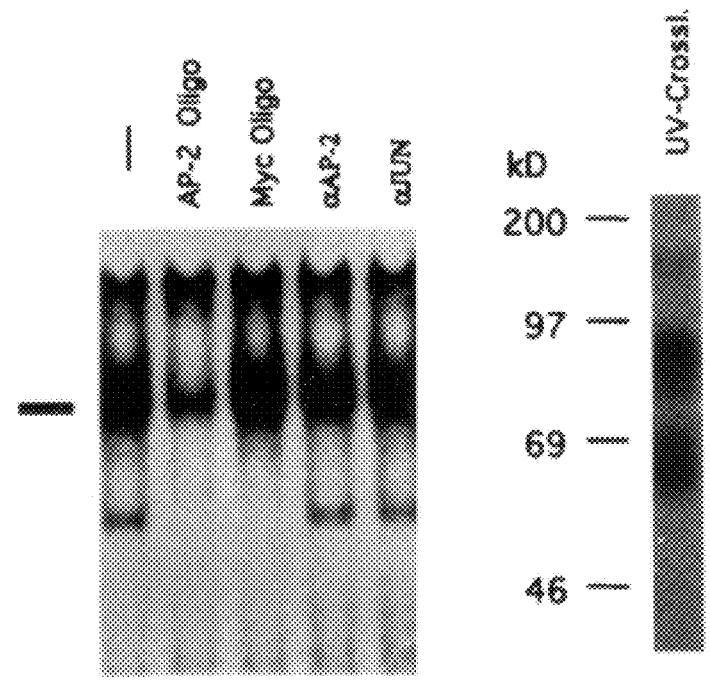
FIG.15c
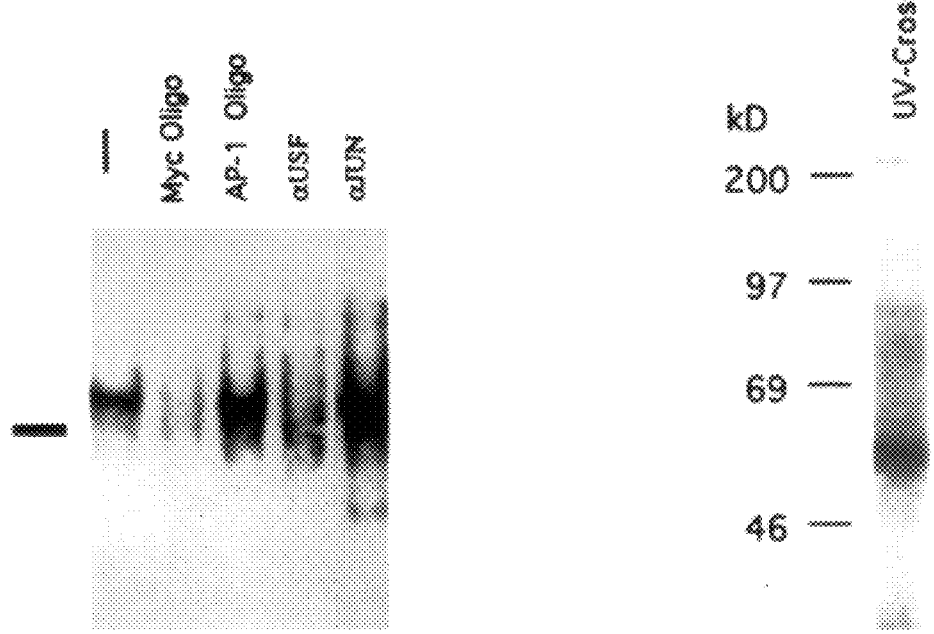
FIG.15d
FIG.15e

```
                           SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
           (A) LENGTH: 26700 base pairs
           (B) TYPE: nucleic acid
           (C) STRANDEDNESS: double
           (D) TOPOLOGY: linear (ii) MOLECULE TYPE: DNA (genomic)

(ix) FEATURE:
           (A) NAME/KEY: CDS
           (B) LOCATION: join(4378..4443, 22026..22106, 23001..23483,
                23905..24039, 24251..24418)

(xi) SEQUENCE DESCRIPTION: SEQ ID NO:1:

TCTAGATATT CAAACTCACC AGATGGAGTG ATGTCCACCC CTATTGGTGG GAGTGACTAG      60

TCTTTCCTCT GTCTTCTGAC TCAGATGCTT AGCTAGCTCT TTAGGACCCA CCCTCACACC     120

TGCAAATAAT ACTTTATTTG CTCTCTTAGT ACCTTTAACC CAGTGGAGTT GACATGAGAA     180

ATTAACTACC ATAATTTATA ATATTTCATT TCATAAATGA AAAGTAAAAT AAATTAAAAA     240

ATAGAAAGGT TTGAGCATGA TGGCCCAGTG GTAAAGGCCA GTGGCTCCAA CGCAAGTCCT     300

GACAAATGGT AACGGGCCTG TTCTTCAGGC TTGAGGGAAG TTTATTGATT GAGGCTAAAA     360

GCAACCCAAA GGCTCCACTT GCCTAGTGTG AAGCCCTGGA TGTGCTCTCC CACACTGCAT     420

GTCCACCTGT GGTGTCAGCA CCTGGGAAGC TGAGGATGAT GGGGAGTCCA AGGTCATTAG     480

CTACATAGTA TAGGCTAGCT GGGGTACATG GGTCACAAAA AAGAAAAAAA AATAAGCACA     540

TTGTAATCCC AGCACTTGAC AGACCAATGG GGGGGGGATT GCTGTGAGTT TAAGACAGCC     600

TGGCCTACAA AGAAAAACCC TACCCAAACC CAAGAAAAAT GAAACCAGTA ATATAAATAG     660

CTATTTTCAT TTTAAATGCT CTAAAGACAC AGCGTTAACA CAAAAGCTCT CGTCTGTGGT     720

TCCTATTCCC TCCTTCTCCC CCAGGTCTTC TTTAATGTAT ACTTTTTGTT TGCTTATTTG     780

CTTGTTTTGG ATTTTGGCTT TTAAAGACAG GGTCTCACTA TGTAGCTCCA ACTATTTGGG     840

AACTCACTAT GTAGACCAGG CTAGCCAGGG ACTTATAGAG ATCTACCTAC CACTGCCTCC     900

CAAGTGCTGA GACTAAAGGC ATGTGACACT TTGCTTGGTT ATTACAAACA TTTTAAAAGA     960

ACATTTTGAA CATTAATAGA TGTATGTATA TATATCACTC TATGTAGTAT ATATGTTAGA    1020

CATTTTTCAC TTGAGATACA TATTTACTCT CAAAATAAGT TTTTTGTTTT TTTTTCTTCT    1080

TTTTAAATTT ATTTTATTTT TTTTTTATTT ATTTTATTAT TATATGTAAG TACACTGTAG    1140

CTGTCTTCAG ACANACCAGA AGAGGGAGTC AGATCTTGTT ACGGATGGTT GTGAGCACCA    1200

TGTGGTTGCT GGGATTCGAA CTCTGGACCT TCCGAAGAGC AGTCGGGTGC TCTTACCCAC    1260

TGAGCCATCT CACCAGCCCC TTAAATTTAT TTTTATCTTA TGTCCATTGG TGTTTTGCCT    1320

GCATGTATGT GTAAAAGTGT CAGAAACTGA AGTTACAGAC TGTTGTGAGC TACCATTGTT    1380

GTGGGTGCTG GGACTTGAAC CTGGGTCCTC TGGAAGAGCA GTCATTATTC TTAACCACTG    1440

AGCCATCTCT CTAGCCCTCG TTTTTTAGTT TTTTTTTTG TTTTGTTTTG TTTTTTGTTT     1500
```

-continued

```
TTTTAAGATT TTCTTATTTA TTATATGTAA GTACACTGTA GCTGTCTTCA GACACTCCAG      1560

AAGAGGGCGC CAGATCTCGT TATGGATGGT TGTGAGCACC ATGTGGTTGC TGGGAATTGA      1620

ACTCCAGACC TTTGGAAGAG CAGTCAGTGC TCTTAACTGC TGAGCCATCT CTCCAGCCCC      1680

GTTTTTTAGG TTTTTGAAGA CAGGGTTTCC TGTGTAGCTC TAGCTGTCCA GGAACTAGCT      1740

CTGTAGACCA GGTTGGCCTC AAATTTAGAG ATTTGCCTGT CTCTCTGCCT CTCGAGAGCT      1800

GGGATTAAAA GTGTGCAGCC CAACAATCTA CTCAAAGTAG GTTTTGAAAA AGCTTTCCAT      1860

ATTAGGAGTT AACTAGCTTC ATTTCAGAAA TACTGCATGG AATTCAAATG TGGGACCATT      1920

CATAGCTACT TTGGTTTTCC TTCAGTGACA GGCATTCGGC ATGCCTATTA GGGAAGTCAA      1980

ATGGCCTGGA GAAGTCATCC TGGGTGAGAG GGCTAATGCA TTTTCAGCTT GACAGACACT      2040

GTCAACCTAT GCAGACAGTC TGCTCCAGCT CAGATGTCAA TTGCATGCAG ACCTGCAGTC      2100

AGACGCTAAG CTCCCTACCT ACTCTCCATC AGCTTAGATG TAAGGGGTGC TGGAACAAAG      2160

GCTCTCTCTC TCTCTCTCTC TCTCTCTCTC TCTCTCTCTT TCTTAGAATT AGTATTCTAT      2220

TTTATTTTAT GTAAATTGGT ACTTCACTTA CATGTATGTC CGTGTGAGGA TGTTGTATCC      2280

TCTGGTACTG GAGTTATAGA CAGCTGTAAG TCGCCATACA GGTGCTGGGA ATTGAACCCT      2340

GATCCTCTGG AAGAATAGTC AGTGCTCTTA ACCCCTGAGC CATCTCTCCA ACCTCTTGCA      2400

TATTGAGGAC AGGGAGGAAT CACAAGCCAT GTAGGGTGCC TGGGCTCTGA GGTCAACAGG      2460

ACCATAGCCT CCTTTCTTTA TGTGCCTTTC TTGGGGTCTC CCTATAGGAG TCGTCTTCGT      2520

TGCCTCTTTA CTGTCTCATT GATCTGGGCT AAACTTATGC AGTTGGAAGG AAAGATCAAG      2580

CTGGTCATGT TTAAAACATG AAACAGCCTC ATCAGTTCCC TTCCTGTTCC CGTCTCCCCC      2640

CCCCCTCCCG CCCCCATTTT GAGAGGACAG GAAGGTAAAA TACCAAAGTG TCCTATTTTC      2700

CTCCAAATAT CAGGCTCAAA GGACTGAAGA GCTGACTTCA GATCCCAAAG CCACTGTGTT      2760

AGGAGGCACC TGCTTTTTAG GTCCTAAGCC TTCCTGAGCC TTGCTATTGG GTATTCTTTA      2820

CCAAGACCCT CAAGGATCTA GGCAAGAACT GGGCAGGATC TGTATGTAGC CCATAGTTAG      2880

ACCTAGGGCA GCTGAGACGC CAAAAGGGAG AGTTTCCTGA GGACAAAAGT GTTCAAACAC      2940

AACTGGGTGC TGGTTGTTGG GCTACTCGTG GAGGTGTGGT GTGTGTAAAG GAGGCTGTTG      3000

AATTCCCAGA AGGCTGGTTC CACAGTGTAG AGTCTACACT GGGGACTTCC CGAGACGCTG      3060

AGCCTCAGAT CTAGCTTCTC AGTCCAGGCC AGCTGATGTG GGGCTGAGGA ACAAGGATGG      3120

ATGCCATCTA TGGCCCTGCC TTGCAGGTGC AAAGGGCCTT TGGCACCATC TACAGATTGA      3180

GGGCAAGACA GGGCTGGTTC TTCCTCCTTG CTCTCGCTGC TATCTGCCTC GCCTGTAGGC      3240

TCTCTGGGCT CCTTTTTGGA CTGACACGTC TGAAGGAGCT TGGAAACTGT GAGGTCCAGG      3300

CCCCATAGAG AATCATGAAG GAACAGGAAT TCAACTGGAG CTCCGCAGCT GGTTAGGCCT      3360

GCGGTCACCT GGAAACAAAG AGGCCATTTA TTTTTTCCTT TGGTCTTGGA CAAGGAAGAG      3420

AAGGGGCTTT CTATAAATAG AAAGACAGCA AAAAGAAAA TAATAATAAT AATAATAATA      3480

ATAATAATAA TAATAAAAAC AATAACAAAG CCAGCTCTTC CAGACAGTGC TCATGTCTTT      3540

AAAGGTCTTT AAAGGTCTGG AGTTCCCAGC AATTAAGTAA AGGACCAAGA CCTCAGGGGT      3600

CCCCTATCCT CAGCCCGTGG GGAGGTGGGA ACCATACATC GATCCCTCGG TTTATATATA      3660

GCCTCATCGC TGTGGGCTC CGAGGTTGCC CCCAAAATCT TGCTCACCTG GAGGACCCCT      3720

GGGTGTCCTC GCCCAGAGGG CGCTGCAGCC TCGCACGTAG AGAACTAACA TCGCCCTTCT      3780

CCAGGGCAGT GCCTCCGGAC TCCGGACCAG GACATAGTAG CGAGTGCACC TGGGTCTCCG      3840

TCAGCTACGC ATCAAGGAAG GTGCGACGCG GGAATTACAG ATTGCCGGCA CTCACCAGTG      3900
```

-continued

| | |
|---|---|
| CTCAGGGGAG GAAGGTGGGA CTCAGACCTG CAAGAGCTGA AGAGTGGGGT GGGCTTCGAT | 3960 |
| CCTAGGAGGC GTGGAAGGGG GTGTGGCTGG ATCCCTGGGG GGTGGGGCGC TCCAAGGGGC | 4020 |
| GGGGCAACCC AGGGGGCGGG GCCCGAGGGG TGGAGATTGG GACTACCCAG GCCCGCGGAG | 4080 |
| CTGGGGGTGG GCGGCTAGTT TTGCAACTGC AGAGCCTTTG GGTTTATTAT AAGGCGGAGC | 4140 |
| TCCGCGGGAG AGGTGCGGGC CAGAGGAGAC AGAGCCTAAC GCAGAGGAAG GGACCTGGCA | 4200 |
| GTCGGGAGCT GACTCCAGCC GGCGAAACCT ACAGCCCTCG CTCGAGAGAG CAGCGAGCTG | 4260 |
| GGCAGGAGCC TGGACAGCA AAGCGCAGAG CAATCAGCAG AGCCGGCCCG GAGCTCCGTG | 4320 |
| CAACCGGCAA CTCGGATCCA CGAAGCCCAC CGAGCTCCCG CCGCCGGTCT GGGCAGC | 4377 |

```
ATG AGA CGC GCG GCG CTC TGG CTC TGG CTC TGC GCG CTG GCG CTG CGC    4425
Met Arg Arg Ala Ala Leu Trp Leu Trp Leu Cys Ala Leu Ala Leu Arg
 1               5                  10                  15

CTG CAG CCT GCC CTC CCG GTGAGTGTGG CCCGGGGCAG GGCTGGGAGG           4473
Leu Gln Pro Ala Leu Pro
            20
```

| | |
|---|---|
| CGGCGGGAAG CCGGGACTCG CCACTCGCCG ATGCCATGCA GGCGGCAGCA CGTGGAGGGG | 4533 |
| GAGGGAGCG GGGACTTCTT CCCGCGCTGC CTGGCGGATC CTGGGATGGT GAGCCCTTTA | 4593 |
| ATGAGGACTC CTGTCCCAAT TCCTCTACGG TCCGTGGATG CCAGGAGGCT ATCCCAGCTC | 4653 |
| GTGGTCCGGG CGTCCTGCAG AGTGGAACCT CCATTGGTTC CCCGCTCCCA ATTAAGTAAA | 4713 |
| ACGACTCCAC AGGGGTCTGA GTCGCCGGCC TTAGGCGCTC CGCCGGCCTT AGGCGCCGCT | 4773 |
| TGGAGTTGCT CTCTCCCGTT GCTGTCTTGC TGGCCATCTC AGCGGCCTGG CCTCCGCCAG | 4833 |
| TGTCCCGGAG GATGCAGTGG CCATGGCCAA ACGCCTTTTC CATAGACCCT AATTCAAACC | 4893 |
| AGACTGCAGG CTGCACCCCC AGCGCCGCGG AGTCCGGGCG CTCGGCCCTT TGCACCGGGG | 4953 |
| CAAGTTTGGG CACAGCAGAG CCGGCGCGGG AACAGGGGGA AGCTGACGTT CGGGGTGGCG | 5013 |
| GGAGGGACGG GATTAAGGCT GTTTGTGGGA CACAAGAGGG TGGCTCAGGG ACTTCGGTTT | 5073 |
| TTCTCTGGCT GCCCCAGGTG AGCCGGGCCG AGCTGGCAGC GGGAGGTTCC GGGAAGTTGG | 5133 |
| CTTCAGAACG CTGAAGACCC TAAGAACCCA ACTTTGGGGT CGCTGAAGTT GTGCTGCCCC | 5193 |
| CGGAGGGCCT CCTCCGCATG GCCCGCGCGG GGGACCCTCC CCGCGAGTGG ACCCCGGTAC | 5253 |
| GGCTCTTCCC CTCCCCCGAC TCGGCTTTGT GCTGAAGCCG CGCGTAGGGA AGGCGGGTCC | 5313 |
| CTTGGCCCGC CCAGTAGGGC CGCGGGAAA GAGGGACGAA CGTGGAGCTG GCGACTGGTG | 5373 |
| GGGGAAGCTT CTGGGTAGGA TGCAGCCATC CACCTTTGGT GGGGTCGGTC TCTCTAATCA | 5433 |
| GCGGCTTGGC GACAAAGAGC TTGGTCGAGG GTACCCCAGA AAGTGCTCTC CGCCCCAAG | 5493 |
| CCGCCGTCGC TAGCCCGCCT TCCCAACGGG CGCTTTGTTC TCGGCCCCTG TAACCCTTCC | 5553 |
| CTGGGAACCG CCCCGCAGCG CTGGTCCTTG ACGTGGGCCG GGTCCTGGGT CGCCGCCAGT | 5613 |
| GTCAGCGCTG CCCTCCGGTG TCCACGCCCC TAGCCCCCGC ACCCGCTGTG AAGTCCCGGG | 5673 |
| TGTCCTTTCC ACTGGCGCTT TGCCCAACCC CTGGAAGGCA GAGGCGAGGT GCGGAGCCTC | 5733 |
| AGGCTTTATC CTCCCGGAAG TGGCAGTCTC CCACCGCCAC ATCTGGTCTG CTTAACTTCG | 5793 |
| ATAGTCCTGG CAAAGGCAGA CACGTGCACA GGGAAGGAGA GTTGAGCGCT GGTAGATACC | 5853 |
| AAGGTCGTGT ACAAATAAAG TGGCACACGA CACGTCCCCA GTCACTGTTA ATGCATTGCC | 5913 |
| TTCGCTCCTT CCCAGGTGGC TGGTGCTCTC CATCACTCTG GAGCCCAAGA GAGGGCCTCC | 5973 |
| ATAATTGTAT TGCCCATGAG TTGGGGTTGT GTGGGGCGC CAAATCAGGG TTCTCTGGGA | 6033 |
| GGGCTATGAA TTCCGAACTG AGTCTCCTGT GCACTCCTGG CTTTAAGGTT CAAGAAATTG | 6093 |
| TTTGAGGGTT GTGGTTTTTG TGGGACTCAG ATTATGCCTG GAATCATAGT TACCACTGTG | 6153 |

```
GAGAAGAAAG TGGAGCTACT TAGCATGCCT CCCCGGCCCG CCTGGCATTA CCTCCGGCTC    6213

TGTTCTCTAG GCCCAACGTG AGGCCTCACT GGGGCAGTAC AGATGCAGTA CTGAATTTCT    6273

TTCCAGCCAG GATCTGGAGA GGTGGTGTTC TCTTCCCTGG TGTCTTTAGA GAGGCAGATA    6333

TTCCTGTGAC CTAAGCCCCT CAAGCACCCA TTAATAATGC TGAGTAGACA ACTAGAGGTG    6393

GCGTTTTCCG GAACTTCCTG TGTGCTGGCC TGGGAGGTTG AACCCTCTAG GAAACAGGTC    6453

TAGGAAGTAG AATTATCTCA ATGGAAGGCT TCCTGGAGGA AGAAGATGAG CTGAGCCCCC    6513

AGGTCACTGT CTGAGCTTTA GGATCAGACT CCCACTTGGA GGCAAGAGTG TTCGTTTTAC    6573

TTTTTTTTTT TAAGTTTAGT TTATTTTCTC TCTAACAGAA AACAAACAAA CAAACAAAAA    6633

AAAACCCCAC ATTGTTTAAA AGTGGGTGCA TAAGAGTGAG GACATATTCA GAGCTTCCCC    6693

TTTTCCTGAA AAATGAAGGC AGCTGGGATT TACTTAAAAT GAGAGCACAT ATCACAATTG    6753

CCAGAGAGCT GGTCCCTTTC TCAGGGCTCC CTAAGCTCCT GTGGGAAGCA GGTCAGACAG    6813

CCCTGGGGAC CAGAGAGATA GGGAGTGCTT TTGGGTGCCT GCCTTTGAAT GGGGAAGGGG    6873

GGGGGAGCTG CTGGGATCAG AGGCTGCTAG CAACTACTCC CCAGAGACTG AAGCAGGTTT    6933

GTCCCTCAGT GTCCTGTGGT CTTCTGTTTC TCCTATATAG AATAGGAGAA ATGGTTATTT    6993

GCTCTGGAAT AGTGACTTGC TATTTGTTCC CTTTCTTTCC TCTCCCTTAC TGTAATCATT    7053

TGGACTAGTA GAGACACTTT CCCCAGGTCT GGCAGAATGG GAGGGAGTGG GGGAGGCCTG    7113

TGCTTGCATG ATGTCACTGC TGGCTTCAGC TCTCCAGGGA GGGTGGAGTT GGTTGTAACC    7173

TACCTGTGGC TCTTGATGGG CCACAATAAA ACCTCATTAA CACACATTGG TAGGGAGAAG    7233

GGACTGGAAA GAATGATGGG AAAGATTGAT GTTTTTCCTT TTTTTTTTTT TTTTTTTTG    7293

GCAGTACTTT CTAGATCTCC CCTCCCCCTT GCTGCAGCAA AATTTTGGAT TCCTGAAGTC    7353

CTTTGAGAAT GTATAATGGT AGCCAGACTT TTTTTTTTTC AGTCAGCTCA AAATTGCCTC    7413

CTTATAAAGT ATCCTTGGTT GTTTTTTGTT GTTGTTGTTG TTGTTGTTTT GTTTTGTTTT    7473

AAGACAAGGT TTCTCTGTAT AGTCCTGGCT GCCCTGGAAC TCAATATGTA GACCAGGCTG    7533

GCCTCAAACT CAAAGAAATC CACCTACTTC TAACTTTCAG TGCTGGGCCT AAAGGTGTAG    7593

GCCACCAAAA GTGCTCAACT TTTACAAAGC AGTCTTACTT TGAGCAGGAT TCTGAAACCC    7653

TTATTTCCTT TCTGTTATCT TCAACAATAC ACTGCTAGGT GTATTTAGTC CCTCATGATG    7713

CTGGGCCTCC TCAAGTGGCG CCAGGTCAAG CAGTCTCCTG GTTTTTGGTG GCTCTGAAGA    7773

AGACTGTGTC CCAGTGACTG GCAGTTTGAA TTCGGAGCTT CTCTTTTCCT TCTCAGTCTT    7833

TGGCAGGCAG AGTGACACTG GTGTGCCCAA GCCTGGAGCT TCTCTGTTTA ATTCTAGTTT    7893

ATTTTCTTTA TCAGACTGAA AAACAAATCA GGTTGGTTAT AATTCTTATA AACACGAAGG    7953

TCTCACCTTT GCGTACGTCT CCGGCTGTGT GGGTCTGATG TCCCTCGGGA ATCTCTGTTG    8013

AGGCTGCTGC AGTGTGTGTG CGTGTAGAAA GGGCAAGGTA GAATGGACAG AAGCGTGCTG    8073

CCCACCCCAC TGTCCTGTTC CTAAATGATG AAGCACTGGC CCGGTGAAGA GCCTAGAGAA    8133

CTCCCTCGGT GGGAGATGCA CACAATGCCA GGAAGCACAC AGGAGCTTGA GTTCCAGCTT    8193

GGCAGTGTCT TCTCTTTGGT GACTTTATCA GCTCCAGCTG CCCTGGACTA ACAAACAAGG    8253

CTAGCTCACT CTCAGTATTG ATAATCGAAG GTCCTTGGTT CTGTTTGAGA CTGATCCTCA    8313

CTCGGTAGCC TTGAACTCTT AGCAATTCTC CTGTCTCAAC TTTCAAAGAG CTGAAATTAC    8373

AGACTCGAGC CACCATATGC GACTGAAACC TTGTTCCTAA TCCTTGACTG TGAACGACTC    8433

TTGGGTTTGG TTCTTTCTCC ATTTCTTTAG TGTATGTTTT AGTTCGCGTC CTACATAATC    8493

TATTGCCCAT ACTTAGAAAC AACAGGTTAG AGACAGCATT GGGTCCAGCA GAGCCTCACA    8553
```

-continued

```
CTGAAGCTCA GTCCTGCCAC TGATTTACCG TGTCAGCTCA AGTGACTCAC TTCCAACTCC    8613
TCTGCTCCCC ATCTGTAGAG TAGACATCAC CATACCTGCT CTTTCTGCCC ACATTCTGTC    8673
ATTAACATGT TCATTTCATA ACGATGGTGC AAAAGTGCTT TGTAAGTAAA GTGCTGGGGA    8733
AATGTTAGCT GTCGATAATG GTTAGGGTTA ACTTTTTATT GAGTGCCTGT TGTGTGTGGG    8793
GTTGGGTGGG GTTTTTTTAG AGGCTTGGTA GTTTTCTTAC TTCTTTCCTA CTTAGCTTTT    8853
CTTCCTAAGC CTTTATGGTA TGTATCATTG CCTGATTGTT TGAGTGTGTG CACTGAGGCA    8913
CGCCTGTGCA TGTTTGAGAG TATGCTTGTG CGTGCTCTCG TGCTCACATA TGTATGGTGT    8973
GAATACACTG TAGAGTGCAG GCCGGCACAC TGGGGCTGGC TGAATCCTGT GAGCCCTGCC    9033
TGGAGTTTGC AGATCTTCCT TGGACACTCC TGCTTGTGAG CATTTTGTGT GGAGTGACTG    9093
TTTAGCTGGC TGTAGCCTAC ATTGTGCCTT TGGGTAAACC CTGAGTATTG GGAAACACCC    9153
TGGGCTGTGG CTGTGTGTGC CCGACGGTTG CTTGGGTACA GCTAAGAACT CTTCATAGAA    9213
AGTTGAGCTC ACATGCTATT AGTATTAACT GAGTGCTAAG GAACCTGTCT TGGGTGGTAC    9273
CTGCTTGCCC TCTCATGCAG TTTATCTTGA GCTTGGCGAA CACACTTACA GATTTAGTAG    9333
AGCTTTTGTC AGCCCTGGGA GGTGGGTTTC GTGGCCACAA GTGGGTAGCT TGGAATCCAA    9393
GACTCCTGGC TTCTAGGTTG CATTCTCCTG TGGTTCTTTC CAAGGGAATG CTAGGGGAAC    9453
ATTTTGGACA TTAGATTATT TCTAGTCCCA AAGCACACAG AACATACTGT TTCCTAATTG    9513
CCTTTTTTTT GTTTTCCTCT CAATCTGGTT TTGAAGTGTT GGGTTTGAAA ATTGCCCCCT    9573
GAGAGCCTGC CCTAGTGTGT GCAGAGGGAA GATAGTGGAA CAGGAAGTCT GTAGAAAGTA    9633
TCTTCCTTTC CAGGACCTTG TGCCCCGGAG CAGAGTCAGC ATGGTGTCAT ATCGCTTTTG    9693
GCTATTCCAG AAGAGATGAG GTTTTAGGTG AGAATGAACC TTTTAGAACC TTCTAGAACC    9753
TTCTGTTGAG TATGACAGGA ATGCCCTGAA TAGGGTCCGA AGTGCATGGC CACTTGTTTG    9813
TCTTTTCCAT AAGCAAGCAG CTTCAGGTAC AGACAATAAG ACTAGGTTCT TGGAGTGAGA    9873
CCCTGCACTT GGTGCCATTT CAGCTCCAGA TGGACACTGG AGGTCCCTAC ACAGCAGGCT    9933
CTGGGATGGC TGGCTTTGCT ATGTACTGTT GCCTGCTCTA CAAGAGCTTC CCAGGTTACT    9993
AGCCTTTGTC GACGCTGGGC TCGCTGGCCA GGCTTGGGCA TTGGAGAAGG GACAACTTGC   10053
CACCTGGCAT AGGCTGTGTG TTTGGAGAGT CAGGAGGTCT GGTGAAGCCC GCAAGTGGAG   10113
GCAAGTTTAG TGGGACTTGA GGAGAGCTCA GTAGGAAATC TCTGGGCTAG TGACAGGCAG   10173
GTGTGGTGGT GGTGGCGAGG TGGCGGGTCT AGATCTCCTT TTAGAGATTT GCCTAGGGAT   10233
CGTCCCTGCT GACTCTGGAA CTCAGAGGCC TCCAGAGGTG TCTCCTCTGG GAGCCTCTCA   10293
AGGGTCTCCC ATCTCCTACT GTTTATGGCT TTGTGGGCTA CCTAATTACA TAGAGAAGAT   10353
ATGTTCCTCT GCCTCCAGCC CTGGAAAGTT CTGCCCAGTG ACTCACCTGA GCCTGCAGCC   10413
ATGTGTGTAC ACAGGCGCTC TCAGGGGCTT CTGTCCTGCT GGCTTCAGCC TTTCTAGCCC   10473
CTGGTGTTCT CGGCAGTGGT AGCATCTGGG AAACCGGGTC ACCTCTTATT TGCAGCTCCC   10533
TCCCTTTCTT GGTGTCTTCC CCCTTTTTAA CTACTGGTCT GATGGCCTTA GACTCATGCT   10593
GAAATTCTCC TTTCTTTTGT CCTAGCCTTG TCTCTGACTT CTTGTGATCC TCTGGGCCTG   10653
TGAAATCCGC TCAGGGGCCT CCATTTCTAA CAGTCACACA CTGGTGGAGA GACCGAGTCC   10713
TGGGATGGTG AAGCTAACCC TGCTGGGCTT CTCAAGCTTC ATTTGGTTTC TCTTTATTCC   10773
TTCTGGAGGT ACTGCCTGCC CCAGGGGAGT CTCAGACTAG ACCACTCTGG AGTTGGAGGT   10833
GGGGCAGGTT TTCAGATCAG TGCCCTTGGC ATTCGTTGTG GGAATGGGGT GGATGGGGCC   10893
TCTGGGCAAG GTCAGGCTGG GGGTGGAGGC CAGGTGATGT TCTCCGCACC CACACCCAGG   10953
```

```
CAGCCTGGCA CCCTCCCCAA GGTCCGCTCA TCAGCAGGAA TGAAAGCAGT GCCGGGCAGG    11013

TTGGGGCAGT GGGCAGGTGG GCGTGTTTAT CGCTGTGCTC ATCAGCTGAG TCACGATGCC    11073

AGGCCCCACA AGTCCTCCCT GGAGGCTCAC CCCACCCACC TTGACCCACC AGCACCCACT    11133

AGCAGGAGGT AGGGCAGGGC AGTGAGACAA GACCAGCCTG GGGGTCTGAG AGGCAAAGGG    11193

GAGTTGTTCA TGACCTGGCT GTGCATGGGG ACTTGTGGGT GTCTCAGATA TCTCTGCTGT    11253

CCAGGAGGAA GCTGTCTTAA GTGCCAACCT GCCTAGAGCC CCTGCTGGGT GCAGGAAATG    11313

CACAAGGGAG AGTGCCCATC CATGGAATAG GCCCATGGAG CTAGACCAGT GACAGTGACA    11373

GTGAAGTCAG CCCCCACCTG TGTCTTCCGA GCCAGCTGGA GGGTTTTTAT CTCAGATTCT    11433

GCGAAACCAT AGAATCTAGT CAGGAGCCTA GACTGCAAAG CAGGCTTCGT TGATGCTTTA    11493

ACTTGCAGGC TTCCTGGGTA TGAGGGATAC TTAGAAAGGT CCCGCAGGTA GGGAGGGCAT    11553

CAGGAAGTAG AAGAGGGCCA GGCACTTCTA TCTCCTGCAT TGCCCCCTTC TCCCATCTCC    11613

AAGGATGGTA AAAAGAACCC TTCCAGTACA CTGACAGAGA GGAAAACCCT TCATCTCACC    11673

CCATTTGGAT CTGTCGTATC AGCATGTGCT GGCCCTGCTT CCATACCAGA GGTGGCTAGA    11733

GATGTTCCCT GGGAATTCAC TGGTTGGGGA CTTGAGTGTA TCAGAGGGGC ACAAAGTAAC    11793

ATTAACTCTG GTATCCTCTG CAGCAAATCG GAGATCCCCT CTCCTAGGCG AGTTCTCAGT    11853

GGATATGGAG GTCAGGTTTG GCTTGTAGG GCCCCAGCAA GAGTCGTTGA TGTCACTCCA    11913

GCTTCTCCCG AGGAAGATGA GGGTGCTGTG TTGGGATCAC ATCTCTCCCT GAATGGCATG    11973

TTGGGGAGGG ATGGAGCCCT TGCTTCTGAC CCCTAAGCTT GGTCTTTAGG TGGCCACAGT    12033

CTCTGGGTTC TGTCCTACCT CCCTGCCCTT GTGTGCTTCA AAGGCATGCT AAAGGGACTC    12093

TCGGCCATTC CGAATGGCAC AGTGTTCCTT CTGTTCTCCC ACCCCAGAA GGAGGCAGGC     12153

CTGGATTGTA GATTCCTAGA AGTAAGTGGC CCTGAGCATG CTGTTGATGA ACCTGGAACC    12213

AGGCAGGCTG GGCATCCTAG GACCTGTCTT TCCATAGAAG TCTGAATCAG CTACCTTTG     12273

GGACTGAGTA AGGGGCTCCT CACATATCAG CTGGCTAGTC CATCTTGGCT GATCTAAACC    12333

ACATTAGGCT GAAGAGAAGC ATGGTGTACA GTCTGGTCCA CCCGAACCAC ATACTGGCTT    12393

TATCAGTTCT CGTATAATTT TGCAGGTAAC TTTTTAGCTC TAAGCCTGTC TCCTCATCTG    12453

TGAAATCGGG TCCCTCATAT CCTGCCTAGA AGGGCTTTTG AAAAGATTAA TGAAGTAGTA    12513

TGCCGAGTGG TTGGGGTTCT CTCCTTGACT GGAGCAAGTC TCTAGGAGTA CTAAGGATAG    12573

CCTGCTGTGT GCAGCACCCC CAGGGACTGT GCCTGAGTAG GAGGGTACAG AGTCTTCATG    12633

TGAATGGCCC TTCTGGTCTT GCCCCGAAGT TAGTGTTGAT GTCATAGAGT CTACAAACAT    12693

GCCTTTTGTC CTTCCTCAGA AGTCCAAGCC TTTCCTGGCA GACCAGACAT TCATCTCCAC    12753

TGAGCCTCTA TGTGAGACTG GCTCCTGGCC TGAGCTGTGT GGGCTGAGCT GGCGAATGGG    12813

AAAACTAGAC ACCTGGGCAC CTGGGTGGGG GCTCGGGACA GCAGTGTTTC AGTTGTAGGC    12873

ACTGTGCCCC TGCCTGGAGC TTCTGACTGA AGGTTACCCT GAGAGGAAGC AGGTTCCCTA    12933

TAGACACTAA CATAGCTGGG TCAGAGTGCA AGGTGGGTGT GCCCCTGCCC TGACCCATTC    12993

AGTGCAAAGG CTGCTCTTCT GGGAGTGAGA GCTCTGACAG GACTGTGATG GCCGAGGGGT    13053

CTCAGAGCAA ACCTGCCTGG CCTCTCCCCA CTCTGATGGA TATGTGCTCT TAAACAAGTG    13113

ACTGTCCACT TTGCCTCAAT TTCAACATCT GTAAGATAGA TAGGGCGTTA TGGTCTGAAA    13173

ATGGTTTTAA AGATTAGTTA GCTAATACAG GGAAAGTGCT CTGACAGGTA CCTGGCACCT    13233

TACTCAACAA GTGGCTGGAG TGCCTGATTT CCTAAGGTCT CGACCTGTCC CTATGCTTCA    13293

AGTGCCCCTA CAGCCTTGGT CAGGCCCTTA GGTTCTCCCA CCCACCGCTG GCCCCAGGAC    13353
```

```
CTAGACTGCT GGACCCTGAC CCCATTTTTC CTTTAAGCCA CCTCTGCGTC AACTCTAAAA    13413

GGCGGTGGAG TTGTTTATCT AGGCTGTGAG GTGTCAGAGA AAGGACCTGG GCCGCTTTGT    13473

TCCTGTGTGG GCTGGGGCCA CTCCAGGAAC TGAGAAACCC ACCCACCTTT TCAAAAACAG    13533

CCTCTTCTCA GAGTCTGGCA CCTCAGCTAG CCACCATGCT GTGGGACCAC TCCCAGCATG    13593

CTCTGCCTTT GGTTTGTTTC CCAGGGGCCT CAGTGCCTTT TAAAGATGCA CAGGCATCTT    13653

TAGTTCAAGG GGAAAGAGGA AATGAAGTGT ATTTGCTGGT GGTGGTATTC CTGTCACTTG    13713

CATTCTCACA GAGGCTAAAG AAATTTGCTC TTTGTATCTT CTAGTCTCTT CTTTATGATC    13773

TTTTCCCATC TGTTGTATCC CAACTGCAGG GCCCCAGTTC TAGAATTAGC CCCTCCCCCA    13833

TAGGAAGCCG ACTTATGCTA TAATGTGAAT GACAAGTATC CTTTAGCCCT TCCCACAGGC    13893

ATTTTAATTT TCAAAAGGGC ATTGCACAAC CGCAGAGACA CTAAGAAGAG AGGTTTGGTG    13953

ATCAGAGTTA CAGCCCCAGC CTCCCAGCTG GTGGCCCGGC TGGTGCAGGT GTGTCGAAAG    14013

CAGTAGTTTC TGCTTCAGTG AAACTTGAGG ATCCTTTATT TAGCCAGTTC AGGGGCGGAA    14073

TGGCCATGCG AAGTCTATGT GTCACAGGTG TCAGGCCCCC ATATCCTGCT GAGTCTAGAA    14133

TCAGCTACGT AGCAGTTTTG GGGGTATTGC CAGACTGGGA GTTTACATCC CAGAAGCGAG    14193

AATGGTGGGG TTCCTATACT GCTCCAGACA GGATCTTTCC CCCAAGTTTG TCAGCCACCT    14253

CTCTTCAAGT CCCTTGGCTC TGACCAGCAA GACGTATCCA AAAGAAACTG AGGAGGCCCT    14313

TCACTTCTTT TTAGGATAGT GTGGGGCCAG CATGGTGGGG GTTGGGAATG GCTTTCTGTC    14373

TCTTCCATCA TCACAGGCTA CTTCCCAGAG ACACTTTGAT TCTGGGCATC TCCAGCAGTC    14433

ACCTGGCCCA CAATGCTTTG CTGCCCTTTG CTTCAGCCAC TGTATCTGGT TGTCCCTTGA    14493

AGGTGAGCCA GAGCTCCTAG GCAGAGAGCA TGTGCTATAC AAAGCCGTAG GCTGGGCCCT    14553

GGGAACCTTC TTGCTGTCAT CCTCCTGTCA AACCCCTATG GTATGGTAGC CCACATAAGG    14613

CTTGTGCAAA AAACAGGCCA AAACATAAGT TATCTTTTCA CTCTATCGGG TCTTCTCATT    14673

TTCCCATGGT ACGTTCGGCT GGCCAGGCCC AAAAGATTTG AAGAGAGGTG GCTGGCAAGT    14733

CTAGGGGAAT AGGTCTATCT GGTTCCCTCC AGGAGCAGTG CCTAGTGAGA GGCTGGGCTG    14793

GGCAGGGCAG GGCCCCTTGC TCCACATTGC CTGAAGTCCC GCCCTGCCCG TCCTGGCTGG    14853

GATCTGGCAG GTCTTCCAGC TCCACACCCG GCTCTCAGCT GAGCCTGCTC AGAGACTAGT    14913

CCTGGCATGT GGGTTGCAGG GCTGGTTCCA GCTCCACCAG GAGGTATGGG CGTCTGGGTA    14973

CTCATGGGAC ATTGACCTGT AGTGGGTATG GAGAGTGGAG GAATGGTACA GGCAGGTGTG    15033

CTGGTGCTGA CGGACTTGAC TCCGGCATTG ACCTTGGCTT GCAGTCTGGT GTTAAACTAA    15093

CAGGGAATGC TGACAAAAAA GACAGTTATT AAAACCAAGA CAGGATACTG CTTTCCCACT    15153

CAGCCCATTC CCAAGAATCC CCAAGACGTA CAGGAAATGT GCAACAGCAG TGGGAATTGC    15213

TGAGTTGGGG GATGTGGGTG AGCTGTGTGC TCCCAGGGAA TTTTGGGAAA TTCCCCTCCG    15273

TTGAAATGCT GTCAGGGTCT GAGCCTTGGA GGTGTTTTTG GGGTGCTGTG CTCCCCAGCT    15333

AAGCAGCTAA CAGTCCTCTT TACCTGCCTT GTCCTCACCT TGCCCCACCC TGGGTTGGGC    15393

CTCTCGTTCA CTCCCTGCTG GGTCACCAGT ACTTCAGTGC AGGTCTCAGC TTGATTCTTG    15453

GTGGAGAGAG AGAAAGTTGA TAAATCAGGG TGCCTGTCAG CCGGAAATTT GGGTGTGTCC    15513

TGAAGGCACC AATGGGGGCC CTCCCTTCTG GAGGTGGCTT TAGGAAGGGG TTTCTGGGTC    15573

TTGAGGCCTC CTTACAGTTT CTTAGCTCCA TGGGAGAGAA GTGAGGAGTT GGGTATCGTC    15633

ACCCCAGCAT GAATCTCTGG TCACCTCTCA GCATGCACTG TCCAGCCTGA TCTTTGAGTG    15693

CCATAAAAGA ACAGAATTAT CCTCTCAGAG CACTTCATTT CCCGCCAGCA CAGTGGGTAC    15753
```

-continued

| | |
|---|---|
| AGAGACAAGC TGCCCAGACT CCCAGCGAGG GACTAGTTGA GCCCCAGCAT GGGACTAGTT | 15813 |
| GAGCTAGACC TGATACAGTC CCAGAGAGCC TCGTTGAGGA AGCTTTGGGA AAATTCACCC | 15873 |
| AGCATTTCAG CCAGGACTGG AGGAAAAGGT GATTATGGGA AAGAGAGCAG TCAAGACCCC | 15933 |
| AGGCTGTAGG ACACAGGATA CAAACTGAGA GCTACCGGAT AGGAGTAGGT TTTAGTCACA | 15993 |
| ATCTCTCCTG TCCGCCCTAC CCTCCAGGAG ACATTGCACC TTGTAGAACA GCTGCCCCGG | 16053 |
| AGTCCACCTT TGGGCCCCCC TGGGTAGCTC AGTAGTGTCA GCATCCTCTC ATTGACATCA | 16113 |
| GTCAGGTTAC ACAGTGGGGC AGCTAATGTG AAGGCGCTAG GCTGGGAAGC CAGCTACTTG | 16173 |
| GGAAAACTAG GTTGTTCCTG GTAGGCCCTA GCAGGAAGGC AGTTCCTCCT TTTCTTGGTG | 16233 |
| GCTTTAGGGG TCTTTGGAAG CTTTGAATGT TCCCTCAGCT CGTTGGTGAA GCAGGCCCTC | 16293 |
| CTGGTACTGT GGTGTTTGTC TTCGAAGAGT GAAGGCATTG GAAGTAAAGA CTGATGGGGC | 16353 |
| GCCTTCCCAG GATGCTTTGC TTCTTGCGCT GGCTTACAGA GCTCTCTTGC TACCTAGTGC | 16413 |
| CTTGACTTTG AACACCAGAT TCAGTCAGGG AACAGGAGTA GAGGTCTTGC CTTGCTGAGC | 16473 |
| CCCTGCGCAC TGCAGGAAAA GACTCCTCTG AGTGGAGCCT TTCCTCCTCA GGTGACTGCT | 16533 |
| TTCAAAGTAC AGCAGCCTCT GAGGGGGAAG TGTCATTTGA CATTGTGGTA GTTCTTGGGG | 16593 |
| TCCCTGGATA CAGATGTCAT GCCCAGATCA TAGGTCTGTT TGTACAGAGG GAGGCGAGTT | 16653 |
| CTGTAGCTCA GAGTCCTCAG TACCCCAGAG TTGTGGCTCT AGGGGTGAGA GGAGAAGACT | 16713 |
| ACAGCCCTTC AATCACAGGT CTGACCTGTG GGTAGGGGTA GATCTCTTGC ATACTATGAA | 16773 |
| CCTGTTTGAA ACCCCTGGGT ATTTGCTGTG GAATAGAGTC TTGGTTGGGT AAGAATGGTG | 16833 |
| GATGTTTATC TTGGTGTGAC TCTCGGGTGG GGGTGGGGGA TATGTCCCTG TCTTTCCCAA | 16893 |
| TGTAGTATGC TGAGTGGACA GAGACCGTGT GACTGAAGCC TGGGCTCCTG GAACAGGTGT | 16953 |
| GTGTTGGTGG GGGGTGGGGC GCAACTATCT GGGATCCAGA CTGCTTGGGA ATGGCTGTGA | 17013 |
| CCCAGCTCCT TTGATAACAG CAGCTCTTTG TCACTGGATG TTGTGACTAA TGGGACTTGT | 17073 |
| TGATTCAGTT ACTCGGCTCC CACCCACAGA CGCCGGGGCT TCTGTTGTGG CACCAGGCAG | 17133 |
| CTGCAGACGC CCCACAAGTT TGCCTCGCTT TCCCACTCCA CGAAGGTAAG TTCCCAGCAC | 17193 |
| TGCCCAAATT AGAGACTTGT GAGTGGTCCC CTCATACCCC ACTCCCTGAG GCTTCTCCTG | 17253 |
| GAAGGCCTGG AATGGGGCAC TGGGTGTGTA CGTGCTGTGG TTTCTGTTAG GGTCAAGACC | 17313 |
| AGGCTGTTTC TTACCTGGCT CGTACCTCCA AGTTTCCAGG TGATGAGTCC TGATTTTTGA | 17373 |
| AGTGAAGGAA TCCATTTAAT ATCAAAATTC TGTGACCTTA AATTTTTTTC TTTTATTATG | 17433 |
| TGTCATTTCA TATGTACGCA TATTTTTTTG TCTGTGTGTG GACATGCTTG TGGCGATCAG | 17493 |
| AGGACACTTC AGAAAGTCAG TTCTCTCCTG CCGTGTGGGT CCTGGGGAAT CAAATCCAAG | 17553 |
| TTGTCAGGCT TTATCCTGAA AATAAAAAGT AGACAGCCCT TGGGATCCAA AGCTTCTTAG | 17613 |
| GGCTGTGTGT CTTAGACACC ACCAGTGTTG CACAGCTGGT AACATGACAG TGTCCTGGAG | 17673 |
| TGCTGATTGG AAGCCACAGG CCTCTGTGCA GGGCGGTAGA CTTCCAGGGT ACGGGCAGG | 17733 |
| TGGGCGTTCT CTACAAAAAC CTTGTAATCG CGGACGTCTT GGAGATGCCC CCTAGGTATC | 17793 |
| ATGATTTTGG TGTGTGACAC AGCTGAACTG TCTTCATACT CAGGATATCA TGAAGTGCTG | 17853 |
| GGGTGCAGAC CACTCTCAGC CTCAGGCAGC CAGGACCCGG GGCTCCATCA GATTGCGGTG | 17913 |
| ACTACCACAG AGGGTGGCCT TCCTTCCGGT CAGTGTGGGT GTGGGAGCTG GCAGGAAGTG | 17973 |
| GCTCCAGGCT TCCTTTAAGC ATCCTCTGCC CACAGCCCCA AACATGTTCT TTGGCAATGG | 18033 |
| CTTGCAACTA GAGGTGAACT CTCTCCTGTA CTATGTCCTG ACCCACGCTG CTGCATCTAT | 18093 |
| TATACCTTTC ACACGCGTGA TGGGTACCCA GCGGGGCTGC TAGGCAGGGT TAAGCACTCA | 18153 |

```
TCTTGTTTCC TGGTGCTGAA GCTGTGGTAA AGAAACTGAG GCCATTTTCC CTTGAGAGAG    18213
ATGGTCTCAG CCAGGTCTTT CTCGGCCTGG GGAGCCCGGA AGAAAGGATG TACTACAGTG    18273
AGTGGACACT TGTTGGCTGA TGGCCTTGGT AGGTCCTTCA CCCTGGGAAG TGCTGTTTCT    18333
TATCTGTTAG AGATGCTGAC CTCAGCAGGA CTGGAGGAAC TGCATGGGAG GTGTAGGAAT    18393
GAAAGTGAGT GGGGAAAATT ATCTCCAGCC CTAGGGAAGT CTGAGGCCTG TGTCCCCTTT    18453
GTCCTGGACT GGGCCCCTGC CTTGGGTGTC TGTCCAGGGT CTTTGCTCTA CAGCCCCAGC    18513
GGATGCCCAA AGTAGACGAG TCAACTGGTC CTTTCTTTCA CCCTGTGTCC ACTTCTCATG    18573
TATCTACCTT CATAATCCTT CTAGGTAAAA CAAGCCTCTA ACTTTGGGTT TTCAAATCAG    18633
CCAGCTTCCA GGCTCGATAG TACGAACCAT GAAAATCTTT CTTACCATGA GGTTGTTTTC    18693
TAGTGTGTGT GTGTGTGTGT GTGTGTGTGT GTGTGTGTGT GTGTGTGTAC GTACACATAT    18753
GTACCTCTAT CAGTGTGCTG TGCGTGTACC ACAGCAGACT CGTGAGGAGG TCAGGCAAAC    18813
TTTATAAAAA TCTTTTTTTT TTGCTTCACT TGAGTCCCAG GGTCACACAG TGGCAAGTGC    18873
TGAGCTCTGT TCTCTGTTCT TGATTTGTTT TGTGAGCAGC TGATGTTCTT AAGGCTTGCG    18933
GAGGGGAAAG GTAGGGCTGG CTTGCTTCTT CCCCGAGTGG CGGTCAATCC CTAGACATCT    18993
CTAAGCCGTG GCCACACGTC CTGGAAGGAC CCAGGTCAGA AGTGATACTG AGATGGCCCT    19053
GTGAGCCCTC TCGAACACAC AGGGTTGTAA ATAGTACCTG ATTGTTACAT GGAGACTCG    19113
TCAGCTGGGT GGAGTCCTGG TTCAGAGGGA GTTATTCCTC CCCCCACATT TCTTCTCTTC    19173
TGGGGCTGAA GTCTCTTCCT TCCTTACCTG TGATGCTGTC ATGATAGGTC CCAGCTGAGA    19233
GTGGAGGCGG GGCAGTCAGG GAGCTGCTTC TCTTTGCTTA GCAGGGGTTG GAGACTTGGG    19293
GTGTAGGGGT TGGCTCCCCC TTTCCCTGCC CTGGACCTGG TTTCTGGTTT CAGCAGAGAT    19353
TCGTTCTAGA AACTTGTTGC GTAAACAAGA TCACAAAGCG ATAAGCTTGA GCAAAACCCA    19413
GGGGAACAAA TTGCTTCCCT GTGAAGACCC AATCTTAGCT CTTAGAGAAG CCCTCCCTTT    19473
TGGAAATTGC TGACTTTCAG GGCTTCTCTG TGGAGGAAAG AGGCTAGCCG CCGTATGTTT    19533
GCCTGGATTC CAATAAATCT TTGCGGCCTT GGCTACCCCT TGTTGAACAA GGTCTGCACT    19593
CCTAATGCGT GCCTCAGGTG GTCTGAGACC TCTACCCCAT CTCCAGCTTT TCCTTCCTAT    19653
GGAGGGAGTC AGTGGGTTAG GAGAGAATGG AGTTGAGTCC TGGAATGAGG AGGAAGCTAT    19713
GAACTCGGGG CCTGTTCCTG TCTGGTGGGT GCTCTTCTCC GCCGCTGAAG GAGGCAGCCG    19773
CAGGGAAGAC TACCACAGGA ATCCGAGTAC CACCTGGAGC AGTGTATACA GGATGTGGGC    19833
TGATGTGTGG TAAGGGCATG ATGGGCTGAT GTGTGGTAAG GGCATGGGAT CTGATTGCTC    19893
TGTGGATGGC CCACAGGGAA ATTTTTGAGT GTCTACTGCA GTAGTTCTCA ACCTGTGGGT    19953
TGTGCGCCCC TTGGTGGGAG TTACATATTA GATATTTACA TTATGATTCA TAACTGTAGC    20013
AAAATTACAA TTGTGAAAGA ACCAAGAAAT CACCGCAGCA TGAGAACCTG TATTAAAGGG    20073
TCACGGTGTT AGGAGGGTTG AGAGCCACTC ATCCTCTGGG TCTAGGCCAT GGCGGGCTGT    20133
AACTGCTCTC TGGAGTTAAG CCACAGTGAA CCAGCTGTCC TTGCAGATGG ACTTGTGGAG    20193
GCTCCAAACC TTTGTCCCAG GGGAGAAGAG CTTGCTTTTG CTTTGTACTT TTAAAGGAAG    20253
TTCAGTGGTC TTCGGGCCTT GTGGCTGCTG TGTGTGGAAG TGCCCCTGTA CAATAAGCTG    20313
TATAGATCGT GTACAACTGC AGTTTTCCTC CGTGGGTCCA CCAACCACTC CTGACTCCAC    20373
GGATGAGTGA GGCCAGTAGG GCTGTGTGTG GGTCCCTAGG CCAAGCATCC TGGACCACGA    20433
TGAGCCTCAG CTAGACCACT CTGGATCTTT AGCAGAGGCT CCTAGAGAGC TGGCTGGCTT    20493
CCTCCTGCCT TCTTTTCTCT TAAAACTTCG TCTCAATCGG AAGCTCCTCT GTGCACGTGA    20553
```

```
CCTCCAGGCC TGGGGTCGC CACAAATCCC CTCATCACAA GACGAGCAGC TCGCATGAGG      20613

GACACGACAC TTGTTACCTA CCAGGCTGTG GGGTTTTTGT TGGTTGGTTG TTTTGTTTTG      20673

TTTTGTTTTT TTACTTGTAC AGAAGTGTTG TGACATCAGA TGTCAGCTGT TAGTGCTGGC      20733

ACCATTTTAC AGGTAGGGAA CTGAGGCTGT AAGATGTGTA GTGACATCGC TAAGGCCACT      20793

CAGTTGGTGA GGCCTTACCA AGGTCAGGTC TTTGGAGCCT TTTGCTGAAC CATGTACTTC      20853

TATCTCTGTT TTGTTGAAAC AAAGTCTATA TGGCTCTGGC TAGCCTATAA CCCCATATGT      20913

AGACGAGGCT GACCTCGAAT ACACTGCAGT CTTTTATGTC TGCCTTCTGG GTGGCAGGAT      20973

TGAAGGCATG TGATTCCTCC TAACTGTACA CTTTAAAAAA AAAATCATTC TTTGTTCTGG      21033

TCTGTGCCAG GGCCTTGTAA GATGTTCTGT GCTGAGCTGG GCTATTTGGG TTAGTCTCAT      21093

TGCTGAGCAG GGCCCCTGTA TCTTCCTTCT CTGTCACTTG CTTACCTGGG TCTTCCTCCT      21153

GCACTAGCTA TCCTAGAACC AGTACTGAGA GCAACTATGG GCCCAACTCT GCCCCTTGCC      21213

CAGCCTGCTT AGCTGGGGGC GGTGTTCCAC TTCCCTGCCC AAGTCCTGTG GGACTGTGTT      21273

TGTACTCCAC CACCTTCAGT TCCTTGGAGC TGGAGCAGGC CAGGCGGCTG CATTCCTGCA      21333

GCTGCTGTTG CCAGGGAGAG CCCATCCCAT TCACTTCAGT CTCCTTAATG TAGAAGCCTT      21393

GTCGAATTAG CTTCCACTGT CCCCAACCCA AGAGTACCCT GTCCTTTCTT CACTAAGAAG      21453

GCCAGGATAC AGTCCTTCCT GTGGCTGATA AGACAGGCCT TGGGACAAGG CCTGGGACCA      21513

CACTGTGTGG GCAAAGCTGC TTCAGCACCG ATGGCTCCTC CATGCCAAGC TTGGCTCTGC      21573

TTCTCACAGT TGAGACTTCT GTGCGCACAC CCACTGTCTA GCTCAGCTGG ACACTGATTT      21633

TCTTTAAATG TATAGATTTT GGGGTGGGGT GTGCTGAAAG CTCCCACTGA TGCCCCAAGC      21693

CTGAGTCTCA GAGTATGATC AATTGATGGC TTTCATGGGT ATCACAGCTT CTGTTCCCAG      21753

GTCAGACTCC CTGACCAGTC AGAGCATCCT GGGGTTAGAC AATGTCCCCG TCACTTGTGC      21813

CTCCACCTGG CACCAGGCTA TGATGTTATG GCATTGAGGG TATGAGAAGG ACCAGGGGTT      21873

TCCCAGAGTT ACGCCCAGGC GCACAGGCAA TTGTTTCCTA CATGTGTGGC TGGAATGGTT      21933

GGGTGAGCCT TTTCAGCTGC CTACAATAGG AACCCAGGGA TACTGGGCAT TGACCAAGGC      21993

ATATCTCATA CCCTTTTCTT ATCTTTCTGC AG CAA ATT GTG GCT GTA AAT GTT        22046
                                     Gln Ile Val Ala Val Asn Val
                                                      25

CCT CCT GAA GAT CAG GAT GGC TCT GGG GAT GAC TCT GAC AAC TTC TCT        22094
Pro Pro Glu Asp Gln Asp Gly Ser Gly Asp Asp Ser Asp Asn Phe Ser
 30              35                  40                  45

GGC TCT GGC ACA GGTAAGACTG ACCCAGAACA CTGAGATGGC ATAGATCATG            22146
Gly Ser Gly Thr

GCTGGAGTGG TGAGCAGGCA GTCACCCAGC TTTTAGTGAA CCCCCTTCTT CTCCCATCCC      22206

ATCCTTAGCC ATTGGAGTCA GGACAGTGCC AAAAGGAAGA ATGGTATCCA GCTGCAAGCC      22266

ACTCAGCTAA GAGAAACTCT CAGAGAAATG AAGGGGTTCC ACCAGGCCAT GGGCAGCCAC      22326

TAGAGCCAAC CCTTGGAGGA GTTTGACTCC ACTGAGCCTT GGTGTGGTGT TTCCATCTGT      22386

GAGATGGGAA TACTTTGCCC AAGAGCCTGT TAGAAGCTGT AGGAAGCACA GAGTCGGCTA      22446

GGTATAGATT TGCTCTCACC TCCATCTCTC GATACCAGTT CTCTGCAGAG CTTGGGTTTG      22506

TGGGAGGGGT GGGGGGGTGA GGGGAGAAGG CTGTGAGCTG CAGCTAGCCA GAGGGGTCTC      22566

CCAGAAGAAT GGGGAGAGCT AAGAAGGAAA GTTGAGGTCA CAGTGGGAAG GAGACCAGAG      22626

CAAAGGGTTG GAAGGTAGGT AAAATGCAGC CGTGTATTCT TGGGAGCCTT AGGCCTTGGG      22686

CAAGAGGGTA GAAGAGGTGT TTGTCCTGGG CTGCAGTCCT GTATCAGCTC TGGTGTCTTG      22746

GCCCACGCTC ACAGCAGGAT CCCTTCCCAG ATTCCCGAGA ATTTCTCACA GTTCAGAGAG      22806
```

```
CACGCTACTT GTAGGCAGGT GAGGCTGCAA AGGACAGCTT TTCTGGCCTA ATTTTCAAAG    22866

TGAGTTCAGC CTTTGCTAGG TCACCTTTGG GGTCTCAGAA GGCTTCAGCT CCTGGTAGAG    22926

CATGAATCAC GTCAGGCGTG ATGCTGGAGA CCTCTCCTAC CCTGACACCC CAAACCCCCA    22986

CCTCTGACCC TGCA GGT GCT TTG CCA GAT ACT TTG TCA CGG CAG ACA CCT      23036
            Gly Ala Leu Pro Asp Thr Leu Ser Arg Gln Thr Pro
             50              55                  60

TCC ACT TGG AAG GAC GTG TGG CTG TTG ACA GCC ACG CCC ACA GCT CCA      23084
Ser Thr Trp Lys Asp Val Trp Leu Leu Thr Ala Thr Pro Thr Ala Pro
                65              70                  75

GAG CCC ACC AGC AGC AAC ACC GAG ACT GCT TTT ACC TCT GTC CTG CCA      23132
Glu Pro Thr Ser Ser Asn Thr Glu Thr Ala Phe Thr Ser Val Leu Pro
             80              85                  90

GCC GGA GAG AAG CCC GAG GAG GGA GAG CCT GTG CTC CAT GTA GAA GCA      23180
Ala Gly Glu Lys Pro Glu Glu Gly Glu Pro Val Leu His Val Glu Ala
         95             100                 105

GAG CCT GGC TTC ACT GCT CGG GAC AAG GAA AAG GAG GTC ACC ACC AGG      23228
Glu Pro Gly Phe Thr Ala Arg Asp Lys Glu Lys Glu Val Thr Thr Arg
110             115                 120                 125

CCC AGG GAG ACC GTG CAG CTC CCC ATC ACC CAA CGG GCC TCA ACA GTC      23276
Pro Arg Glu Thr Val Gln Leu Pro Ile Thr Gln Arg Ala Ser Thr Val
             130                 135                 140

AGA GTC ACC ACA GCC CAG GCA GCT GTC ACA TCT CAT CCG CAC GGG GGC      23324
Arg Val Thr Thr Ala Gln Ala Ala Val Thr Ser His Pro His Gly Gly
             145                 150                 155

ATG CAA CCT GGC CTC CAT GAG ACC TCG GCT CCC ACA GCA CCT GGT CAA      23372
Met Gln Pro Gly Leu His Glu Thr Ser Ala Pro Thr Ala Pro Gly Gln
             160                 165                 170

CCT GAC CAT CAG CCT CCA CGT GTG GAG GGT GGC GGC ACT TCT GTC ATC      23420
Pro Asp His Gln Pro Pro Arg Val Glu Gly Gly Gly Thr Ser Val Ile
        175                 180                 185

AAA GAG GTT GTC GAG GAT GGA ACT GCC AAT CAG CTT CCC GCA GGA GAG      23468
Lys Glu Val Val Glu Asp Gly Thr Ala Asn Gln Leu Pro Ala Gly Glu
190                 195                 200                 205

GGC TCT GGA GAA CAA GTGAGTGGCT TTGCATTTCC TGGGTGGCCA CTAGTGCCTG      23523
Gly Ser Gly Glu Gln
             210

CACCTGGCCG CCTAATGTCC TCATTACAGT GACAGGTGAC AGGGTCCCAC CTTCCTCCTG    23583

CCCGAAACAG ACTGATTGCA AGATCAGGAG GTGGGCGACT CCTTAGATGT CATTCAGGAG    23643

CTTACAGCAG GGTGAATTTT CCGTCTTAGA CCTTCATGGG AATTTTCACA CAACAATGTG    23703

TACGTTGTGT CACTGGAGGC GGTATCTGTG TCTTGGCCTG CCAGGGTCCC AGGTGTGACT    23763

GACTGCATTC CTTGACAGAT GCTGGTATAG GTTGGCTACG TCTGATGGGG GTGGCAGGGG    23823

ATCCCATCAG GTATGGCACT GCTCAGGTTG CTGTTGTGTC AGTGGCTCCA GCTGACCTGA    23883

TCCCAACCTA CCCTTCTGTA G GAC TTC ACC TTT GAA ACA TCT GGG GAG AAC      23934
                        Asp Phe Thr Phe Glu Thr Ser Gly Glu Asn
                                        215                 220

ACA GCT GTG GCT GCC GTA GAG CCC GGC CTG CGG AAT CAG CCC CCG GTG      23982
Thr Ala Val Ala Ala Val Glu Pro Gly Leu Arg Asn Gln Pro Pro Val
             225                 230                 235

GAC GAA GGA GCC ACA GGT GCT TCT CAG AGC CTT TTG GAC AGG AAG GAA      24030
Asp Glu Gly Ala Thr Gly Ala Ser Gln Ser Leu Leu Asp Arg Lys Glu
             240                 245                 250

GTG CTG GGA GGTGAGTCTT CTTTCAGGTG GAGAGGAGGA GGCAGGTGGT              24079
Val Leu Gly
        255

GGCTCTGAGG TAGCCTGGGT TGCTGGGGTG AAGCATCTTT AGCAGCAGGG TGGGGAAGGA    24139
```

```
GGAGGGTCAA TTCTACTCCA GGCCACCTCC TAGGCTGTCC GTCTAGTCTG GGAGAGACTA   24199

CCACTGACCC CGTGGAGCTA CTGATCTGAG CCTGCCTCTG TTCACTCCCT A GGT GTC    24256
                                                        Gly Val

ATT GCC GGA GGC CTA GTG GGC CTC ATC TTT GCT GTG TGC CTG GTG GCT    24304
Ile Ala Gly Gly Leu Val Gly Leu Ile Phe Ala Val Cys Leu Val Ala
        260                 265                 270

TTC ATG CTG TAC CGG ATG AAG AAG AAG GAC GAA GGC AGC TAC TCC TTG    24352
Phe Met Leu Tyr Arg Met Lys Lys Lys Asp Glu Gly Ser Tyr Ser Leu
        275                 280                 285

GAG GAG CCC AAA CAA GCC AAT GGC GGT GCC TAC CAG AAA CCC ACC AAG    24400
Glu Glu Pro Lys Gln Ala Asn Gly Gly Ala Tyr Gln Lys Pro Thr Lys
290             295                 300                 305

CAG GAG GAG TTC TAC GCC TGATGGGAA ATAGTTCTTT CTCCCCCCAC             24448
Gln Glu Glu Phe Tyr Ala
                310

AGCCCCTGCC ACTCACTAGG CTCCCACTTG CCTCTTCTGT GAAAAACTTC AAGCCCTGGC   24508

CTCCCCACCA CTGGGTCATG TCCTCTGCAC CCAGGCCCTT CCAGCTGTTC CTGCCCGAGC   24568

GGTCCCAGGG TGTGCTGGGA ACTGATTCCC CTCCTTTGAC TTCTGCCTAG AAGCTTGGGT   24628

GCAAAGGGTT TCTTGCATCT GATCTTTCTA CCACAACCAC ACCTGTTGTC CACTCTTCTG   24688

ACTTGGTTTC TCCAAATGGG AGGAGACCCA GCTCTGGACA GAAAGGGGAC CCGACTCTTT   24748

GGACCTAGAT GGCCTATTGC GGCTGGAGGA TCCTGAGGAC AGGAGAGGGG CTTCGGCTGA   24808

CCAGCCATAG CACTTACCCA TAGAGACCGC TAGGTTGGCC GTGCTGTGGT GGGGGATGGA   24868

GGCCTGAGCT CCTTGGAATC CACTTTTCAT TGTGGGGAGG TCTACTTTAG ACAACTTGGT   24928

TTGCACATA TTTTCTCTAA TTTCTCTGTT CAGAGCCCCA GCAGACCTTA TTACTGGGGT    24988

AAGGCAAGTC TGTTGACTGG TGTCCCTCAC CTCGCTTCCC TAATCTACAT TCAGGAGACC   25048

GAATCGGGGG TTAATAAGAC TTTTTTTGTT TTTTGTTTTT GTTTTAACC TAGAAGAACC    25108

AAATCTGGAC GGCAAAACGT AGGCTTAGTT TGTGTGTTGT CTCTGAGTTT GTCGCTCATG   25168

CGTACAACAG GGTATGGACT ATCTGTATGG TGCCCCATTT TTGGCGGCCC GTAAGTAGGC   25228

TGGCTAGTCC AGGATACTGT GGAATAGCCA CCTCTTGACC AGTCATGCCT GTGTGCATGG   25288

ACTCAGGGCC ACGGCCTTGG CCTGGGCCAC CGTGACATTG AAAGAGCCTG TGTGAGAACT   25348

TACTCGAAGT TCACAGTCTA GGAGTGGAGG GGAGGAGACT GTAGAGTTTT GGGGGAGGGG   25408

TGGCAAGGGT GCCCAAGCGT CTCCCACCTT TGGTACCATC TCTAGTCATC CTTCCTCCCG   25468

GAAGTTGACA AGACACATCT TGAGTATGGC TGGCACTGGT TCCTCCATCA AGAACCAAGT   25528

TCACCTTCAG CTCCTGTGGC CCCGCCCCCA GGCTGGAGTC AGAAATGTTT CCCAAAGAGT   25588

GAGTCTTTTG CTTTTGGCAA AACGCTACTT AATCCAATGG GTTCTGTACA GTAGATTTTG   25648

CAGATGTAAT AAACTTTAAT ATAAAGGAGT CCTATGAACT CTACTGCTTC TGCTTCTTCT   25708

TCTCTGGACT GGTGGTATAG ATATAGCCAC CCTTTGCCCA AACCCTGGTA GCTCGGGGAA   25768

GCTTGGCTTA AGGCTGCACG CCTCCAATCC CCCAAAGGTA GGATCCTGGC TGGGTCCAGG   25828

GTTCCTCTGA TTTATTTGGT TTTGTTGTGT TGTGTTGTGT TTTTCTTTTG GCTAAACTTC   25888

TTTTGGAAGT TGGTAAGTTC AGCCAAGGTT TTACAGGCCC TGATGTCTGT TCTTCTAAAT   25948

GGTTTAAGTA ATTGGGACTC TAGCACATCT TGACCTAGGG TCACTAGAGC TAAGCTTGCT   26008

TTGCAGGGCA GACACCTGGG ACAGCCTTCC TCCCTCATGT TTGCTGGGAC ACTGCTGAGC   26068

ACCCCTTGCT TACTTAGCTC AGTGATGTTC CAGCTCCTGG CTAGGCTGCT CAGCCACTCA   26128

GCTAGACAAA AGATCTGTGC CCTGTGTTTC ATCCCAGAGC TTGTTGCCAG ATCACATGGC   26188
```

```
TGGATGTGAT GTGGGGTGGG GGTGGGGTCA TATCTGAGAC AGCCCTCAGC TGAGGGCTTG    26248

TGGGACAGTG TCAAGCCTCA GGCTGGCGCT CATTCATATA ATTGCAATAA ATGGTACGTG    26308

TCCATTTGGA CAGCAGACAC TTTGGTGTAC TTGTGCAGTC TCTTTTTGGT CTGGACCATG    26368

TCCAACTCTA TCTGGTTTTT GGAATGGGAG CCTAACTGGC CTGTGTTCTG GCTTGGTACC    26428

AAATAGCAAC AGTCAGTGGC ATCCTTGCCC AGGCCCCAGG GCAGGACTAT GCTCTTGCCA    26488

TATCCAGGAC TCCCGACTTT GCACCTGTTT TCCCTCTGTG TGTAGCATCA TGAACTCCAG    26548

CTAGGTTGTT CCTTTCCCTG GGGTCAGGAG GATTCTGCTG ACTCTGAATG TCAGGATTTG    26608

CTTTTGTTCT GTTTGCTTAT TGGGCAATTC TCAACCTTCA CTAGCAACAG TCTCATGTGT    26668

CAGGATTACA AGTATTGCTT GCACATTGAG GG                                 26700
```

(2) INFORMATION FOR SEQ ID NO:2:

(i) SEQUENCE CHARACTERISTICS:
        (A) LENGTH: 311 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Arg Ala Ala Leu Trp Leu Trp Leu Cys Ala Leu Ala Leu Arg
 1               5                  10                  15

Leu Gln Pro Ala Leu Pro Gln Ile Val Ala Val Asn Val Pro Pro Glu
            20                  25                  30

Asp Gln Asp Gly Ser Gly Asp Ser Asp Asn Phe Ser Gly Ser Gly
        35                  40                  45

Thr Gly Ala Leu Pro Asp Thr Leu Ser Arg Gln Thr Pro Ser Thr Trp
    50                  55                  60

Lys Asp Val Trp Leu Leu Thr Ala Thr Pro Ala Pro Glu Pro Thr
65                  70                  75                  80

Ser Ser Asn Thr Glu Thr Ala Phe Thr Ser Val Leu Pro Ala Gly Glu
                85                  90                  95

Lys Pro Glu Glu Gly Glu Pro Val Leu His Val Glu Ala Glu Pro Gly
            100                 105                 110

Phe Thr Ala Arg Asp Lys Glu Lys Glu Val Thr Thr Arg Pro Arg Glu
        115                 120                 125

Thr Val Gln Leu Pro Ile Thr Gln Arg Ala Ser Thr Val Arg Val Thr
    130                 135                 140

Thr Ala Gln Ala Ala Val Thr Ser His Pro His Gly Gly Met Gln Pro
145                 150                 155                 160

Gly Leu His Glu Thr Ser Ala Pro Thr Ala Pro Gly Gln Pro Asp His
                165                 170                 175

Gln Pro Pro Arg Val Glu Gly Gly Gly Thr Ser Val Ile Lys Glu Val
            180                 185                 190

Val Glu Asp Gly Thr Ala Asn Gln Leu Pro Ala Gly Glu Gly Ser Gly
        195                 200                 205

Glu Gln Asp Phe Thr Phe Glu Thr Ser Gly Glu Asn Thr Ala Val Ala
    210                 215                 220

Ala Val Glu Pro Gly Leu Arg Asn Gln Pro Pro Val Asp Glu Gly Ala
225                 230                 235                 240

Thr Gly Ala Ser Gln Ser Leu Leu Asp Arg Lys Glu Val Leu Gly Gly
                245                 250                 255

Val Ile Ala Gly Gly Leu Val Gly Leu Ile Phe Ala Val Cys Leu Val
            260                 265                 270
```

```
Ala Phe Met Leu Tyr Arg Met Lys Lys Lys Asp Glu Gly Ser Tyr Ser
        275                 280                 285

Leu Glu Glu Pro Lys Gln Ala Asn Gly Gly Ala Tyr Gln Lys Pro Thr
        290                 295                 300

Lys Gln Glu Glu Phe Tyr Ala
305                 310

(2) INFORMATION FOR SEQ ID NO:3:

(i) SEQUENCE CHARACTERISTICS:
        (A) LENGTH: 2196 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

TCTAGAACAC TTATTAAGAG CCAGGCACTG AAAAGTGCAG ACTCCCTCAT TTCATCCTGG      60

CCGTGCTTAC AAGTAGTTTC CATGCTCTGG TAACCCTGTG CAGAGGGCAG CGTGGGAGGC     120

GGGCCGCTTG GTGGACGGTC ATGGGGCTC TGCATGGGTG GTTGCCCTTG CCTCAGAAGA     180

ACTCCCTAAG TAAGAGCAAG TTAGCCTCCC TAACCCCTGG TGGGTTGTTG CTTCTTTTCT    240

CCTCTTGTTT CTGCCAAGAG AGGGTGGACC AAGAAGACCC CAGCCTACAG AACATGTGAT    300

CCAAATAAAC TTCTTTTTAG TATAAATGTC CTAGCCTGTG ACGTTCTGGT AGACTAGCAC    360

AAGATGGACC AAGACAACTC TCATCGAGAC TCTGAGGAAC GAACTGGCAT ACATGGGAA     420

CAGGAAATGA AGCTTAGAGA GAGGTTCTGT GGCTTGTCCA ACATGGCTGT AGTTTAAATC    480

CAGCTTGCCA CCAAAGCACA CACATTTCAC TGCTGTGCTG GGCCGGGCCT CAGATCCCAG    540

GGGCTCCGGA GCTAGAAGGA CACGTGTATC AGCCATGGCT TCAGTTTATT GCTGTATACT    600

CTGTGCTTCT GGCTCTCATG GAAAAGACAG ACATTGGGGT TCTTATAATC TCTCCCTCTC    660

CCCTCCCCAC ACTCTATCCC CAAAGGAGGC ACCACTTCTG CAGGTAAATG TTATCTTCAA    720

AGCGCTCACA TCGCAACCTT TGCCCACACC ATCTCATTAA AGGAATTGGC AGTGACTTTA    780

AGGTGAAAGA ACTCGGTGGC TACGTGTTAT ATAAATTTGC ATCTGGGTCT CAGAGCTGGA    840

AGGAAGGCAC TCCCATACAT GCAGTCTGTA CATGCAGTCG GATGATGGAC CAACAACACA    900

TTGTGATTTA TGCCCCTGCT GGTGAGCCCA GGAATCCCTG TAGCACTCTC TCTCAGCTCT    960

AGGGCCCTGC TTGTGTATGG AAAACGCTTA GTGTTTTATA GGTATTTTGT CAGAATACTT   1020

TAAGGAACTT GACCAAAGTT ACAGGGAGGT TAGACAGATT GTCATGGTAT ACTCACCTCT   1080

GTCTCTGACC CTCCTAACTG GGACCTCTTT AGTCTCCCTT GAGGCAGGGA GTGCCACATG   1140

CATGTGTCCA GGCACATGTC TCCTGGTTTA CCTCCCAACG CACCTCAAGT CCCCAAGGTA   1200

GGTAGGCACT TGTATTCTGT AATTCAGAGA GGCAAATCAA ACTGTTACAA TGTTTGCCCA   1260

AAGCTCCCCA AGCAAAGTGG CCCTAAGAGT GAGCAAAGAG ACTGCGTGCC TTCACTGCCT   1320

GTGTGAATCC CTGCAGATAG TCTCTCATCT TGGTGCCCTT CCCACAGAGG CTGGGCGGC    1380

AGGAGGGAGC CTGGACAGCT CAGACACTGG GTCATTGATG ACTGTTGTGT GGGATACCTG   1440

CCGGGGCGCA GGAGTGAGCC ATGCCACCCC AGGAAGTGGT TCAGGGTGAC TCTTCTTGGC   1500

ACACCTGGGA GGATGTAGCT GGTGCTGGCA CACCCACCGT CACGAGAGCT TCCTGTCCAA   1560

ACCTTCAACA AAGGCGGCTT CTTGAGACAG GCTAGACTGA AGTCACCAGC TTGGGTGGG    1620

GTCCACTATG TAACCTCAGT GCTCAGGAAC CCTTTCCCAT ACTGTCTGGA ACTATACTGT   1680

ATGTAGCTGG GTTTCCACGC ATGTGTGCCT GCACCCAGTC CATCTCATCT TCTATCTCCC   1740
```

```
TCCCCTTTCC CGCTTCCCCC CTCCCCACTC TCCATCTCAT CTTCCATCCC CACCTCTTCT    1800

GGTCCCTGCC CTGCTAAACT CAGGGTAGCT GCATTCCGCT GGCCTTCCCC ATGTTCCAGG    1860

CTTCAGTCCC TTCTCTGCAC CTGTCCTTTG TGAAGTGACC AGAGGATTTC TGATCCTGTC    1920

TCTGTCGCTC TGAAGGGTCA GGAGTTCCTC CTGCCTGGAC AAAGCCATCC TGACGCACAT    1980

AAATAAAACA AACATCAAAC TCTATTCAAC CCCCTGGAAC CCGTGTGTGT TACTTACAGG    2040

GCAAAAGAAT GGAGCAGGGG ATGGGTTGTG GGGGGGGGGG GTGGCATCTG GGTTGTCTAC    2100

AGTTGTGCAT TAAGTTGTAA TTAAGATGTG CATTTCTCCA AATAAGGGAA AATTATTCTG    2160

GATTATTTGA GTGAAGCTGA AAGGTGATCA TCTAGA                              2196
```

(2) INFORMATION FOR SEQ ID NO:4:

(i) SEQUENCE CHARACTERISTICS:
        (A) LENGTH: 350 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

```
AGGCACATGT CTCCTGGTTT ACCTCCCAAC GCACCTCAAG TCCCCAAGGT AGGTAGGCAC     60

TTGTATTCTG TAATTCAGAG AGGCAAATCA AACTGTTACA ATGTTTGCCC AAAGCTCCCC    120

AAGCAAAGTG GCCCTAAGAG TGAGCAAAGA GACTGCGTGC CTTCACTGCC TGTGTGAATC    180

CCTGCAGATA GTCTCTCATC TTGGTGCCCT TCCCACAGAG GCTGGGGCGG CAGGAGGGAG    240

CCTGGACAGC TCAGACACTG GGTCATTGAT GACTGTTGTG TGGGATACCT GCCGGGGCGC    300

AGGAGTGAGC CATGCCACCC CAGGAAGTGG TTCAGGGTGA CTCTTCTTGG               350
```

(2) INFORMATION FOR SEQ ID NO:5:

(i) SEQUENCE CHARACTERISTICS:
        (A) LENGTH: 283 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

```
TGCAGATAGT CTCTCATCTT GGTGCCCTTC CCACAGAGGC TGGGGCGGCA GGAGGGAGCC     60

TGGACAGCTC AGACACTGGG TCATTGATGA CTGTTGTGTG GGATACCTGC CGGGGCGCAG    120

GAGTGAGCCA TGCCACCCCA GGAAGTGGTT CAGGGTGACT CTTCTTGGCA CACCTGGGAG    180

GATGTAGCTG GTGCTGGCAC ACCCACCGTC ACGAGAGCTT CCTGTCCAAA CCTTCAACAA    240

AGGCGGCTTC TTGAGACAGG CTAGACTGAA GTCACCAGCC TTG                      283
```

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

```
GCTGGCACAC CCACCGTCAC GAGAGCTTCC                                      30
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

TTGGCACACC TGGGAGGATG            20

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

AGTGGTTCAG GGTGACTCT             19

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

AGGAGTGAGC CATGCCACC             19

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

CTGGGTCATT GATGACTG              18

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:11:

TGGCACACCC ACCGTCACGA GAGCT       25

(2) INFORMATION FOR SEQ ID NO:12:

(i) SEQUENCE CHARACTERISTICS:
        (A) LENGTH: 15 base pairs

```
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:12:

TGGCACACCT GGGAG                                                        15

(2) INFORMATION FOR SEQ ID NO:13:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:13:

TGGTTCAGGG TGACT                                                        15

(2) INFORMATION FOR SEQ ID NO:14:

(i) SEQUENCE CHARACTERISTICS:
            (A) LENGTH: 39 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:14:

CTGGGTCATT GATGACTGTT GTGTGGGATA CCTGCCGGG                              39
```

SYNDECAN ENHANCER ELEMENT AND SYNDECAN STIMULATION OF CELLULAR DIFFERENTIATION

CROSS REFERENCE TO RELATED APPLICATIONS

This application is a continuation-in-part of U.S. application Ser. No. 08/206,186, filed Mar. 7, 1994 (abandoned), which is a continuation-in-part of PCT/FI93/00514, filed Dec. 1, 1993.

FIELD OF THE INVENTION

This invention is in the field of cancer biology and therapy. Specifically, the invention is directed to methods for altering the differentiated state of a cell by altering syndecan-1 expression. The method allows for the normalization of the growth rate and differentiation state of malignant cells, and is based on the stimulation of syndecan-1 expression in the malignant cells. Re-expression of syndecan-1 in such malignant cells promotes their normal differentiated phenotype and prevents their formation into tumors. This method may also be applied to normal cells to maintain their expression of genes characteristic of the differentiated state, e.g., the method may be used to prevent baldness by maintaining keratin production.

In addition, the invention is directed to transcription regulatory elements associated with the syndecan-1 gene, such as the FGF-inducible Response Element (FiRE) and to the use of these transcription regulatory elements for controlling gene expression. The FiRE can also be used to target expression of a reporter gene to wound sites in vivo.

BACKGROUND OF THE INVENTION

Cell surface proteoglycans play an important role in the regulation of cell behavior (Ruoslahti et al., *Cell* 64:867–869 (1991)). Through their covalently bound glycosaminoglycan side chains, such proteoglycans can bind various extracellular effector molecules (Jalkanen, et al., in *Receptors for Extracellular Matrix*, J. MacDonald & R. Mecham, eds., Academic Press, San Diego, pp. 1–37 (1991)). One central challenge in proteoglycan biology is to understand the biological consequences which result from the binding of different effector molecules to cell surface proteoglycans. It is important to determine the intracellular responses triggered by effector binding and how these responses lead to altered cellular behavior. One way to investigate these matters is to create biological models which are dependent on the expression of specific proteoglycans.

Syndecan-1 is the best characterized cell surface proteoglycan (Saunders et al., *J. Cell Biol.* 108:1547–1556 (1989); Mali et al., *J. Biol. Chem.* 265:6884–6889 (1990)). It was originally isolated from mouse mammary epithelial (NMuMG) cells as a hybrid proteoglycan containing both heparan sulfate and chondroitin sulfate glycosaminoglycan side chains (Rapraeger et al., *J. Biol. Chem.* 260:11046–11052 (1985)). Recent studies have revealed its expression, not only on epithelial cells but also on differentiating fibroblasts of developing tooth (Thesleff et al., *Dev. Biol.* 129:565–572 (1988); Vainio et al., *J. Cell Biol.* 108:1945–1964 (1989)), on endothelial cells of sprouting capillaries (Elenius et al., *J. Cell Biol.* 114:585–596 (1991)) and on the surface of lymphocyte subpopulations (Sanderson et al., *Cell Regul.* 1:27–35 (1989)). This suggests that syndecan-1 function can vary from one cell type to another. Syndecan belongs to a family of proteoglycans with conserved plasma membrane and cytoplasmic domains but with dissimilar ectodomains (Mali et al., *J. Biol. Chem.* 265:6884–6889 (1990)). The conserved structure of syndecans suggests that it could participate in signal transduction through the plasma membrane.

Syndecan-1 binds several extracellular effector molecules but does so in a selective manner. For example, syndecan binds interstitial collagens and fibronectin but does not bind vitronectin or laminin (Koda et al., *J. Biol. Chem.* 260:8156–8162 (1985)); Saunders et al., *J. Cell Biol.* 106:423–430 (1988); Elenius et al., *J. Biol. Chem.* 265:17837–17843 (1990)). Moreover, syndecan-1 isolated from tooth mesenchyme has revealed selective binding to tenascin not observed for syndecan from NMuMG cells (Salmivirta et al, *J. Biol. Chem.* 266:7733–7739 (1991)). This suggests that variations in syndecan glycosylation alters the binding properties of syndecan. Polymorphism of syndecan-1 glycosylation has also been observed in simple and stratified epithelia (Sanderson et al., *Proc. Natl. Acad. Sci. USA* 85:9562–9566 (1988)); but whether these changes also reflect altered ligand recognition by syndecan remains unknown. Syndecan-1 also binds growth factors, such as basic fibroblast growth factor (Kiefer et al., *Proc. Natl. Acad. Sci. USA* 87:6985–6989 (1990); Elenius et al., *J Biol. Chem.* 267:6435–6441 (1992)).

Fibroblast growth factors (FGFs) are a family of heparin-binding peptides comprising 9 known members. Basic fibroblast growth factor (FGF-2 or bFGF) is synthesized by, and acts on various cell types and tissues. In vitro, it is a strong mitogen for cells of mesodermal origin, can modulate cell motility and differentiation, is a potent angiogenic factor, and potentiates neovascularization in vivo (Burgess and Magiac, *Ann. Rev. Biochem.* 58:575–606 (1989); Mason, *Cell* 78:547–552 (1994)). Keratinocyte growth factor (FGF-7 or KGF) is produced solely by cells of mesodermal origin. FGF-7 is proliferative for various epithelial cells (Basilico and Moscatelli, *Adv. Cancer Res.* 59:115–65 (1992); Rubin et al., *Cell Biol. Int.* 19:399–411 (1995)), and is also an important mediator of hair follicle growth and differentiation (Danilenko et al., *Am. J. Pathol.* 147:145–54 (1995); Guo et al., *Genes & Develop.* 10:165–75 (1996)). Both FGF-2 and FGF-7 are involved in wound healing, where they act as both autocrinic and paracrinic factors. In wounded skin FGF-2 is found in fibroblasts and endothelial cells. This growth factor stimulates proliferation of most cell types involved in wound healing, e.g., keratinocytes, fibroblasts, and vascular and capillary endothelial cells (Bennett et al., *Am. J. Surg.* 165:728–737 (1993)). FGF-7, which is synthesized only by fibroblasts and is induced during wound healing (Werner et al., *Science* 266:819–22 (1994); Werner et al, *Proc. Natl. Acad. Sci.* 89:6898–6900 (1992), and acts as a paracrinic factor on keratinocytes, inducing their proliferation and migration (Bennett et al., supra). FGF-7 is important for normal wound reepithelialization (Werner et al. (1994), supra). However, recent data with FGF-7 knockout mice indicate that KGF may not be required for normal wound healing (Guo et al., *Genes & Develop.* 10:165–175 (1996).

Growth factors are involved in the initiation, control, and termination processes of wound healing in an autocrinic and paracrinic manner. FGF-2 is produced by fibroblasts and is also found in association with extracellular matrix and basement membranes where it can be released by proteolytic activity. FGF-2 enhances the accumulation and proliferation of fibroblasts, keratinocytes, endothelial cells, and macrophages. In animal models it induces neovascularization, cell migration, and granulation tissue formation. It has been shown to accelerate wound healing in several different situations, e.g., incisions, burns, and diabetic wounds (See Bennett and Schulz, *Am. J. Surg.* 165: 728–737 (1993)).

Several AP-1 regulated genes are expressed during wound healing. Fos is rapidly activated on the wound healing edge (Martin and Nobes, *Mech. Dev.* 38: 209–215 (1992)). Jun may also be activated during wounding or wounding induced tumorigenesis (Marshall et al., *Virology* 188(1): 373–379 (1992). Cancerous cells are also known to be able to activate the AP-1 complex, and c-fos is required for malignant tumor progression (Saez et al., *Cell* 82:721–732 (1995)).

Yayon and coworkers (Yayon et al., *Cell* 64:841–848 (1991)) and Rapraeger and coworkers (Rapraeger et al., *Science* 252:1705–1708 (1991)) have shown that heparin-like molecules are required for the binding of FGF-2 to its high affinity receptor, indicating that syndecan-like molecules can also modulate the growth factor response. It has been observed that heparin is required for oligomerization of FGF-1 molecules leading to FGFR dimerization or further oligomerization and further signaling (Spivak-Kroizman et al., *Cell* 79:1015–24 (1994); Ornitz et al., *Mol. Cell Biol.* 12:240–47 (1992)). Several mechanisms, for both negative and positive regulation for FGF action by proteoglycans have been postulated (Schlessinger et al., *Cell* 83:357–360 (1995)). Syndecan-1 (Saunders et al., *J. Cell Biol.* 107:1199–1205 (1989)), can simultaneously bind FGF-2 and extracellular matrix molecules and this complex is able to promote DNA synthesis in 3T3 cells (Salmivirta et al., *J. Biol. Chem.* 267:17606–17610 (1992)).

However, it has also been reported that different heparin sequences can either activate or inhibit FGF-2 function (Guimond et al., *J. Biol. Chem.* 268:23906–23914 (1993)) and that the composition and length of syndecan side chains vary in a cell and tissue dependent manner (Sanderson and Bernfield, *Proc. Natl. Acad. Sci. USA* 85:9562–9566 (1989)); Rapraeger, *J. Cell Biol.* 109:2509–2518 (1989)); Salmivirta et al., *J. Biol. Chem.* 267:17606–17610 (1991)). Negative regulation of FGF action by syndecan-1 has also been reported (Mali et al., *J. Biol. Chem.* 268:24251–24258 (1993)); Aviezer et al., *J. Biol. Chem.* 269:114–121 (1994)), which may be due to the glycosaminoglycan side chain modification or different stochiometric ratios of FGFR and its co-receptor.

FGF-2 induces the transcription of number of genes encoding transcription factors, components of cytoskeleton, and ribosomal components (Burgess and Magiac, supra). For various growth factors and cytokines the inducible downstream transcriptional mechanisms are well characterized.

Several growth factors can elicit immediate early responses after receptor activation. For example, epidermal growth factor (EGF) and platelet derived growth factor (PDGF) induce, via the ras/ERK pathway, the ternary complex factor. The ternary complex factor acts together with the serum response factor to activate the serum response element (SRE) (Hill and Treisman, *EMBO J.* 14:5037–5047 (1995)). The cAMP response element (CRE) bound by CRE binding protein (CREB) homodimer, or as heterodimers in association with members of the ATF family, are also under the influence of growth factors, e.g., EGF, PDGF, and FGF-2. EGF and PDGF, with various cytokines, are also able to induce activation of signal transducers and activators of transcription (STAT), which are activated by Janus Kinases (JAKs) and act on the sis-inducible element (SIE) or the interferon stimulated response element (IRSE) (Hill and Treisman, *Cell* 80:199–211 (1995); Karin, *Cur. Op. Cell Biol.* 6:415–424 (1994)). Transforming growth factor alpha (TGFα) can activate nFkB.

FGF-2 and -7 both signal by binding to different cell surface tyrosine kinase receptors. However, no clear response element has been previously described for FGF and the signal receiving transcription factors remain to be discovered. FGF-2 can also be localized to the nucleus, where it is supposed to activate transcription (Nakiniski et al., *Proc. Natl. Acad. Sci. USA* 89:5216–5220 (1992); Bouche et al., *Proc. Natl. Acad. Sci. USA* 84:6770–6774 (1987)) as does FGF-1 (Wiedloche et al., *Cell* 76:1039–1051 (1994)). Accumulating evidence indicates that FGFs activate the MEF-MAP kinase pathway downstream from FGFR activation, via ras and raf (Umbhauser et al., *Nature* 376:58–62 (1995)). However, other signal transduction pathways also might contribute to FGF signaling, including a phospholipid-C driven pathway (Mason, *Cell* 78:547–552 (1994)).

Synergistic action of FGF-2 and cAMP by c-Jun and ATF-3 transcription factors at CRE has also been reported (Tan et al., *Mol. Cell Biol.* 14:7546–7556 (1994)). However, FGF was a poor activator of transcription without cAMP, indicating that besides FGF this type of FGF induced gene activation requires other extracellular signaling molecules. The SER of a-actin promoter, but not the fos promoter, has been proposed to be another target for FGF-2 induced gene activation in a cell culture model of cardiac myocytes (Parker et al., *J. Biol. Chem.* 267: 3343–3350 (1992)). For FGF induced negative regulation, one established gene element is the E-box motif, which binds myogenic basic helix-loop-helix (bHLH) transcription factors known to be inhibited by FGF-2. Proteins of the MyoD family: MyoD, myogenin, Myf5, and MRF, bind E-box elements in regulatory regions of various myogenic genes and are responsible for the terminal differentiation of myoblasts to myocytes (Edmondson and Olson, *J. Biol. Chem.* 268:755–758 (1993)).

The FGF-2 signaling effect seems to be dependent on its molecular weight. Different forms of FGF-2 are created in cells by alternative splicing. The low molecular weight form can induce cell migration, but does not have the mitogenic or proliferative potential of the high molecular forms (Bikfalvi et al., *J. Cell Biol.* 129:233–243 (1995)). The different molecular forms thus seem to use different signaling pathways.

The fact that cell surface proteoglycans can bind both growth factors and matrix components suggests that proteoglycans play a role in regulating, both temporally (timing of expression) and spatially (precise localization), growth promotion by immobilizing effector molecules to the vicinity of cell-matrix interactions. This is supported by the pattern of syndecan-1 expression during development which follows morphogenetic, rather than histological, patterns (Thesleff et al., *Dev. Biol.* 129:565–572 (1988); Vainio et al., *J. Cell Biol.* 108:1945–1954 (1989); and Vainio et al., *Dev. Biol.* 134:382–391 (1989)), and by the observation that syndecan expression is localized to sites of active proliferation (Elenius et al., *J. Cell Biol.* 114:585–596 (1991) and Vainio et al., *Dev. Biol.* 147:322–333 (1991)).

In simple epithelium, syndecan-1 is polarized to basolateral surfaces where it co-localizes with actin rich cytofilaments (Rapraeger et al., *J. Cell Biol.* 103:3683–2696 (1986)). Upon rounding, syndecan-1 is shed from the cell surface by proteolytic cleavage of the core protein at the cell surface, a process which separates the matrix binding ectodomain from the membrane domain (Jalkanen et al., *J.*

Cell Biol. 105:3087–3096 (1987)). In this way, syndecan-1 has been proposed to be involved in the maintenance of epithelial morphology. When mouse mammary tumor cells (S 115) are induced to change their morphology from an epithelial to a more fibroblastic or fusiform phenotype, syndecan-1 expression is lost (Leppä et al., *Cell Regul.* 2:1–11 (1991)). This loss has been found to occur in other cell types undergoing transformation (Inki et al., *Am. J. Pathol.* 139:1333–1340 (1991); Inki et al., *Lab. Invest.* 66:314–323 (1992)) suggesting that the loss of syndecan-1 expression is a common characteristic of malignant transformation.

SUMMARY OF THE INVENTION

The present invention is directed to a method for altering the differentiated state of a host cell by altering its expression of syndecan-1. The invention is also directed to a method for inducing and regulating syndecan-1 expression, especially in cells which exhibit a malignant phenotype, regardless of the origin of transformation.

In another aspect, the invention is directed to a treatment for suppressing tumor growth in a patient in need of such treatment, by the administration of a composition comprised of efficacious amounts of one or more agents that stimulate syndecan-1 synthesis in the tumor cells of such patient.

The invention is also directed to the DNA encoding enhancer and suppressor elements of the syndecan-1 gene and to the use of these elements for regulating heterologous gene expression. The vectors and host cells which incorporate DNA sequences containing the syndecan enhancer or suppressor are also encompassed by the invention. Methods of expressing a standard or heterologous gene comprising activating the syndecan enhancer element are also provided.

In addition, the invention is directed to a method for enhancing syndecan-1 expression in a host cell by activating the enhancer element of the syndecan-1 gene.

The invention is also directed to a method for enhancing syndecan-1 expression in malignant cells, by preventing suppression of syndecan gene transcription.

The invention is also directed to a biochemical method for the inactivation of suppressors of syndecan-1 gene expression in malignant cells.

In another aspect, the invention is directed to a method for stimulating cellular differentiation by enhancing syndecan-1 expression in both malignant and normal cells.

The invention is also directed to a method for stimulating cellular proliferation and differentiation, thus promoting tissue regeneration, especially in processes such as wound healing, by enhancing syndecan-1 expression.

This invention also relates to an enhancer element of the syndecan-1 gene having about 280 nucleotides. In addition, this invention relates to nuclear proteins that bind to the syndecan enhancer element causing enhancer activation, to the binding sites for these nuclear proteins on the syndecan enhancer, and to a complex of these nuclear proteins bound to the syndecan enhancer element. In particular embodiments of this invention, this nuclear protein is FIN-1, AP-1, or USF. In more specific embodiments, one or more of these proteins are in an oligomeric form, such as a dimer.

The invention further relates to a method of targeting expression of a gene product to cutaneous wounds using a construct comprising the syndecan enhancer gene operably linked to the gene of interest. Non-human transgenic animals comprising the syndecan enhancer operably linked to the gene of interest inserted into this germ line are also provided.

In another aspect, this invention relates to a method of activating or enhancing syndecan-1 expression in malignant cells by activating the syndecan enhancer element. In specific embodiments of this invention, the enhancer element is activated by FIN-1.

Further features, objects and advantages of the present invention will become more fully apparent to one of ordinary skill in the art from a detailed consideration of the following description of the subject invention when taken together with the accompanying drawings.

BRIEF DESCRIPTION OF THE FIGURES

FIG. 1 is a diagram of the assembly of mouse syndecan-1 gene and its promoter region.

FIGS. 2A–20. FIGS. 2A–20 contain the complete sequence of the mouse syndecan-1 gene [SEQ ID No: 1: (DNA) and SEQ ID No: 2: (protein)]. Regulatory sites for the expression of syndecan may also exist on the first intron following the first exon (see FIG. 1).

FIG. 3. FIG. 3 is a diagram of the assembly of mouse syndecan promoter region and the localization of the enhancer and suppressor elements together with restriction sites for three different enzymes.

FIG. 4. FIG. 4 is the complete sequence of the mouse syndecan enhancer element [SEQ ID No. 3: (DNA)] located 8–10 kbs upstream from the transcription initiation site as indicated in FIG. 3.

FIGS. 5A–5D. FIG. 5 (panels A–D) is a photographic presentation of reduced growth ability of syndecan-transfected cells in soft agar. Panel A (wild-type S115 cells) and B (control transfected cells) are pictures of the colonies that are formed in soft agar in the presence of testosterone, a feature typical for hormone-transformed cells. This growth ability was not observed with two independent syndecan-transfected cell clones (panels C and D), demonstrating how syndecan-1 re-expression can overcome the effect of hormone-induced transformation.

FIG. 6. FIG. 6 is a graphical presentation of how syndecan-transfected cells lose their ability to form tumors in nude mice. Wild-type or control transfected cells produce tumors in testosterone-administered nude mice while syndecan transfected cells revealed a very low tendency to produce tumors.

FIG. 7. FIG. 7 is a graphical representation of enhanced syndecan-1 expression in 3T3 cells by simultaneously administered basic fibroblast growth factor (bFGF) and transforming growth factor beta (TGF-β). This is an example of how syndecan-1 expression can be enhanced as a result of growth factor action in normal cells during the differentiation process.

FIG. 8. FIG. 8 is a graphical representation of enhanced syndecan-1 expression by MCF-7 cells exposed to the anti-estrogen toremifene. When exposed to estrogen, syndecan-1 expression in MCF-7 cells was reduced and the cells transformed. Subsequent treatment with the anti-estrogen (toremifene) restored syndecan-1 expression to levels close to that found in cells not exposed to estrogen and aided the cells in maintaining their normal growth behavior.

FIG. 9 is a graphical presentation of how the suppressor element (see FIG. 3) is active in S115 cells treated with testosterone. Indicated stretches of promoter sequences were transfected in hormone-treated S115 cells and analyzed for their transcription activity as described in Example VI. A dramatic drop was observed with suppressor construct as indicated in FIG. 3, and it was more obvious in transformed S115 cells (FIG. 9A) than in 3T3 cells (FIG. 9B). The vertical axes shown in the figure represent percent expression wherein expression in the absence of suppressor is taken as 100%.

FIG. 10. FIG. 10 is a graphical presentation of how the enhancer element is active in growth hormone-treated 3T3 cells. Various stretches of promoter were transfected in 3T3 cells and analyzed for their transcription activities. Fragment pXb6, which is the same as illustrated in FIG. 3 as an enhancer, revealed more than a ten fold stimulation of expression in 3T3 cells exposed to growth factors bFGF and TGFP if compared to non-treated cells. The vertical axis of the figure represents percent expression wherein the expression observed in untreated cells is taken as 100%.

FIG. 11A depicts the activation of the syndecan-1 gene by FGF-2 in NIH3T3 cells. 3T3NIH cells were exposed to 10 ng/ml of FGF-2 for 0, 4, 6, 8, 12, 24 and 48 hrs (F0–F48). RNA was isolated and the level of mouse syndecan mRNA (Syn-1) was quantified. GAPDH mRNA was included in each sample as a loading control. Control samples, with no FGF-2 treatment, were assayed for Syn-1 mRNA at 6, 12 and 24 hrs (C6-R4). Two individual exposures for each time point are depicted.

FIG. 11B shows that FGF-2 induced transcription of the syndecan-1 gene is based on the activation of a far upstream enhancer. In FIG. 11B transfection constructs comprising different fragments of the 11.5 kb upstream regulatory region of the syndecan-1 gene operably linked to a 1.1 kb sequence containing the proximal promoter of the syndecan-1 gene the chloramphenicol acetyltransferase (CAT) structural gene were assayed for CAT activity by transient transfection in 3T3NIH cells with and without FGF-2 treatment. Only the construct containing the most distal 2.2 kb fragment (pXb6) showed increased CAT activity following FGF-2 treatment.

In FIG. 11C this FGF-2 inducible region from pXb6 was further subdivided and the fragments were assayed similarly for enhancement of CAT expression. A construct containing a 280 bp element (pFiRE) retained full enhancement of CAT activity following FGF-2 treatment in both the forward (pFiRE) and the reverse orientation (pFiRErev).

In FIG. 11D, 3T3NIH cells were exposed to 10 ng/ml of FGF-2, for 4 and 24 hours followed by isolation of nuclei for a run-off experiment. c-jun and nur transcription was used as a positive control, and β-actin as a loading control.

FIGS. 12(A–C) FIG. 12 shows that enhancer activation is specific for FGF-2 in NIH3T3 cells. pFiRE was used to transfect 3T3NIH cells as in FIG. 11. The cells were starved in DMEM regular medium supplemented with CMS-serum (growth factor depleted) for 1 day. The transformed cells were then exposed to various growth factors in the same medium or to 5% fetal calf serum (FCS) supplemented medium. FGFs showed a clear enhancer activation not seen with the other growth factors that were tested (FIG. 12A). However, all the growth factors that were treated increased DNA synthesis, as tested by a $^{125}$IdU incorporation assay (FIG. 12B). The removal of the syndecan promoter had no effect on the pattern of growth factor induced FiRE activation (FIG. 12C).

FIG. 13A shows the results of DNAse I footprinting experiments of the enhancer element, indicating that the enhancer includes five DNA binding motifs. DNAse I footprinting was performed with end-labeled pFiRE vector alone (naked) or together with FGF-2 induced (FGF-2) and non-induced (control) nuclear extracts. The products of the A+G sequence reaction of pFiRE are also depicted. Five footprinted motifs, showing binding of proteins in the nuclear extract to sequences within pFiRE, are marked with numbered boxes.

FIG. 13B. FIG. 13B depicts the sequence of the FGF-2 inducible enhancer (SEQ ID No:5). The sequence of the pFiRE fragment is shown. The sequence of the footprinted motifs identified in FIG. 13A are underlined and together restore 100% of the enhancer activity. Motif 3 contains the binding site for FGF-inducible nuclear factor FIN-1. This binding site does not contain sequences previously identified as consensus binding sites for transcription factors. Motifs 5 and 4 are AP-1-like binding sites, motif 2 is an E-box, and motif 1 is an unknown transcription factor recognition site.

FIG. 14A–F shows that FGF-2 inducible and noninducible nuclear factors bind to the enhancer. In FIG. 14A, the results of a gel retardation analysis for each enhancer motif and for an SP1 consensus oligonucleotide (control) are shown. This analysis was performed to obtain protein complexes that bind at each of the protein binding site shown in FIG. 14. Nuclear extracts derived from FGF-2 treated (f or FGF) or untreated (c or control) 3T3 cells were incubated with DNA containing motifs 1–5 as indicated. In FIG. 14B–F, motifs 1 (FIG. 14B), 2 (FIG. 14C), 3 (FIG. 14D), 4 (FIG. 14E), or 5 (FIG. 14F) were further competed with a molar excess of specific (s) or non-specific (ns) oligonucleotides. The non-specific oligonucleotide for motifs 3, 4 and 5 was the motif 1 sequence and for motifs 1 and 2, the non-specific oligonucleotide was the motif 3 sequence. Specific binding is indicated by an arrow.

FIGS. 15A–F. FIGS. 15A–F shows that FiRE involves FGF-inducible AP-1s and constitutive USFs. In FIG. 15A, specific binding (indicated by a line) on motif 5 was competed by molar excess of AP-1 consensus oligonucleotide, but not by E-box consensus oligonucleotide. Antibodies against c-fos and c-jun removed the specific bond and raised a supershift (arrow). Antibodies against USF, used as a negative control, had no effect.

FIG. 15B. In FIG. 15B, specific binding (indicated by a line) on motif 4 was competed by a molar excess of AP-1 consensus oligonucleotide, but not by E-box consensus oligonucleotide. Antibodies against c-fos and c-jun removed the specific bond and raised a supershift (arrow). Antibodies against USF, used as a negative control, had no effect.

FIG. 15C. In FIG. 15C specific binding (indicated by a line) on motif 3 was competed by a molar excess of AP-2 consensus oligonucleotide. AP-2 antibody raised a supershift in a reaction with labeled AP-2 oligonucleotide and 3T3 nuclear cell extracts but did not produce a supershift with labelled motif 3 and nuclear extracts deemed from FGF-2 treated 3T3 NIH cells. A gel retardation gel as shown in FIG. 1SA was run and exposed to UV light. The specific bands, representing the bound protein-DNA complex, were cut out, eluted overnight, and loaded onto an SDS-PAGE gel to analyze their molecular weight. Two reproducible bands for the motif 3 binding protein are shown. The molecular weight of the nuclear factors were approximated by subtracting the calculated molecular weight of each oligonucleotide from the complex molecular weight.

FIG. 15D. In FIG. 15D, specific binding (indicated by a line) on motif 2 was competed by a molar excess of E-box consensus oligonucleotide, but not by AP-1 consensus oligonucleotide. Antibody against USF eliminated the specific band, but the c-dun antibody had no effect.

FIG. 15E. In FIG. 15E the molecular weight of the protein bound to motif 1 is determined following UV crosslinking.

FIG. 15F. FIG. 15F is a schematic depicting the binding of various nuclear factors to the syndecan enhancer element.

FIG. 16. FIG. 16 shows that enhancer activity is reduced in 3T3 cells expressing high levels of syndecan-1. Syndecan-1 transfected (3T3 1.5) and wild-type (3T3 WT) 3T3 cells were transiently transfected with the pFiRE construct and analyzed for reporter gene expression (CAT activity). The pFiRE activation observed in 3T3 cells not expressing high levels of syndecan-1 was significantly reduced in syndecan-1 expressing 3T3 cells. Solid bars indicate CAT activity in non-treated cells, while hatched bars indicate CAT activity in FGF-treated cells.

FIG. 17. FIG. 17 is a plasmid map of pTRG Syn Prom, showing various restriction sites within the MCS-SP-LacZ region.

FIG. 18. FIG. 18 is a plasmid map of pTRG ENH, showing various restriction sites within the MCS-SP-LacZ region.

FIGS. 19A–F depicts micrographs showing staining resulting from reporter gene activation in 2 day old transgenic mice tail wounds. FIG. 19A is a schematic presentation of the transgenic constructs used. The SynPro construct contains 2.3 kb of the syndecan regulatory region from the XhoI restriction site (+140 bp from the major transcription initiation site) to SphI (−2.2 kb) operably linked to the β-galactosidase reporter gene. The FiRE construct also contains the 280 bp for upstream inducible element (PstI-StyI fragment) in front of SynPro. FIG. 19B depicts a 2 day old wound on SynPro transgenic animal's tail skin showing no X-gal staining. FIG. 19C depicts similar wounds made to FIRE transgenic animal's tails. Heavy staining is seen both in proliferating and migrating keratinocytes and in the keratinocytes of hair follicles close to the wound site (arrow). FIG. 19D shows stratifying epithelial cells closer to the wound edge, where FiRE is still active. FIG. 19E shows closed and recently healed wounds, where the staining is fading. FIG. 19F shows resting skin where FiRE is not activated.

FIGS. 20a–c shows the results of cell culture experiments demonstrating that FIRE is specific for FGF-7 in keratinocytes.

FIG. 21 depicts the amount of enhancer activation, as measured by the relative expression of the CAT reporter gene, for deletion mutants of each motif. For the motif 1 deletion mutant (Del M1), the 3' end of FIRE was deleted. For the motif 2 deletion mutant (Del M2), the E-Box was replaced by a KpnI recognition site. For motif 3–4 deletion mutants to (Del M3 and Del M4), a central 10 bp sequence was replaced with a 10 bp sequence including an SpeI recognition site. For the motif 5 deletion mutant (Del M5) a PCR product from motif 4 to motif 1 was generated. The mutant enhancers were ligated into a CAT reporter plasmid with a 1.1 kb sequence proximal promoter and transfected. Cells were treated with FGF-2 and CAT activity was assayed.

FIG. 22a–d depicts the results of experiments to determine whether protein synthesis is needed for the induction of FGF-inductible transcription factors. Cells were treated with FGF-2 with our without 1 mg/ml (final concentration) of translation inhibitor cycloheximide. Each motif (2–5) is shown with separately run control (Cont.), FGF-2 (FGF), and simultaneous FGF-2 and cycloheximide treatment (FGF+cycloh.). The cycloheximide treatment abolishes the specific binding on motifs 3, 4, and 5, but not on motif 2.

FIG. 23 depicts the amount of enhancer activation, as measured by the relative expression of the CAT reporter gene, for pXb6 containing the SV40 promoter and pCATSynProm in the presence and in the absence of the simultaneous administration of FGF-2 and TGF-β.

FIG. 24 depicts experiments showing that TPA or other activators of AP-1 do not activate the AP-1 driven FiRE. Different agents known to induce fos-jun complexes and activate AP-1 driven promoters, were tested for FiRE activation in CAT assay with the minimal promoter transferred in stable 3T3NIH cells in the presence of protein kinase C activator (TPA, 10 mm), protein phosphatase 1 and 2 inhibitors (DA and calycalin A), a cAMP activator (forskolin), or a tyrosine phosphatase inhibitor (orthovanadate).

DEFINITIONS

Figure 1:
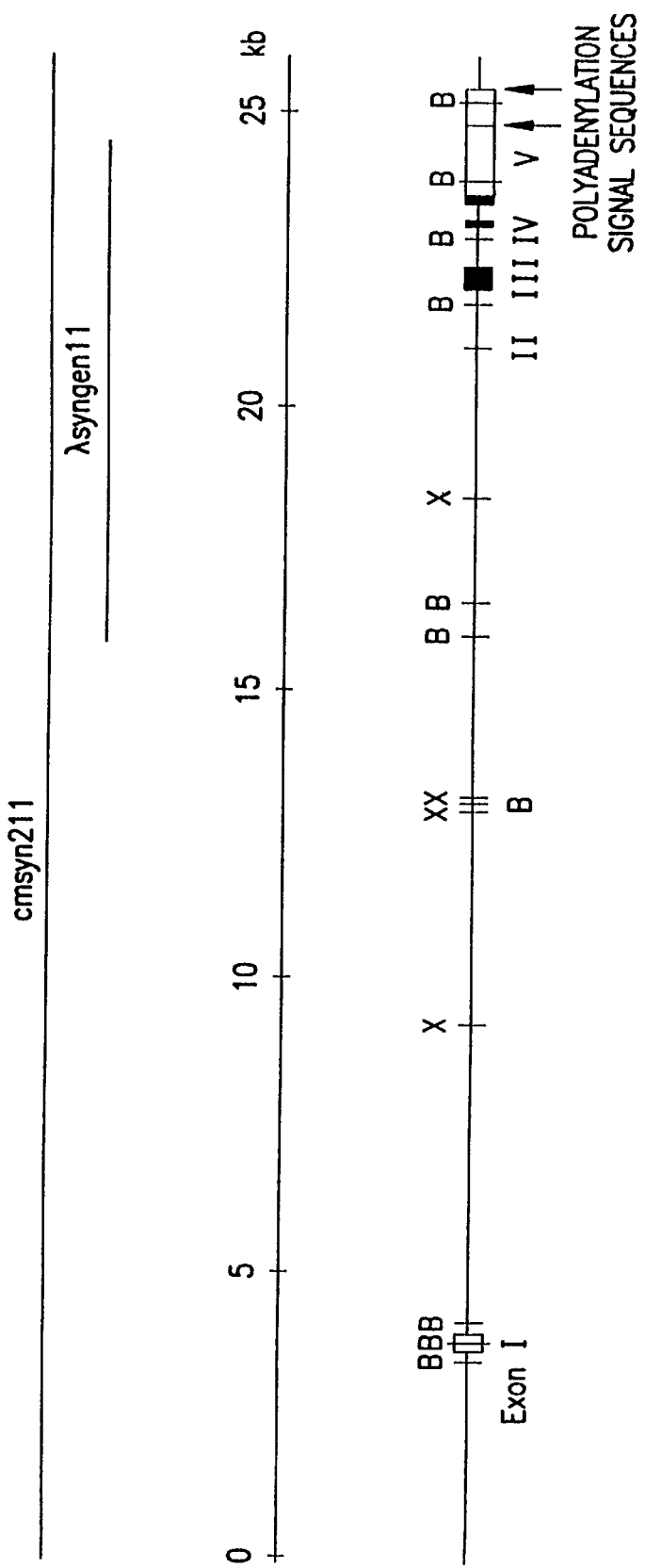
FIG. 1.

In order to provide a clearer and more consistent understanding of the invention the following definitions are provided.

"Enhancement" or "Stimulation" of syndecan expression. By "'enhancement' or 'stimulation' of syndecan expression" is meant an effect of increasing the synthesis of syndecan, either by the induction or de-suppression (de-repression) of syndecan gene transcription and/or translation.

Cell growth. By "cell growth" is meant cell replication, both controlled and uncontrolled.

Malignant. By "malignant" is meant uncontrolled cell growth.

More Differentiated Phenotype. In stating that a cell has a "more differentiated phenotype," it is meant that the cell possesses a phenotype usually possessed by a certain cell type more differentiated than the cell, which the cell was deficient in prior to enhancement of syndecan expression. This phenotype may be defined by one or more phenotypic characteristics. For example, an epithelial cell is a more differentiated phenotype of a mesenchymal-like shape; therefore, the ability of the method of the invention to maintain cells in an epithelial cell morphology rather than a mesenchymal-like shape is a more differentiated phenotype within the meaning of the definition. Continuous syndecan expression is necessary for the maintenance of terminal differentiation of epithelial cells.

Syndecan expression is also linked to the normal differentiation of mesenchymal cells. However, unlike epithelial cells, continued expression of syndecan is not needed for maintenance of terminal differentiation in mesenchymal cells. To induce differentiation of suitable mesenchymal precursors (such as a "condensing mesenchymal" cells) to fully differentiated mesenchymal cells, only a transient expression of syndecan is required. A terminally differentiated mesenchymal cell is a "more differentiated phenotype" than a condensing mesenchymal cell.

Other phenotypes that are characteristic of syndecan-deficient cells but not of their non-deficient counterparts include fusiform shapes with long filopodial extensions. There is an extensive under- and overlapping of these processes causing the cells to appear to have a defect in cell adhesion.

In another example, syndecan-deficient NMuMG cells continue to secrete milk fat globule antigen (and thus appear mammary-like) and continue to express cytokeratins (thus appear epithelial-like). However, their actin-containing cytoskeleton is disorganized and their expression of beta, integrins and E-cadherins at the cell surface is markedly reduced. Upon increased expression of syndecan, these phenotypes are corrected so that there is no reduction in cell surface integrins or E-cadherin and the cell has an epithelial morphology. Therefore, the amount of cell surface integrins or E-cadherin is useful as a marker of syndecan expression and may be used to monitor the amount of a drug needed for efficacious results according to the method of the invention.

Efficacious Amount An "efficacious amount" of an agent is an amount of such agent that is sufficient to bring about a desired result, especially upon administration to an animal or human.

Administration. The term "administration" is meant to include introduction of agents that induce syndecan expression into an animal or human by any appropriate means known to the medical art, including, but not limited to, injection, oral., enteral and parenteral (e.g., intravenous) administration.

Pharmaceutically Acceptable Salt. The term "pharmaceutically acceptable salt" is intended to include salts of the syndecan-inducing agents of the invention. Such salts can be formed from pharmaceutically acceptable acids or bases, such as, for example, acids such as sulfuric, hydrochloric, nitric, phosphoric, etc., or bases such as alkali or alkaline earth metal hydroxides, ammonium hydroxides, alkyl ammonium hydroxides, etc.

Pharmaceutically Acceptable Vehicle. The term "pharmaceutically acceptable vehicle" is intended to include solvents, carriers, diluents, and the like, which are utilized as additives to preparations of the syndecan-inducing agents of the invention so as to provide a carrier or adjuvant for the administration of such compounds.

Treatment The term "treatment" or "treating" is intended to include the administration of compositions comprising efficacious amounts of syndecan-inducing agents to a subject for purposes which may include prophylaxis, amelioration, prevention or cure of a medical disorder, suppression of tumor growth, or the promotion of hair growth.

Operably Linked. In the context of an expression vector, "operably linked" refers to a location, juxtaposition, and/or orientation of various elements, e.g., enhancer, promoter, and structural gene, within an expression vector so that the structural gene is expressed in any appropriate host cell. When an enhancer is operably linked to a structural gene, expression of the structural gene is enhanced over the level of expression observed in the absence of the enhancer.

Syndecan Enhancer Element. In the context of this invention, "syndecan enhancer element" is a DNA sequence having significant structural homology to the sequence of FIG. 13B and retaining the same functional properties as the sequence of FIG. 13B, e.g., enhancing the expression of the syndecan-1 gene by FGFs. For example, in certain embodiments of this invention, a syndecan enhancer element may retain 95% sequence homology to the sequence in FIG. 13B, while retaining enhancer activity. In other embodiments of this invention, a syndecan enhancer element may retain 90% sequence homology to the sequence in FIG. 13B, while retaining enhancer activity.

DETAILED DESCRIPTION OF THE PREFERRED EMBODIMENTS

Briefly, in its broader aspects, the present invention comprehends a method for maintaining a differentiated phenotype in a normal (non-malignant) cell that otherwise would suppress syndecan-1 expression, by maintaining syndecan-1 expression in such cell. The invention also comprehends a method for inducing a more differentiated phenotype in a malignant cell that lacks (or is deficient in) syndecan-1 expression, by stimulating syndecan-1 expression in such a cell. As used herein, a cell said to "lack" syndecan-1 expression, may either be completely deficient in syndecan-1 protein or produce insufficient syndecan-1 to maintain or attain a desired differentiated phenotype.

The methods of the invention will not only prevent the progression (worsening) of a transformation state and the growth of tumors, but will also maintain cells in a state in which they continue to perform differentiated functions. Examples of differentiated functions of non-malignant cells include the secretion of specific proteins and/or other macromolecules and hair formation by epidermal cells of skin. Thus, according to the invention, administration of agents capable of inducing syndecan-1 expression in epidermal skin cells of the scalp will promote hair growth among bald (or balding) people.

The subject method may be accomplished by biochemical., chemical or even molecular biological methods. While the method is applicable to a variety of cancer (both malignant and non-malignant) and normal cells, it is particularly adaptable for treating malignant cells which have become transformed. This includes cells transformed due to hormonal influences of the body or environmental influences, such as chemicals or radiation exposure. The method is especially effective for tumors characterized by loss of syndecan-1 expression, for example, a glioma, myeloma, carcinoma, sarcoma, lymphoma, or adenoma.

Generally, any cell genetically capable of expressing syndecan-1 can be stimulated to express syndecan-1 by the method of the invention. Syndecan-1 is naturally expressed in a wide variety of epithelial cells in mature and embryonic tissues and by various embryonic mesenchymal tissues undergoing inductive interactions with epithelia. In addition, syndecan-1 is naturally expressed by Leydig cells, by developing B-lymphocytes and by a subpopulation of plasma cells.

Enhanced syndecan-1 expression may be achieved by administration of compositions containing a biochemically, and/or chemically and/or molecular-biologically active component to an individual. Compositions may be administered orally, intravenously, subcutaneously or locally, or by any other method which will allow cells, normal or malignant, to be exposed to the syndecan-1 expression enhancing component.

By a "biochemically" or "chemically" active component is meant a component that alters the endogenous syndecan biochemistry or chemistry of the target cell without altering syndecan gene expression per se. Such alteration may include altering the half-life of syndecan protein or mRNA, so as to increase levels of syndecan-1 protein in the cell. For example, by altering the external domain of the cell's endogenous syndecan, or its cell surface membrane properties in general., may be altered so as to retain higher levels of syndecan on the cell surface; and, altering the syndecan protein active site(s), so as to enhance the efficiency of the syndecan response.

By a "molecular-biologically" active component is meant a component that alters endogenous syndecan-1 gene expression in a manner that allows for an increase in cellular syndecan-1, such as, for example, by stimulating transcription, preventing (or reducing) suppression of transcription, de-repression of transcription, or by generally increasing levels of mRNA and/or translation efficiency.

It is known that cellular transformation involves activation of cellular growth-stimulating genes (e.g., oncogenes) and inactivation of other genes which suppress cell growth.

It has recently been shown that loss of syndecan-1 expression is observed upon transformation of cells, and that this suppression is due to syndecan gene inactivation (Leppä et al., *Cell Regul.* 2:1–11 (1991); Inki et al., *Am. J. Pathol.* 139:1333–1340(1991); Inki et al., *Lab. Invest.* 66:314–323 (1992)). This was demonstrated in several biological models of carcinogenesis including models in which transformation is caused by oncogenes, by chemical carcinogens, by UV-light or by hormone-exposure. Thus, syndecan-1 gene suppression is a general phenomenon associated with cellular transformation. All the manipulations of such cells which induce syndecan-1 expression cause these cells to assume a more differentiated phenotype, and thus, reduce their potential tumorigenic behavior and tendency to metastasize.

In order to determine whether steroids were having a direct and causal effect on the transformation of S115 cells, normal regulatory elements of the syndecan-1 gene were replaced with hormone-inducible elements. As a result of this change, the new cell lines no longer underwent transformation as the result of exposure to steroid.

In a preferred embodiment, the cell in which syndecan-1 expression is stimulated is steroid-responsive. Examples of such steroid-responsive cells include breast cells, endometrium cells and prostate cells, especially in the malignant state. In a highly preferred embodiment, the cell is responsive to estrogen and/or androgen.

Examples of other cell types that will respond to the treatment of the invention include malignant and non-malignant mesenchymal cells.

The regulatory elements of a given gene are commonly located upstream from (i.e., 5 prime to) the transcription initiation site. Syndecan-1, however, has a very peculiar gene structure, in which the first and second exons are separated by a very large intron (FIG. 1). This could mean that, in addition to base sequences upstream from the transcription site, syndecan expression may also be susceptible to regulation by base sequences located in the first intron.

Nucleotide sequence elements responsible for regulating syndecan gene expression were identified by ligating DNA elements lying upstream of the syndecan gene transcription initiation site to vectors containing the chloramphenicol acetyltransferase (CAT) gene and determining the CAT enzymatic activity expressed by cells transformed with such vectors (see Example VI for experimental details).

Figure 10:
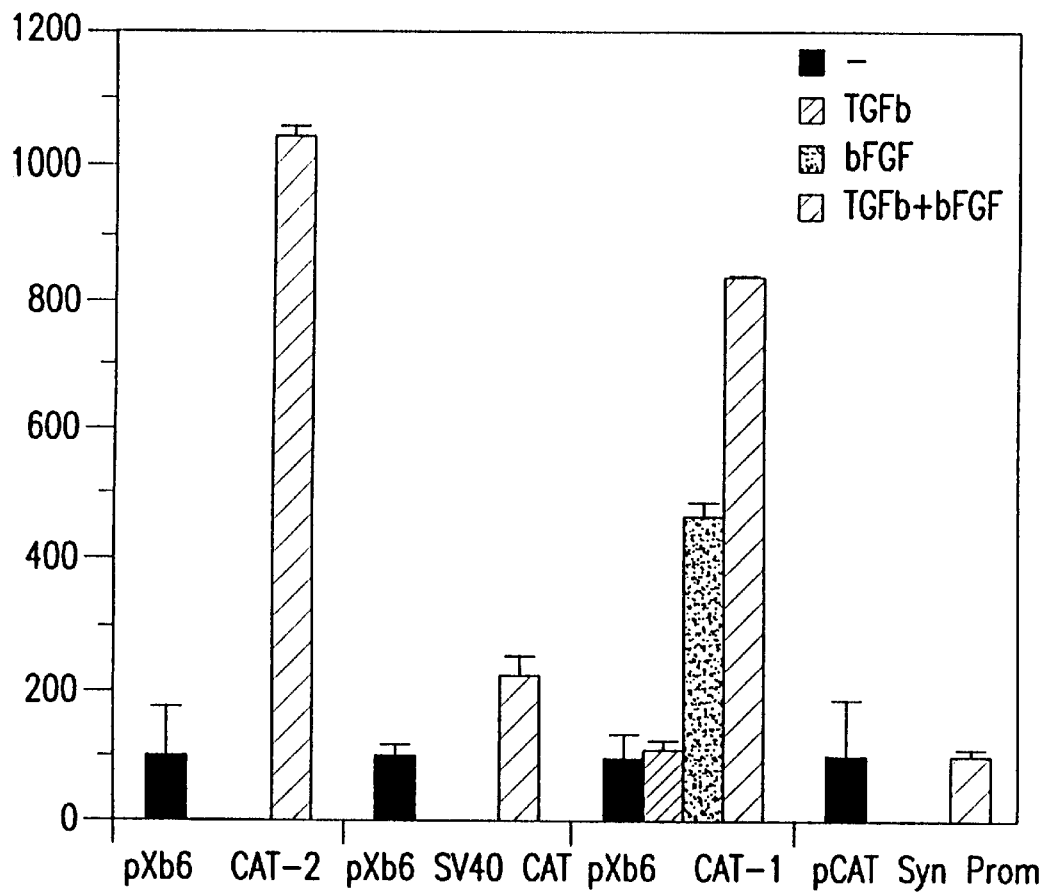

It was found that the syndecan-1 gene has a strong enhancer element located approximately 11.5 kb upstream from the transcription initiation site. Results such as those presented in FIG. 10 indicate that the DNA element shown in FIG. 4 (SEQ ID No. 3) is capable of enhancing expression. Further experiments localized the enhancer to the 350 nucleotide sequence shown as SEQ ID No. 4. DNA encoding the enhancer may be linked to recombinant constructs containing a promoter and a structural gene and may serve to enhance recombinant expression.

Figure 13A:
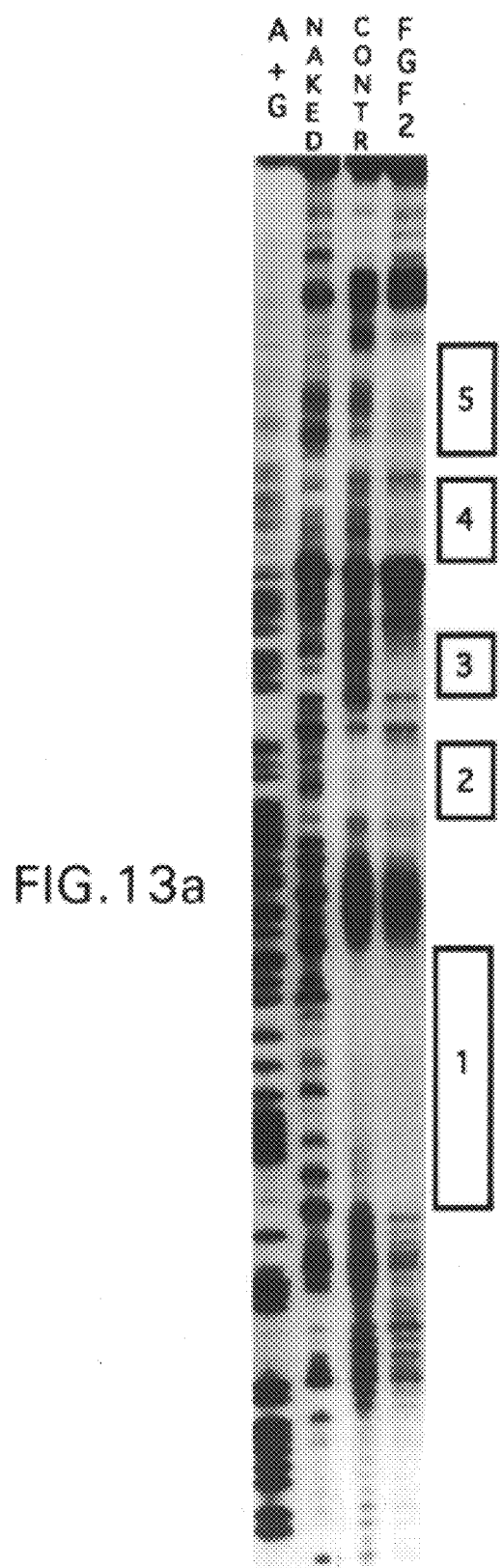
FIG. 13A.

The enhancer element has now been further localized to a 280 nucleotide sequence, depicted in FIG. 13B (SEQ ID NO. 5). This sequence may also be linked in either orientation to recombinant constructs containing a promoter and a structural gene, including heterologous promoters or structural genes, to enhance recombinant expression.

Cells destined to differentiate during organ formation or tissue regeneration also exhibit enhanced syndecan-1 expression (Vainio et al., *Dev. Biol.* 147:322–333 (1991); Elenius et al., *J. Cell Biol.* 114:585–595 (1991)). Growth factors are candidates for regulating syndecan-1 expression since they are known to be involved in the regulation of early development and cellular differentiation (Heath et al., *Curr. Opin. Cell Biol.* 3:935–938 (1991)). The suggestion that growth factors are involved is also supported indirectly by the fact that the expression of two embryonically important growth factors (TGF-β and FGF) has been shown to coincide with syndecan-1 expression in developing tooth (Vaahtokari et al., *Development* 113:985–994 (1991); Wilkinson et al., *Development* 105:131–136 (1989)).

Figure 7:
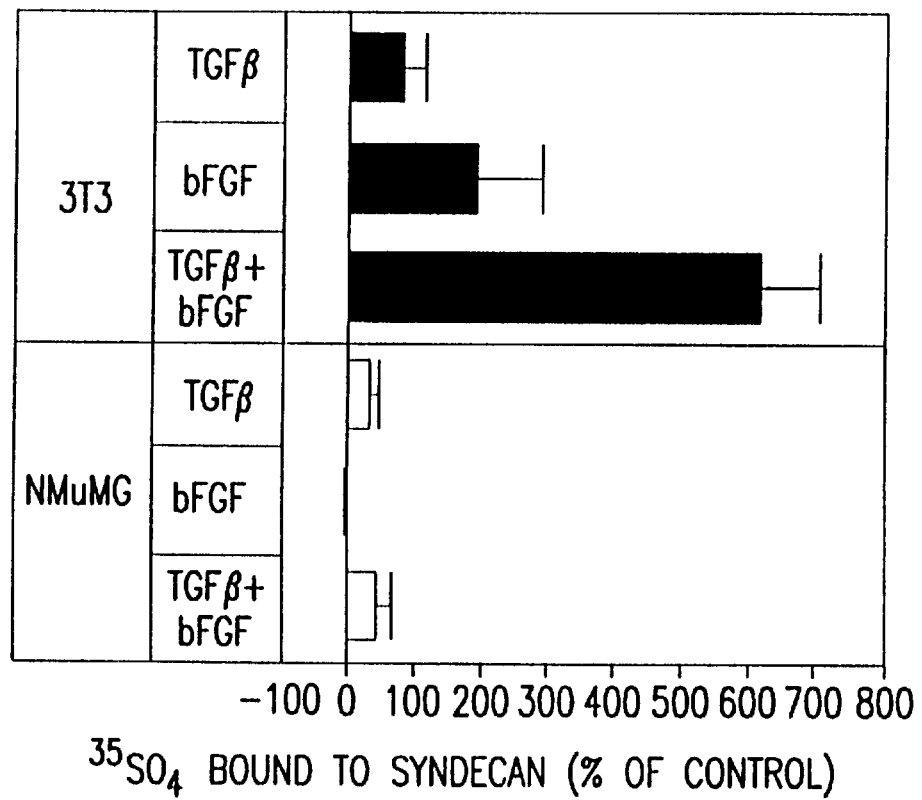

Based upon these findings, the possible effect of growth factors on the expression of syndecan-1 has been tested. It was found that both FGF-2 and TGF-β enhance syndecan-1 expression by 3T3 cells, if these agents are administered together (FIG. 7). FGF-2, when administered alone also shows enhancement of syndecan-1 expression. This stimulation produced syndecan-1 levels close to the levels observed in syndecan-expressing epithelial cells (Elenius et al., *J. Biol. Chem.* 267:6435–6441 (1992)) prior to their becoming malignant (Leppä et al., *Proc. Natl. Acad. Sci. USA* 89:932–936 (1992)). The findings suggest that growth factors, and their derived fragments and domains may prove to be valuable tools for the regulation of syndecan expression.

This 280 bp FGF-inducible response element is located 11.6 kb from the translation start site of the syndecan-1 gene and shows at least about a ten-fold activation in FGF-2 treated 3T3 cells. In mesenchymal cells this activation seems to be restricted to FGF-2. No response to serum or other growth factors tested was observed. Interestingly, FiRE also shows a distinctive specificity among the FGF family members, because FGF-1 did not activate or suppress this element. This suggests a separate signaling pathway and function for FGF-1 and -2 in mesenchymal cells. FGF-7 is a poor activator of mesenchymal cells and did not activate the enhancer. However, in cultured keratinocytes FGF-7 was able to activate FiRE. However, serum, PDGF, FGF-1 and surprisingly also FGF-2, failed to activate FiRE in cultured keratinocytes. In another epithelial cell line (NMUMG) FiRE was not inducible by any of the growth factors tested, which was expected, since NMuMG are FGFR negative cells. This indicates that the activation FiRE is cell specific, and in addition, is selective for different members among the FGF family in a cell dependent manner.

Figure 15A:
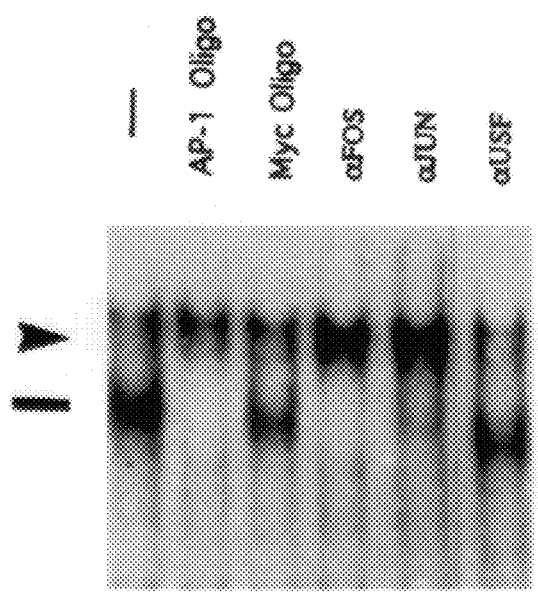
Figure 15B:
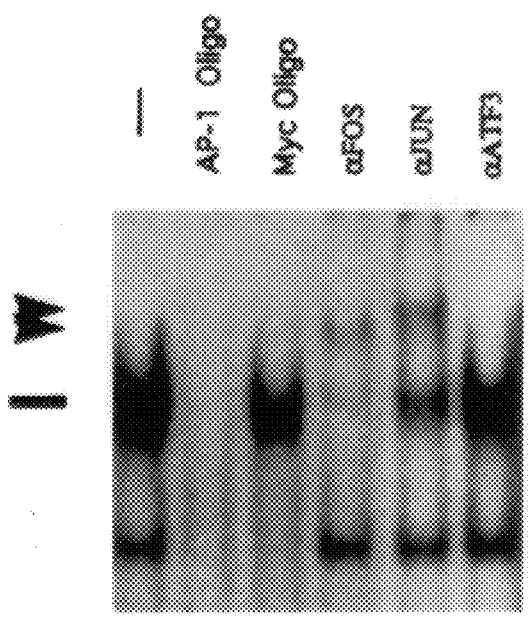
Figure 15F:
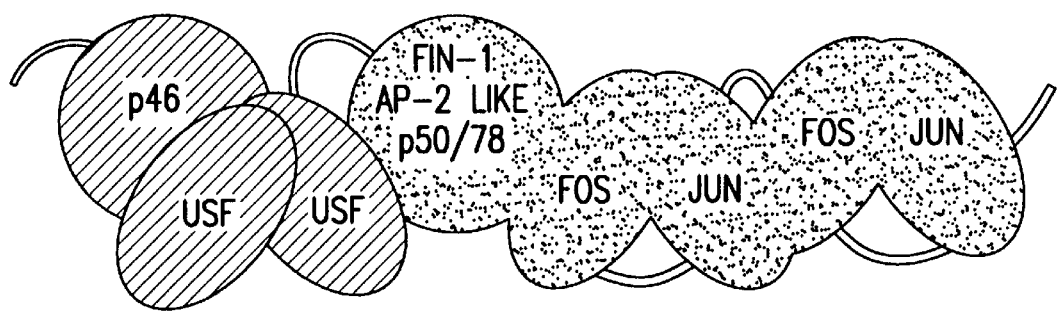

FiRE binds both FGF inducible and non-inducible nuclear factors bound in an organized array (see FIG. 15F). The FiRE nuclear factors include two AP-1 factors, which are homo- or heterodimers composed of the products from the fos and jun families. Members of the fos and jun families include c-Jun, JunB, JunD, c-fos, Fos-B, Fra-1 and Fra-2. Components of AP-1, fos and jun, as well as other members of the fos and jun families, are rapidly activated by a vast amount of extracellular stimuli. Their activation is brought about by either direct gene activation or posttranslational modifications (Karin, *Curr. Op. Cell Biol.* 6:415–424 (1994)). In several studies, FGFs are shown to activate c-fos. FGF-2 is also known to induce the expression of c-fos and c-jun in 3T3 cells (Janet et al., *Exp. Cell Res.* 198:305–344 (1992)). Our results show that FGF treatment results in transcriptionally active fos-jun heterodimers. FiRE is bound by at least two AP-1 complexes, which both seem to be required for FGF induction, since deletion of one AP-1 site dramatically decreases the FGF response.

FiRE also binds USF, which is a ubiquitously expressed homodimeric transcription factor (Gregor et al., *Genes Develop.* 4:1730–1740 (1990)). The binding site for USF on the FiRE is the E-box. USF is constitutively expressed in 3T3 cells (Miltenberger et al., *Mol. Cell Biol.* 15:2527–2535 (1995)). It is not known to be under influence of any growth factor. In FiRE, USF is not activated by FGF but it is involved in the complex with inducible components. Replacement of the E-Box does not, however, strongly reduce the FGF response on FiRE. This might be due to replacement of USF with another constitutively active transcription factor, which would be able to interact with inducible components. Alternatively, protein-protein interactions might hold USF in the FiRE complex although its optional binding target in DNA has been destroyed. However, the integration of the FiRE-reporter gene construct into the chromosome could still result in requirement for USF since these experiments were done with extrachromosomal plasmid DNA in a transient transfection.

Besides AP-1 and USF the FiRE element also binds another non-inducible component as well as a novel FGF-inducible AP-2-like transcription factor. AP-2 is a cell-specific 50 kDa transcription factor expressed, among other tissues, in keratinocytes in high amounts (Leask et al., *Proc. Natl. Acad. Sci USA* 88:7948–7952 (1991)). Multiple forms of AP-2 are generated by alternative splicing (Meier et al., *Dev. Biol.* 169:1–14 (1995)) and also one AP-2 related transcription factor, AP-2b has been cloned (Moser et al., *Development* 121:2778–2788 (1995)). FIN-1 is a novel FGF-inducible nuclear factor that binds FiRE and can be competed with AP-2 consensus oligonucleotide. This factor is not recognized by AP-2 antibody, but could be a member of a larger AP-2 family. It is known, that AP-2 can form heterodimers without DNA binding and, that AP-2 dimerization is required for binding (Williams and Tijan, *Science* 251:1067–1071 (1991)). Thus, FIN-1 likely binds to FiRE as a dimer (see FIG. 15).

The complex structure of FiRE with its far upstream location could explain the difficulties of discovering FGF induced gene activation. It also indicates that FGF-induced signals are not restricted to CRE and SRE, their formerly proposed endpoints.

FiRE can be considered a secondary reponse element requiring de novo protein synthesis after initial FGFR activation. This response element can further diversify FGF influence on different cell types. FiRE is the first example of this type of a response element.

The binding sites for each of these nuclear proteins on the enhancer element have been mapped, see FIG. 14, and their sequence has been identified. See FIG. 15. AP-1 binds to motifs 4 and 5; FIN-1 binds motif 3; USF binds motif 2; and p46 binds motif 1. These binding sites constitute 100% of the enhancer activity. These binding sites on the enhancer element for FIN-1 do not contain any previously described consensus sequences for transcription factors.

Thus the invention is also directed to a recombinant DNA molecule that comprises a syndecan enhancer element that comprises each of the following sequences:
(a) TGGCACACCCACCGTCACGAGAGCT (SEQ ID No. 11);
(b) TGGCACACCTGGGAG (SEQ ID No. 12);
(c) TGGTTCAGGGTGACT (SEQ ID No. 13);
(d) AGGAGTGAGCCATGCCACC (SEQ ID No. 9); and
(e) CTGGGTCATTGATGACTGTTGTGTGG-GATACCTGCCGGG (SEQ ID No. 14).
Alternatively, (a) can be dGCTGGCACACCCACCGT-CACGAGAGCTTCC (SEQ ID No. 6),
(b) can be TTGGCACACCTGGGAGGATG (SEQ ID No. 7), (c) can be AGTGGTTCAGGGTGACTCT (SEQ ID No. 8), and
(e) can be CTGGGTCATTGATGACTG (SEQ ID No. 10).

The invention is also directed to a recombinant DNA molecule that comprises a syndecan enhancer element that comprises at least one sequence selected from the group consisting of:
(a) TGGCACACCCACCGTCACGAGAGCT (SEQ ID No. 11);
(b) TGGCACACCTGGGAG (SEQ ID No. 12);
(c) TGGTTCAGGGTGACT (SEQ ID No. 13);
(d) AGGAGTGAGCCATGCCACC (SEQ ID No. 9); and
(e) CTGGGTCATTGATGACTGTTGTGTGG-GATACCTGCCGGG (SEQ ID No. 14).
Alternatively, (a) can be dGCTGGCACACCCACCGT-CACGAGAGCTTCC (SEQ ID No. 6),
(b) can be TTGGCACACCTGGGAGGATG (SEQ ID No. 7), (c) can be AGTGGTTCAGGGTGACTCT (SEQ ID No. 8), and (e) can be CTGGGTCATTGATGACTG (SEQ ID No. 10).

The invention is also directed to a recombinant DNA molecule that comprises a syndecan enhancer element that comprises at least one sequence selected from the group consisting of:
(a) TGGCACACCCACCGTCACGAGAGCT (SEQ ID No. 11);
(b) TGGTTCAGGGTGACT (SEQ ID No. 13);
(c) AGGAGTGAGCCATGCCACC (SEQ ID No. 9); and
(d) CTGGGTCATTGATGACTGTTGTGTGG-GATACCTGCCGGG (SEQ ID No. 14).
Alternatively, (a) can be dGCTGGCACACCCACCGT-CACGAGAGCTTCC (SEQ ID No. 6),
(b) can be TTGGCACACCTGGGAGGATG (SEQ ID No. 7), (c) can be AGTGGTTCAGGGTGACTCT (SEQ ID No. 8), and (e) can be CTGGGTCATTGATGACTG (SEQ ID No. 10).

The invention is also directed to a DNA molecule selected from the group consisting of one or more of the following sequences:
(a) TGGCACACCCACCGTCACGAGAGCT (SEQ ID No. 11);
(b) TGGTTCAGGGTGACT (SEQ ID No. 13);
(c) AGGAGTGAGCCATGCCACC (SEQ ID No. 9); and
(d) CTGGGTCATTGATGACTGTTGTGTGG-GATACCTGCCGGG (SEQ ID No. 14).
Alternatively, (a) can be dGCTGGCACACCCACCGT-CACGAGAGCTTCC (SEQ ID No. 6),
(b) can be AGTGGTTCAGGGTGACTCT (SEQ ID No. 8), and (d) can be CTGGGTCATTGATGACTG (SEQ ID No. 10).

The invention is also directed to a recombinant DNA molecule having the following sequence TGGCACAC-CTGGGAG (SEQ ID No. 12).

The FIN-1 protein has been isolated and has a molecular weight of 50 kDa as determined by SDS-PAGE.

In addition to activating the syndecan promoter, this enhancer element has been shown to activate the SV40 promoter. The effect of the enhancer element on the SV-40 promoter can be seen in FIG. 21, where activation by the simultaneous administration of FGF-2 and TGF-β is observed. Therefore, FiRE is not syndecan-1 restricted and can be used with any suitable eukaryotic promoter, e.g., SV 40 promoter.

Figure 16:
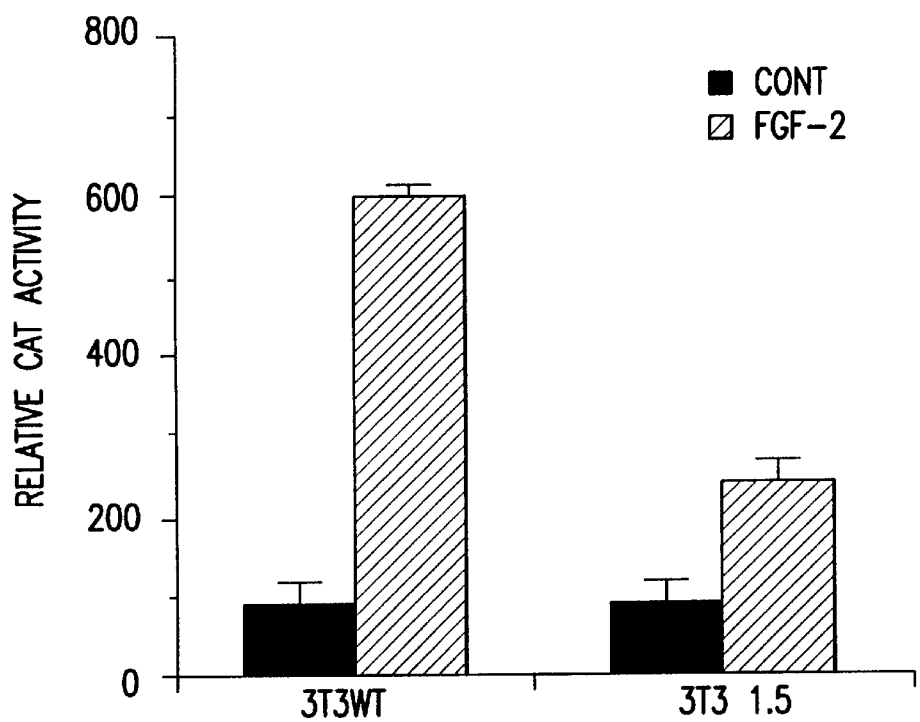

Several other growth factors were tested for the ability to activate the syndecan enhancer in pFiRE transfected 3T3NIH cells. FGF-2 showed clear enhancer activation. However, no significant enhancer activation was shown under these conditions with FGF-2, FGF-7, EGF, PDGF, or TGF-β. Other growth factors could be tested in a similar fashion. 5% fetal calf serum showed a slight stimulation of the enhancer. See FIG. 12. However, in cells expressing high levels of syndecan-1, enhancement activation is only slightly evident, as depicted in FIG. 16.

FCS, FGF-1, FGF-2, FGF-7, EGF, PDGF, and TGF-β were also tested for an increase in DNA synthesis by a 125-IdU incorporation assay. All showed a significant increase in DNA synthesis as represented in the bottom panel of FIG. 12.

Figure 17:
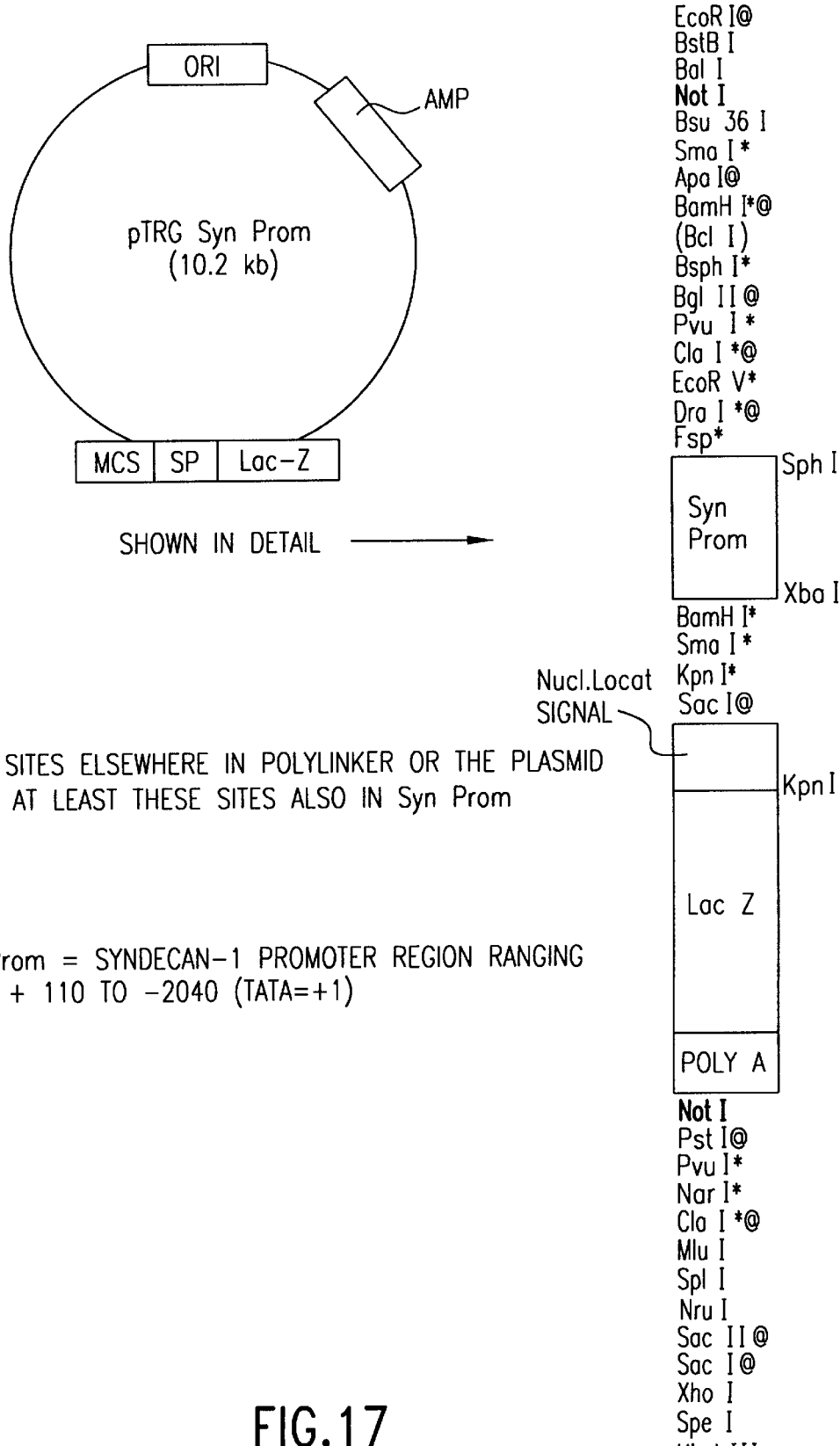
Figure 18:
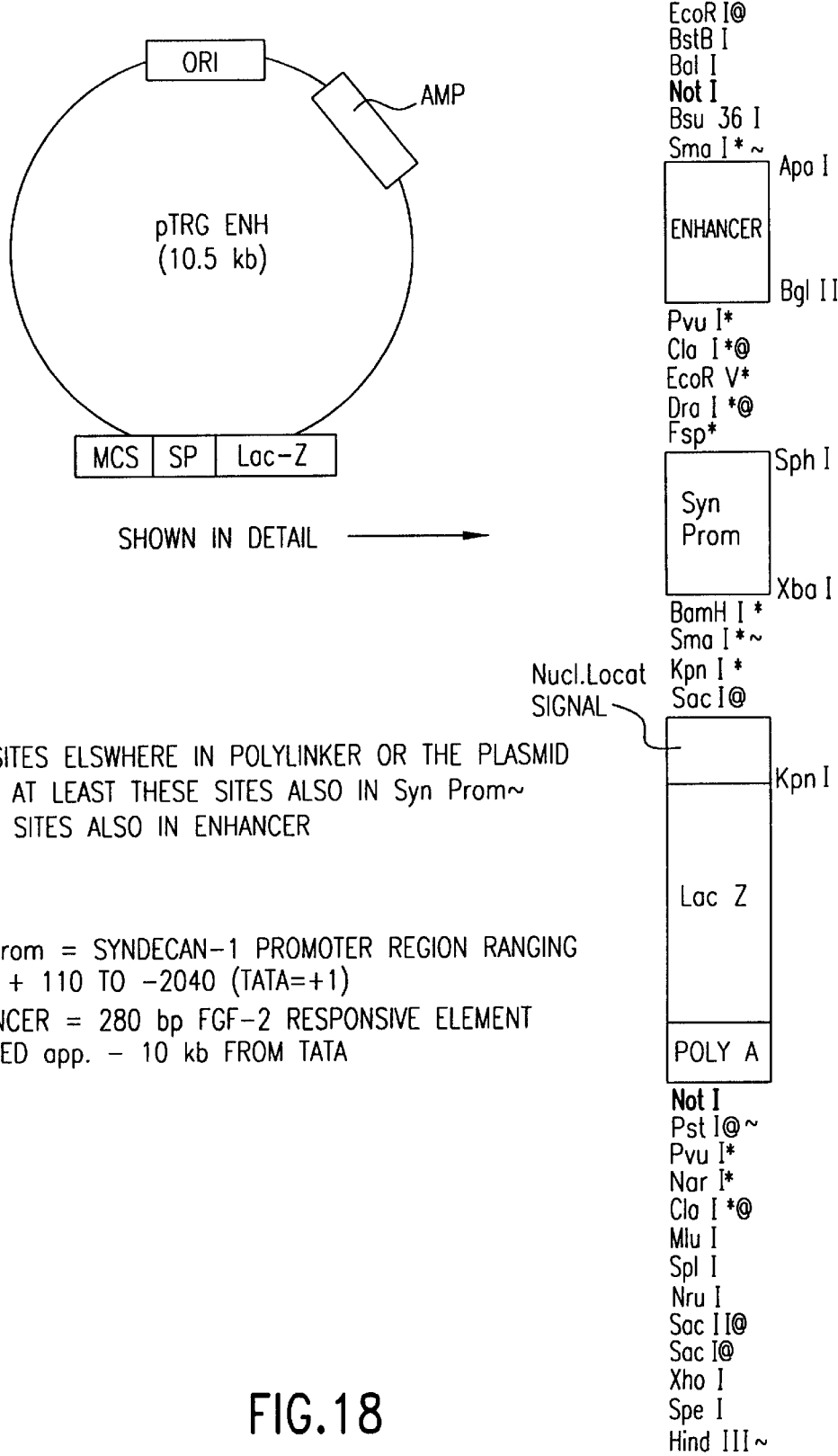
Figure 19A:
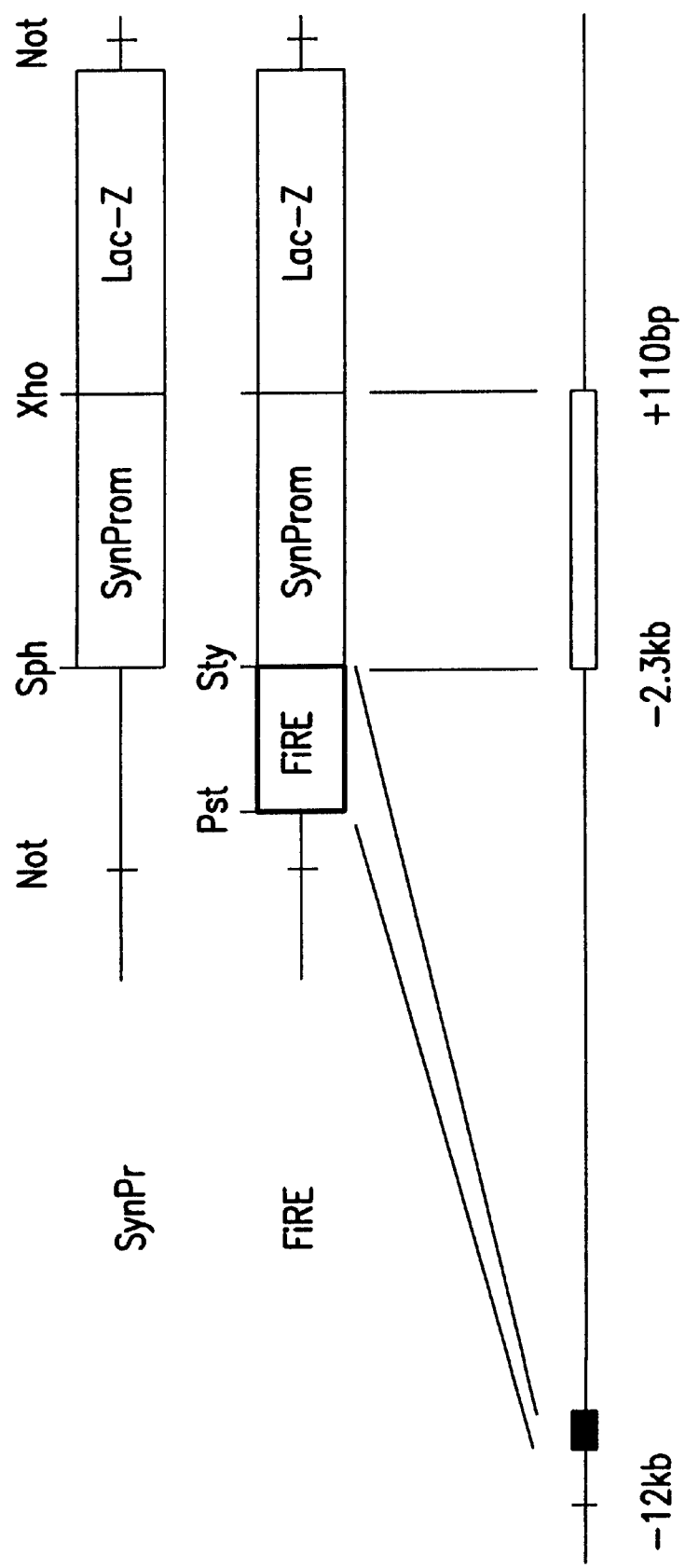
FIGS. 19A–F.
Figure 19B:
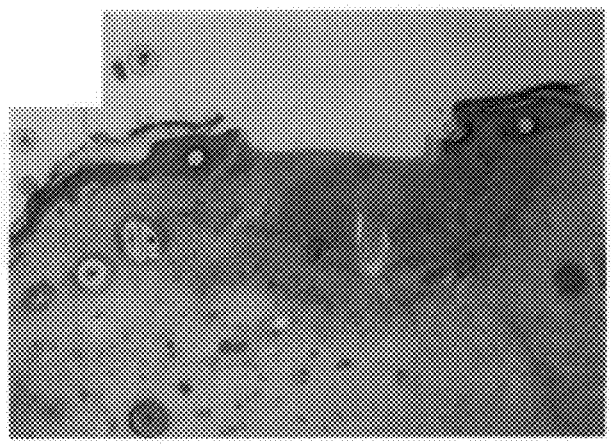
Figure 19C:
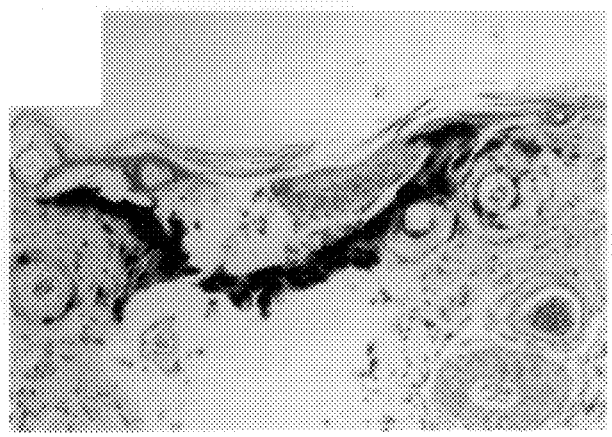
Figure 19D:
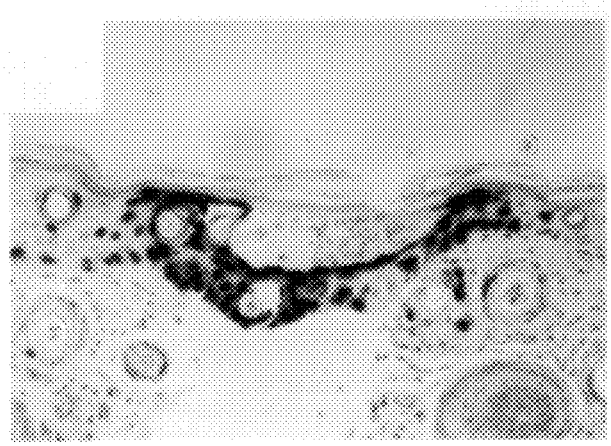
Figure 19E:
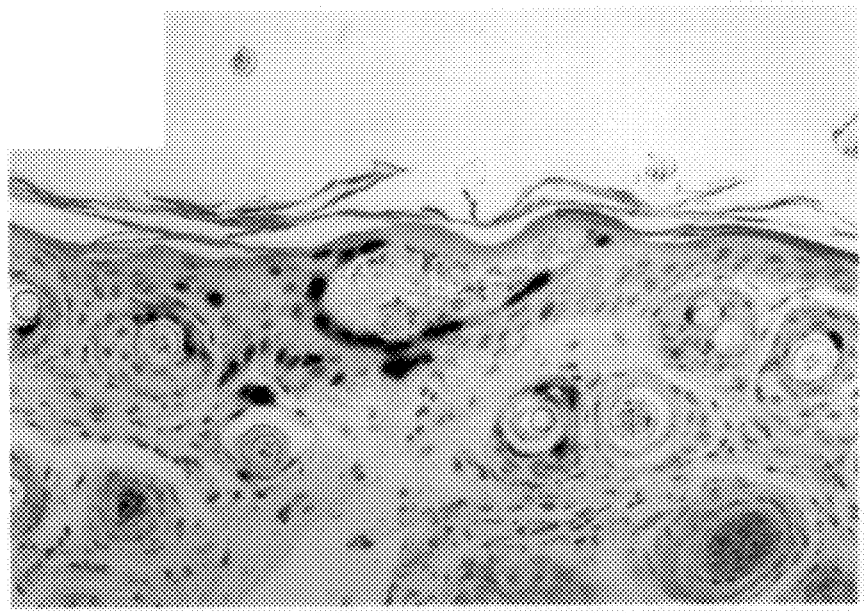
Figure 19F:
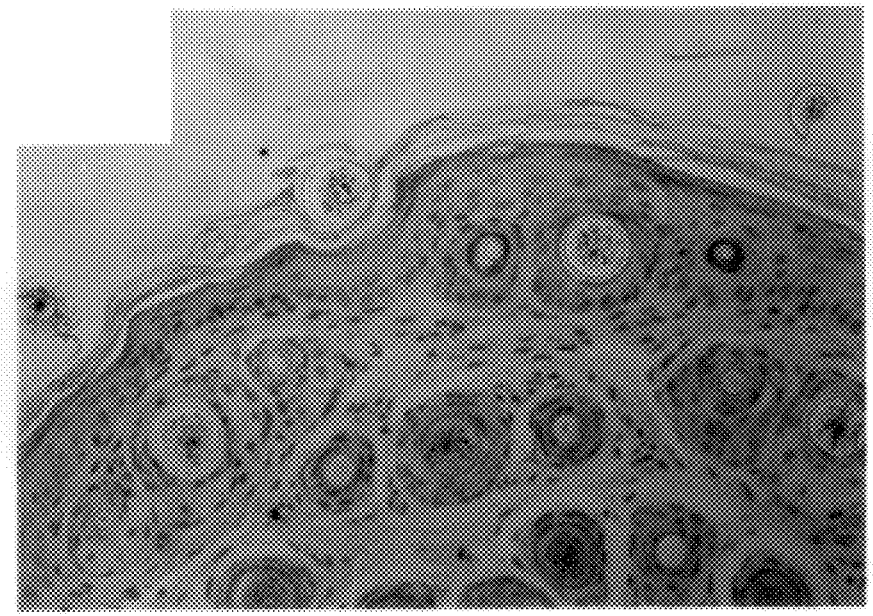
Figure 20A:
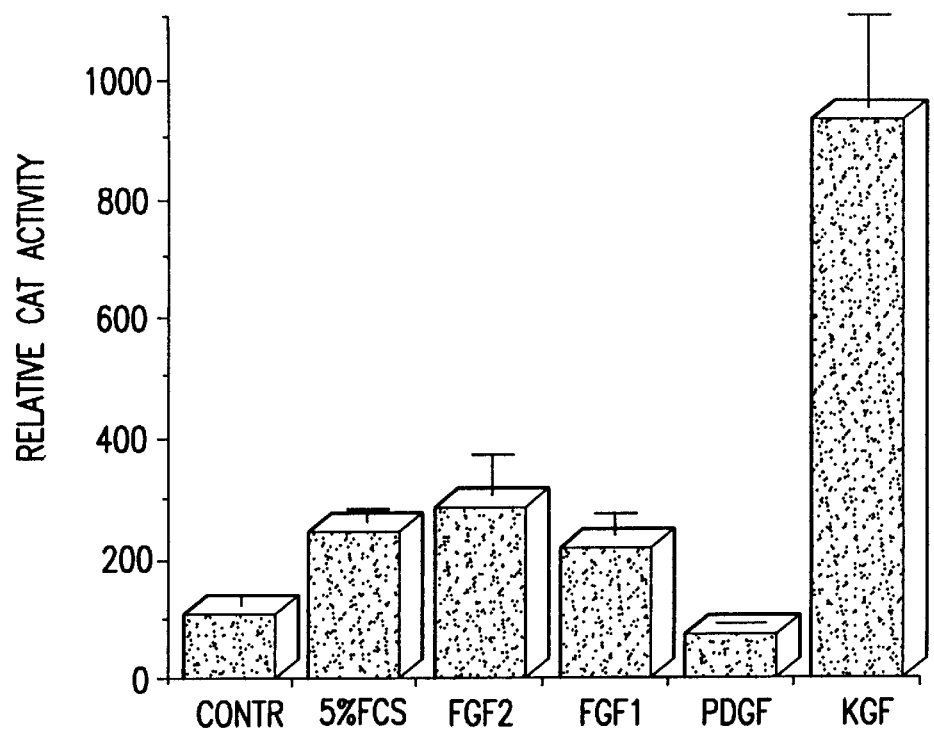
FIGS. 20a–c.
Figure 20B:
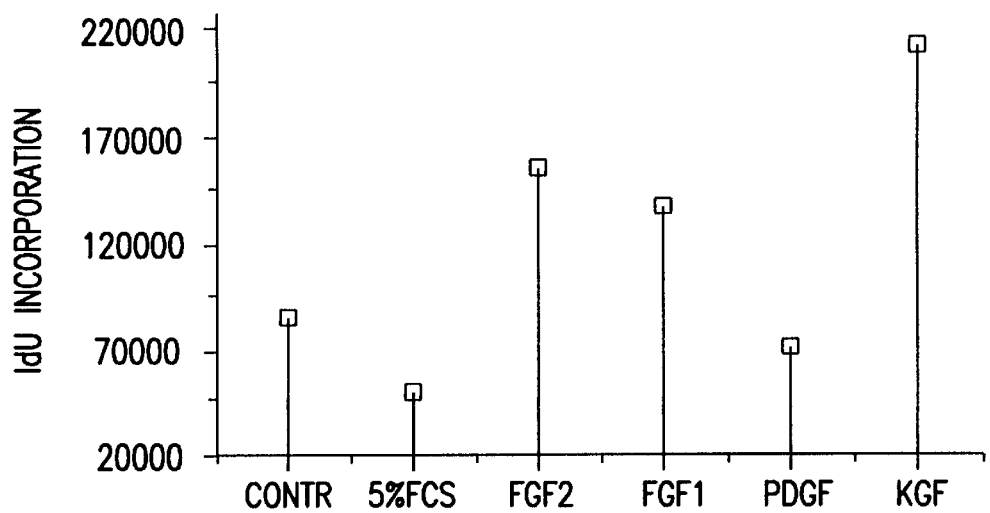
Figure 20C:
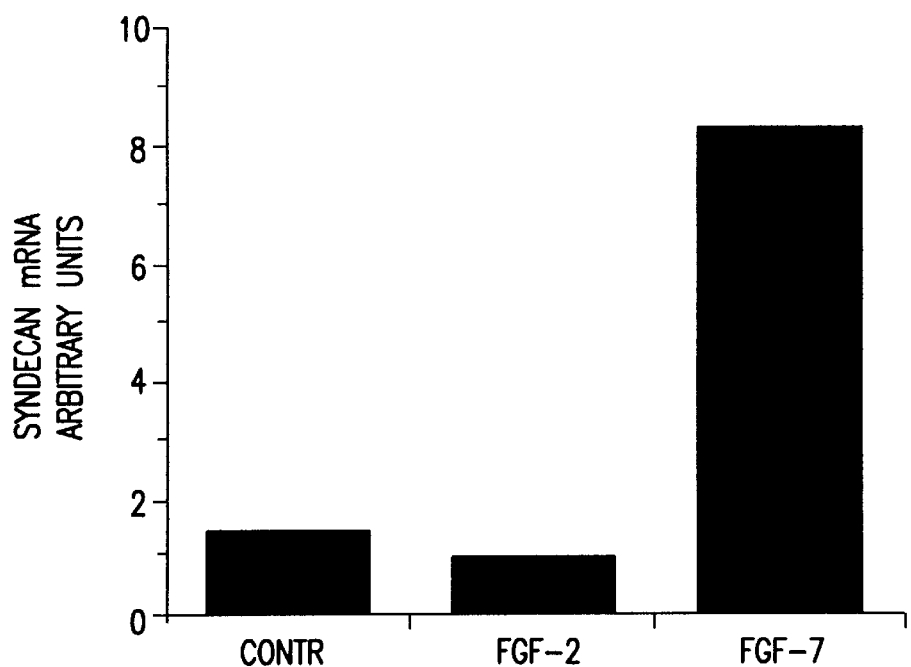

This invention also relates to transgenic non-human animals containing the syndecan enhancer operably linked to a promoter and to a structural gene inserted into this germ line. For example, transgenic mice were made containing the syndecan enhancer operably linked to the syndecan-1 proximal promoter and to β-galactosidase functioning as a reporter gene. The first plasmid, pTRGSynProm, contains a 2.25 kb XhoI-StuI restriction fragment comprising the syndecan-1 basic promoter region ligated to the β-galactosidase gene. The second plasmid, pTRGEnh, also contains the 2.25 kb XhoI-StuI restriction fragment ligated to the β-galactosidase gene. However, pTRGEnh also contains an additional 280 bp PstI-StuI restriction fragment containing the syndecan-1 enhancer inserted next to the basic promoter. Plasmid pTRGSynProm is depicted in FIG. 17, while pTRGEnh is depicted in FIG. 18.

These plasmids were transferred into pronuclei of fertilized mouse (FVB/N) oocytes by microinjection and the oocytes were transplanted into pseudopregnant mice (Hogan et al., *Manipulating the Mouse Embryo*, Cold Spring Harbor Lab. (1986)). Other transgenic animals can be made by appropriately modifying these procedures. For example, rat and bovine transgenic animals can be made. In the transgenic animals containing the syndecan enhancer, reporter gene activity was localized to wounds. Therefore, the enhancer element is associated with the targeting and/or differential expression of the target gene to wounds. By linking the syndecan enhancer to a gene of interest in transgenic animals expression of that gene can be targeted to wounds. Suitable promoters that can be incorporated into these constructs include the syndecan-1 promoter, the thymidine kinase promoter, the keratin-6 promoter, and the keratin-16 promoter. In particular embodiments of this invention, the gene of interest codes for a therapeutic, and the expression of this therapeutic at wound sites can be accomplished using an expression system containing the syndecan enhancer. Examples of suitable genes of interest include EGF and KGF.

Other experiments revealed the existence of a sequence element capable of suppressing gene expression (see FIG. 9). The suppressor was localized to nucleotides between −250 and −600 as shown in FIG. 2(a) (SEQ ID No. 1). DNA encoding the suppressor may be linked to recombinant constructs containing a promoter and a structural gene and may serve to suppress recombinant expression. Alternatively, methods may be devised for blocking the suppressive effect of this element in order to promote syndecan expression.

Manipulation of the upstream region of the syndecan gene can block its inactivation during malignant transformation. For example, replacement of the region in front of first exon of the syndecan gene with the glucocorticoid-inducible elements of mouse mammary tumor virus (MMTV) not only blocks syndecan suppression during malignant transformation, but also inhibits the ability or potential of cells to transform and become tumorigenic (FIGS. 5 and 6). These findings suggest a very important role for syndecan in the maintenance of normal epithelial morphology (Leppä et al., *Proc. Natl. Acad. Sci. USA* 89:932–936 (1992)).

Preferably, for treatment of humans and animals, a drug is administered that results in the enhancement of syndecan expression to levels sufficient to facilitate cellular differentiation in the degenerative stages of tissues. Such drugs are termed "syndecan-inducing agents." Syndecan-inducing agents include growth factors and the derivatives of such factors that retain growth-factor activity. Examples of such growth factors include FGF-2, and TGF-β, whether administered separately or together.

Figure 8:
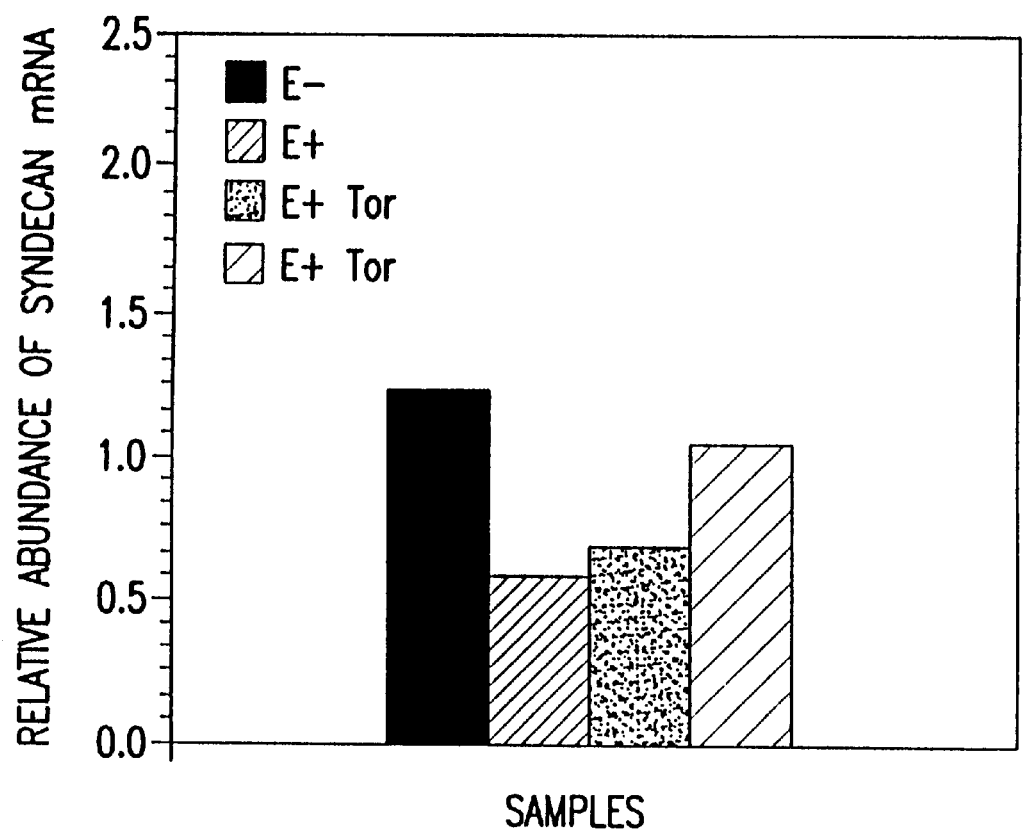

Even more preferred is a syndecan-inducing agent that has good tissue and cell penetration so that it can directly interfere with suppressor(s) of syndecan expression within cell nuclei. Such a syndecan-inducing agent is the antitumor drug toremifene. When toremifene, known to have good plasma membrane penetration, is administered to the hormone-transformed epithelial cells with reduced syndecan expression, the cells reverse their lowered syndecan expression, and evidence a syndecan level close to that observed in normal, non-transformed cells (FIG. 8). This demonstrates that syndecan-inducing agents useful in the methods of the invention are known and available and that such agents can specifically prevent cells from becoming malignant by blocking suppression of syndecan expression. Another useful drug in this regard is tamoxifen.

Syndecan-inducing agents may be administered using currently available preparations, or in any pharmaceutically acceptable vehicle. The route of administration may be any route that delivers efficacious levels of the drug to the desired active site, for example, by injection.

For parenteral administration, preparations containing one or more syndecan-inducing agents may be provided to the patient in need of such treatment in combination with pharmaceutically acceptable sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The syndecan-inducing agent of the invention can be employed in dosage forms such as tablets, capsules, powder packets, or liquid solutions for oral administration provided that the biological activity of the syndecan-inducing agent is not destroyed by the digestive process and that the characteristics of the compound allow it to be absorbed across intestinal tissue. Syndecan-inducing agents may also be administered by means of pumps, or in sustained-release form. The syndecan-inducing agents used in the method of invention may also be delivered to specific organs in high concentration by means of suitably inserted catheters, or by providing such molecules as a part of a chimeric molecule (or complex) which is designed to target specific organs.

Administration in a sustained-release form is more convenient for the patient when repeated injections for prolonged periods of time are indicated.

The composition containing the syndecan-inducing agent can be manufactured in a manner which is in itself known, for example, by means of conventional mixing, granulating, dragee-making, dissolving, lyophilizing or similar processes. The compositions of the present invention that provide the syndecan-inducing agent find utility in their ability to slow or prevent tumor growth or tumor reappearance. The syndecan-inducing compositions of the invention utilize the body's own mechanisms for promoting differentiation of specific cell types.

In intravenous dosage form, the compositions of the present invention have a sufficiently rapid onset of action to be useful in the acute management of tumor growth. Additionally, a low potency version is useful in the management of disorders wherein a tumor has been effectively treated and the patient appears to be in remission, but it is desired to maintain sufficient levels of syndecan-inducing agents in the patient so as to assist the body in preventing a recurrence of the tumor.

Typical doses of toremifene or tamoxifen, and other such syndecan-inducing agents useful in the methods of the invention for treatment of humans or other animals are 20–600 mg daily, and preferably 20–60 mg daily.

The Examples below are for illustrative purposes only and are not intended to limit the scope of the invention.

EXAMPLE I

Reversal of hormone-induced transformation by exogenous syndecan expression. As previously described (Leppä et al., *Cell Regulation* 2:1–11 (1991)), S115 mouse mammary tumor cells were routinely cultured in DMEM. For experimental studies involving hormone treatment, inactivated fetal calf serum (I-FCS) was replaced with 4% dextran charcoal-treated fetal calf serum (DCC-FCS), which eliminates endogenous steroids from serum, and used either with or without testosterone (10 nM) and with or without dexamethasone (10 nM or 1 $\mu$M). Cells were plated at a density of 10,000 cells/cm$^2$ and the medium was replenished every 3 days.

Plasmid pUC19-hsynpr7 containing human syndecan cDNA (Mali et al., *J. Biol. Chem.* 265:6884–6889 (1990)) was digested with NaeI restriction endonuclease, and the derived 336 bp long-fragment was separated in and eluted from low melting agarose gel. Plasmid pUC19-hsyn4 (Mali et al., *J. Biol. Chem.* 265:6884–6889 (1990)) was digested with NaeI and HindII (polylinker site), and the plasmid-containing fragment starting from base 487 was isolated. The NaeI fragment from hsynpr7 was ligated to the pUC-hsyn NaeI/HindII digested vector. The orientation of the insert was verified by restriction enzyme analysis and sequencing. The derived plasmid, containing the full coding region of human syndecan core protein, was named pUC19-hsynfull. This plasmid was further digested with BamHI and SphI (polylinker site). A fragment containing syndecan coding region bases 150–1461 was isolated and blunt-ended, using Klenow and T4 DNA polymerase. Finally, this fragment was ligated to SalI-linearized and blunt-ended pMAM-neo vector (Clontech; Palo Alto, Cailf.), resulting in a chimeric gene containing a RSV-MMTV-LTR promoter connected to the human syndecan coding region and to an SV-40 polyadenylation signal. The orientation was confirmed by restriction enzyme digestions. The plasmid was named pMAMneo-hsyn.

For control transfections, a 642 bp long-HindIII/PvuII fragment of the human growth hormone gene (consisting of exons 4 and 5; Bornstein et al., *J. Biol. Chem.* 263:1603–1606 (1988)) was blunt-ended and cloned into the same pMAMneo vector, as described above. This control construct was named pMAMneo-hGH.

All plasmids were isolated using the CsCl density gradient method. Before transfections, plasmids were linearized with AluI, chloroform/phenol extracted and ethanol precipitated.

Transfections were performed using Lipofectin™ (BRL), according to manufacturer's instructions. After selection for two weeks (G418; 750 $\mu$g/ml, Sigma), surviving clones were isolated from growth plates using cloning cylinders. The expression of human syndecan or growth hormone (consisting of exons 4 and 5) mRNAs was then confirmed by RNA isolation and Northern blot analysis. Clones expressing high levels of transfected genes were selected for further studies and characterizations. These stock cells were routinely cultured in the presence of G418 (300 $\mu$g/ml).

For the measurement of exogenous syndecan expression total RNA was isolated from wild-type S115 cells and cells transfected with human syndecan or growth hormone genes. RNA was extracted using 4M guanidine isothiocyanate and CsCl pelleting, as earlier described by Chirgwin et al., *Biochemistry* 18:5294–5299 (1979)). RNA from normal mouse mammary NMuMG and normal human mammary HBL-100 cells was used for comparison. RNA aliquots of 15 $\mu$g were separated in 1% formaldehyde agarose gels by electrophoresis and transferred to a GeneScreen Plus™ hybridization membrane (New England Nuclear). Blots were hybridized with multiprime (Amersham) labeled inserts of either mouse (PM-4) (Saunders et al.,*J. Cell Biol.* 108:1547–1556 (1989)) or human syndecan (pUC19-hsyn4 BamHI 1.1 kb fragment) (Mali et al., *J. Biol. Chem.* 265:6884–6889 (1990)), or with human growth hormone exons 4 and 5 (hGH) (Leppä et al., *Proc. Natl. Acad. Sci. USA* 89:932–936 (1992)) cDNAs, using the high stringency conditions suggested by the manufacturer of the membrane (New England Nuclear). All techniques based on modem molecular biology are fully explained in the literature such as in the laboratory manual entitled *Current Protocols in Molecular Biology*.

Anchorage independent cell growth was measured in a soft agar colony assay. The six well-plates were first covered with an agar layer consisting of 2 ml DMEM, 0.5% agar and 4% DCC-FCS. The middle layer contained 10$^4$ cells in 0.5 ml DMEM supplemented with 0.33% agar and 4% DCC-FCS, with or without 10 nM testosterone. The uppermost layer, consisting of medium (2 ml), was added to prevent drying of the agarose gels. The plates were incubated at 37° C. in 5% CO$_2$ for 12 days after which cultures were evaluated and photographed.

Tumorigenicity of S115 wild type cells, one hGH transfected control clone and two clones expressing human syndecan-1 was measured in nude mice. Cells were cultured in DMEM containing 5% FCS and 10 nM testosterone. After four days in culture, cells were harvested with trypsin, washed, and 10$^7$ cells suspended in 0.2 ml of DMEM were injected subcutaneously into the backs of athymic male nude mice (balb-C). A silastic testosterone capsule, which is known to increase the growth rate of S115 cells (King et al., *J. Steroid. Biochem.* 7:869–873 (1976)), was simultaneously implanted. Nude mice were examined regularly for tumor development and the size of the palpable tumors measured at intervals.

EXAMPLE II

Growth factors enhance syndecan expression. NMuMG mouse mammary epithelial cells and 3T3 (NIH) mouse fibroblasts were routinely cultured in bicarbonate-buffered Dulbecco's modified Eagle's medium (DMEM; GIBCO) containing 10% FCS (GIBCO) and antibiotics, as previously described (Elenius et al., *J. Biol. Chem.* 265:17837–17843 (1990)). For experiments, cells were plated at equal density on culture dishes (Nunc) and grown to 60–70% confluency.

Twenty-four hours before supplementing the medium with growth factor(s), the medium on the cells was replaced with fresh medium containing 2% CMS-FCS (Vogel et al., *Proc. Natl. Acad. Sci. USA* 75:2810–2814 (1978)). Equally treated cultures without growth factor addition served as negative controls. Porcine TGFβ1 (R&D), recombinant human bFGF (Boehringer) and murine EGF (Sigma) were used in final concentrations of 2.5 ng/ml (100 pM), 10 ng/ml (570 pM) and 1.2 ng/ml (200 pM) respectively, in all experiments. For quantitation and isolation of cell surface syndecan, media were discarded at time points indicated in the text and the cell layers were washed twice with ice cold phosphate buffered saline (PBS). Cells were scraped with a rubber policeman into ice cold PBS supplemented with 0.5 mM EDTA and centrifuged. After subsequent washes by resuspension and centrifugation the cell numbers were measured by counting the nuclei with a Coulter Counter (Coulter Electronics).

For quantitation of syndecan intercalated into the cell membrane, syndecan ectodomain was released by incubating washed cells in 20 μg/ml bovine pancreatic trypsin (Type III; Sigma) in PBS for 10 min on ice bath. After incubation the cells were centrifuged, leaving the ectodomain in the supernatant (Rapraeger et al., *J. Biol. Chem.* 260:11046–11052 (1985)). Sample volumes equal to 400,000 or 200,000 cells for 3T3 or NMuMG cells, respectively, were loaded onto a cationic nylon membrane (Zeta-Probe; BioRad) in a minifold-slot apparatus (Schleicher and Schuell), as previously described (Jalkanen et al., *J. Cell Biol.* 105:3087–3096 (1987)). Nonspecific binding was blocked by incubating the membrane for one hour at room temperature in PBS containing 10% FCS. Syndecan attached to the membrane was detected with a monoclonal antibody against mouse syndecan core protein (mAB 281–2) (Jalkanen et al., *J. Cell Biol.* 101:976–984 (1985)) that was radioiodinated by the chloramine-T oxidation method (St åhli et al., *Meth. Enzymol.* 92:242–253 (1983)). The membrane was incubated overnight at 4° C. with $^{125}$I-labeled 281-2 in PBS+10% FCS (10,000 CPM/ml). After five washes with PBS the bound antibody was visualized by autoradiography.

The accumulation of syndecan ectodomain into the medium was estimated by taking samples corresponding to 1/50 (3T3 cells) or 1/100 (NMUMG cells) of the total volume of the remaining medium at selected time points. The samples were analyzed by loading them onto a nylon membrane as described above. The autoradiography signal was quantitated with a GelScan XL ultroscan densitometer (LKB) using GelScan XL 2400 software (LKB).

For syndecan purification, cells were radiolabeled for 24 hours in low sulfate DMEM (MgCl$_2$ substituted for MgSO$_4$; 2% CMS-FCS) with 100 μCi/ml $^{35}$SO$_4$ (New England Nuclear) in the presence or absence of growth factor(s). Cell surface trypsin-releasable material was collected, as described above, and after dialysis against Tris-buffered saline (TBS), the sample was loaded onto a 281-2-Sepharose CL-4B immunoaffinity column (Jalkanen et al., *J. Cell Biol.* 105:3087–3096 (1987)). Bound material was eluted with 50 mM triethylamine (TEA) (pH 11.5) and the amount of radioactive PG in each fraction was analyzed using cetylpyridiumchloride-impregnated Whatman 3MM filter discs (Rapraeger et al., *J. Biol. Chem.* 260:11046–11052 (1985)). For interaction experiments, fractions containing most of the labeled PG were pooled and dialyzed against PBS.

To obtain unlabeled syndecan ectodomain for interaction assays (see below) the same procedure was used except that no radioactive sulfate was added to the culture medium and the syndecan containing fractions eluted from the immunoaffinity column were detected by immuno-dot assay using mAB 281-2. The estimation of the molar concentration of syndecan was based on the use of previously determined syndecan concentration by total amino acid analysis (Jalkanen et al., *J. Cell Biol.* 106:953–962 (1988)).

SDS-PAGE and Western Blot—For western blot experiments, cells were cultured 24 hours with or without growth factor(s). Syndecan ectodomain containing material released from the cell surface by trypsin treatment was fractionated on SDS-PAGE gradient (2–15%) gel (O'Farrel, *J. Biol. Chem.* 250:4007–4021 (1975)). After electrophoresis, samples were transferred onto a Zeta-Probe membrane by electroblotting with a 2005 Transphor apparatus (LKB). The syndecan antigen on the filter was detected with radioiodinated mAB 281-2 and the filter was washed, as described above for slot blot analysis.

Northern Blot—RNA was isolated from 3T3 and NMuMG cells using 4 M guanidine isothiocyanate and CsCl density centrifugation (Chirgwin et al., *Biochemistry* 18:5294–5299 (1979)). RNA samples were size-separated on a 1% agarose formaldehyde gel, transferred to a Gene-Screen Plus™ membrane (New England Nuclear) and hybridized with a multi-prime (Amersham) labeled partial cDNA clone for mouse syndecan (PM4) (Saunders et al., *J. Cell Biol.* 108:1547–1556 (1989)). After hybridization, the membrane was washed in 2× SSC and 1.0% SDS at 65° C. (high stringency conditions). For rehybridization with glyceraldehyde-3-phosphate-dehydrogenase (GAPDH; Fort et al., *Nucleic Acid Res.* 13:1431–1442 (1985)), the bound PM-4 probe was removed as recommended by the manufacturer of the filter (NEN).

EXAMPLE III

Induction of syndecan mRNA expression in human breast cancer cells (MCF-7) growth-inhibited with toremifene. The steroid-responsive human breast cancer cell line MCF-7 was used to study the expression of human syndecan under different growth conditions regulated by estrogen and anti-estrogen. Cells were plated at a density of 1.2×10$^6$ cells/100 mm of plastic culture dish and grown as monolayer cultures in 10 ml per dish of phenol red-free DMEM medium with 5% dextran/charcoal treated fetal calf serum (DS-FCS), 2 mM L-glutamine and 3 μg/ml insulin. For hormone-treatment, 1 nM of 17β-O-estradiol (E$_2$), alone or with 1–6.25 μM toremifene, dissolved in 70% ethanol, was added to the culture medium on the day following plating. The cells were cultured for 6 days, and the media were changed every second day. For RNA extraction, cells were washed in situ with PBS and scraped from the plates in 4 M guanidine isothiocyanate.

EXAMPLE IV

Treatment of Steroid-Responsive Tumors in Patients. Patients diagnosed as having a steroid-responsive tumor selected from a breast tumor, an endometrium tumor, a prostate gland tumor or a mesenchymal tissue tumor are administered a composition that contains efficacious amounts of the anti-steroid agent toremifene or tamoxifen, or efficacious amounts of the growth factor bFGF, TGF-β or bFGF together with TGF-β, in amounts ranging from 20–600 mg per day, depending upon the extent of the tumor, the patient's age, the patient's sex, and other treatments such as are taken into consideration in designing such chemotherapeutic protocols. The syndecan-inducing agent is administered for a period of time sufficient to increase syndecan levels in the tumor cells, such that the tumor cells now assume a more differentiated phenotype and such that the growth of the tumor is arrested or significantly slowed by the treatment.

EXAMPLE V

Stimulation of Hair Growth in Epidermal Skin Cells. Patients diagnosed as being in need of increased hair growth in the scalp region are administered a composition that contains efficacious amounts of the anti-steroid agent toremifene or tamoxifen, or efficacious amounts of the growth factor bFGF, TGF-β or bFGF together with TGF-β, in amounts ranging from 20–600 mg per day, depending upon the extent of the needed hair growth, the patient's age, the patient's sex, and other treatments such as are taken into consideration in designing such protocols. The syndecan-inducing agent is administered for a period of time sufficient to increase syndecan levels in the epidermal cells, such that hair growth is significantly increased by the treatment.

EXAMPLE VI

Determination of Mouse Syndecan Promoter and Enhancer Activities. The mouse syndecan-1 gene has been cloned and characterized up to −10 kbs upstream from the transcription start site. To determine the specific activities of different proximal promoter regions (up to −2 kbs from the start site) and enhancer regions (from −2 to −10 kbs) we have made plasmid constructs in which these regions were cloned into pCAT basic or pCAT promoter vectors, containing the CAT reporter gene. The reporter CAT gene produces the enzyme chloramphenicol acetyltransferase, which transfers the n-butyryl moiety of n-butyryl CoA to chloramphenicol. The n-butyryl chloramphenicol can be separated from native chloramphenicol by extraction with xylene.

For the proximal promoter, a deletion series was made (HindIII, HindII, BglII, StuI, DraI, ClaI, BamHI and PstI-XhoI) and the resulting fragments were cloned into the pCAT basic vector. For enhancer areas, three XbaI fragments were cloned into a pCAT promoter vector, where the SV 40 promoter was displaced by the BglII-XhoI fragment from the syndecan promoter.

The plasmid constructs were transiently transfected into eukaryotic cells by calcium phosphate precipitation simultaneously with a β-Galactosidase expressing vector to determine transfection efficiency. After a four hour incubation, cells were treated with 15% glycerol and grown for approximately 48 h in cell culture medium. Cells were then scraped from dishes in TEN-buffer and the cytoplasmic extract was obtained by repeated freezing and thawing. β-Galactosidase activity was obtained in the cytoplasmic extract by adding 0.1 M sodium phosphate, 45 mM mercaptoethanol and 0.2 mg O-nitrophenyl-s-galactopyranoside (ONGP). This was incubated from 2 hours to overnight and the color reaction was measured spectrophotometrically at 420 nm.

CAT activity was determined by adding 0.25 M Tris buffer, 25 ng n-butyryl CoA and 0.0626 μCi of $^{14}$C-chloramphenicol to the cytoplasmic extract. Samples were incubated overnight, extracted with xylene and the radioactivity present was measured by scintillation counting. CAT activity was corrected for transfection efficiency as determined by assays of β-galactosidase activity.

The cells used for proximal promoter constructs were 3T3 NIH, S115 (either hormone-treated or not) and nMuMG cells. For enhancer constructs we used 3T3 NIH cells grown in 2% CMS medium and MCA 3D cells grown in Ham's medium. 3T3 NIH cells were also used to test the effect of growth factors in 2% CMS medium with 10 ng/ml FGF-2 and 2 ng/ml TGFβ-1. MCA 3D cells were used to test the effect of 10 ng/ml KGF.

By measuring the CAT activity present in transfected cells, the effect of inserted syndecan gene regions on gene transcription was determined. Results indicated that both a suppressor element (FIG. 9) and an enhancer element (FIG. 10) are upstream of the syndecan transcription initiation site. The suppressor element is located between 250 and 600 base pairs upstream from the transcription initiation site. The enhancer element is located between 8,600 and 9,300 base pairs upstream from the syndecan transcription initiation site.

EXAMPLE VII

Activation of Syndecan-1 Gene Transcription FGF-2 in NIH3T3 Cells. Syndecan-1 expression is usually very low in mesenchymal cells if compared to epithelial cells. However, syndecan-1 expression can be transiently induced in many mesenchymes (Vainio et al., *Devel. Biol.* 134:382–391 (1989); Vainio et al., *Devel. Biol. Dev. Dyn.* 194:105–117 (1992)). Syndecan-1 expression is upregulated in 3T3 cells after 24 hr simultaneous FGF-2 and TGF-β exposure (See Elenius et al., *J. Cell Biol.* 114:585–595 (1991)).

Figure 11A:
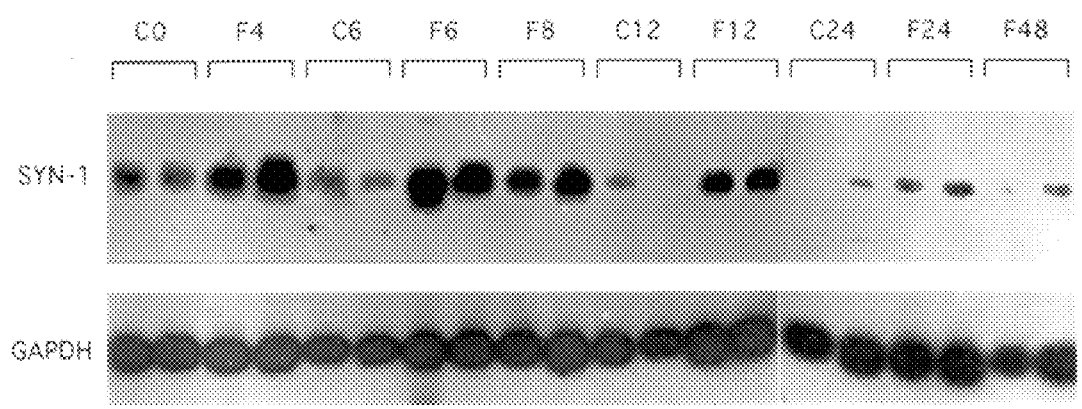
FIG. 11A.

To demonstrate that FGF-2 could alone activate the syndecan-1 gene, 3T3NIH cells were exposed to 10 ng/ml of FGF-2 for 0, 4, 6, 8, 12, 24 and 28 hrs to test the activation of the endogenous syndecan-1 gene. Following incubation with FGF-2, syndecan mRNA was isolated and quantified. Control incubations without FGF-2 were also performed. Syndecan mRNA was isolated and quantified without FGF-2 treatment following 6, 12, and 24 hr incubations. The quantification of syndecan mRNA production can be seen in FIG. 11A. GAPDH mRNA was used as a loading control. Based upon these data, syndecan expression is significantly enhanced (several fold) after 4 hrs of incubation with FGF-2. The enhancement appears to be maximal at about 6 hrs of FGF-2 incubation, and decreases thereafter. In the Figure, two individual exposures for each time point are presented.

Nuclear run-off experiments revealed that this upregulation was transcriptional. The same cells were exposed to 10 ng/ml of FGF-2 for 4 hours and 24 hours with or without exposure to FGF (Control) followed by the isolation of nuclei for the run-off experiment. c-jun or nur transcription was used as a positive control and β-actin as a loading control. In nuclei isolated 4 hours after FGF exposure the level of transcription of the syndecan-1 gene was elevated as were the levels for c-jun and nur as positive controls. The transcription of syndecan-1 was not detectable after 24 hours (FIG. 11), in agreement with the results of Northern hybridization.

This result suggests that the syndecan-1 gene is a direct target for an FGF-2 induced signal. Moreover, this targeting can be modulated by signals produced by other growth factors, like TGF-β, which alone cannot activate the syndecan-1 gene.

EXAMPLE VIII

FGF-induced Transcription of the Syndecan-1 Gene is Based on the Activation of a Far Upstream Enhancer. In order to characterize the transcriptional elements responsible for syndecan-1 expression following FGF-2 exposure, the 5'-region of the gene was cloned and sequenced 12 kb upstream from the TATA box.

The mouse syndecan gene was previously cloned and sequenced to −9.4 kb (See, supra; Vihinen et al., *J. Biol.*

Chem. 271:12532–12541 (1996)). To sequence further upstream an XbaI fragment (Xb6) from the cosmid clone was subcloned into pBluescript KS M13 (+/−) vectors (Stratagene). DNA sequencing was performed by the dideoxy chain termination method. Sequence data base comparisons were made with the Wisconsin package (Genetics Computer Group, Inc.) and the Transcription Factor Database (TFD). The sequence of Xb6 has been deposited at the EMBL Sequence Data Bank under accession number Z 22532 (SEQ ID No. 3).

Figure 11B:
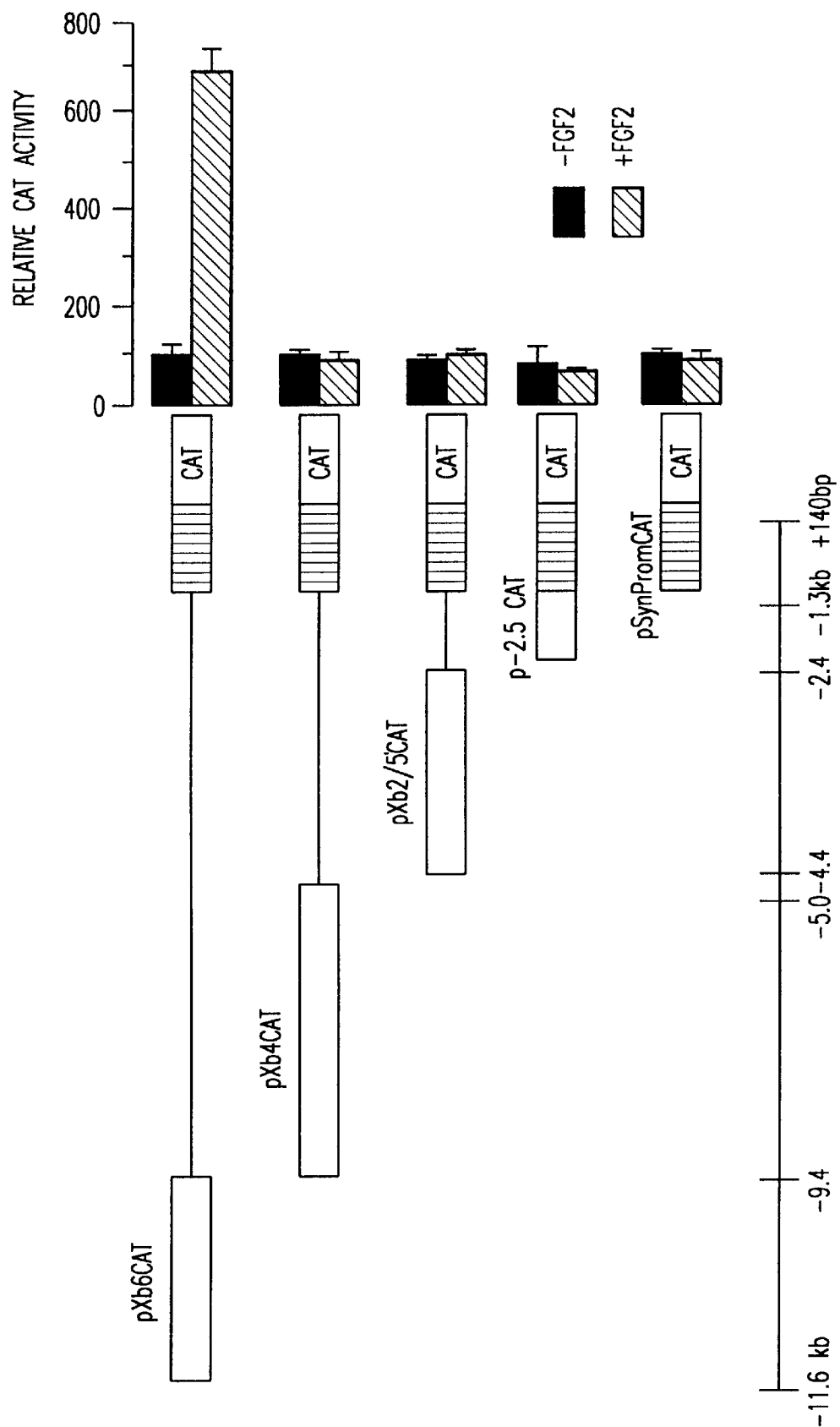
FIG. 11B.
Figure 11C:
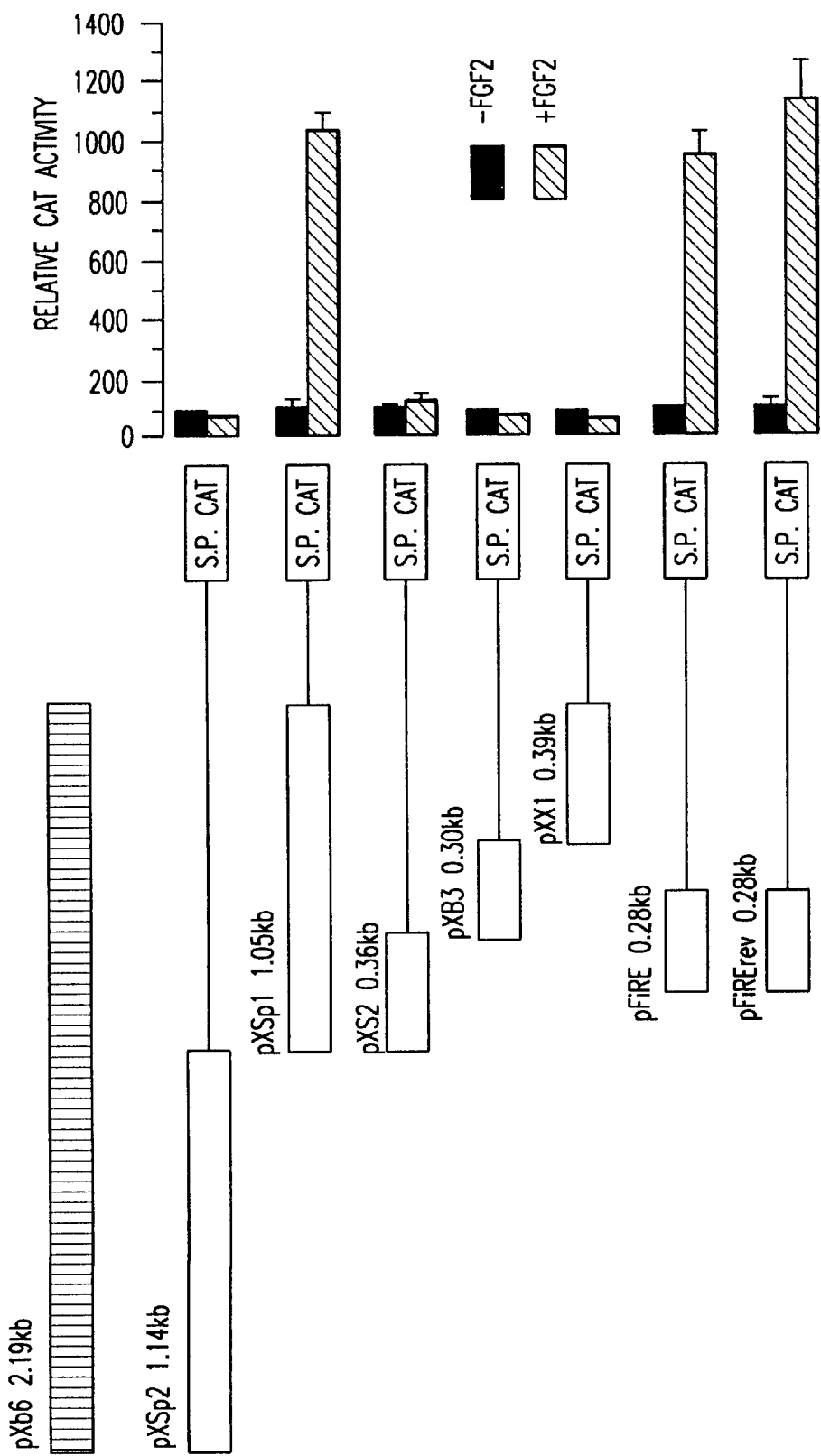
FIG. 11C.
Figure 11D:
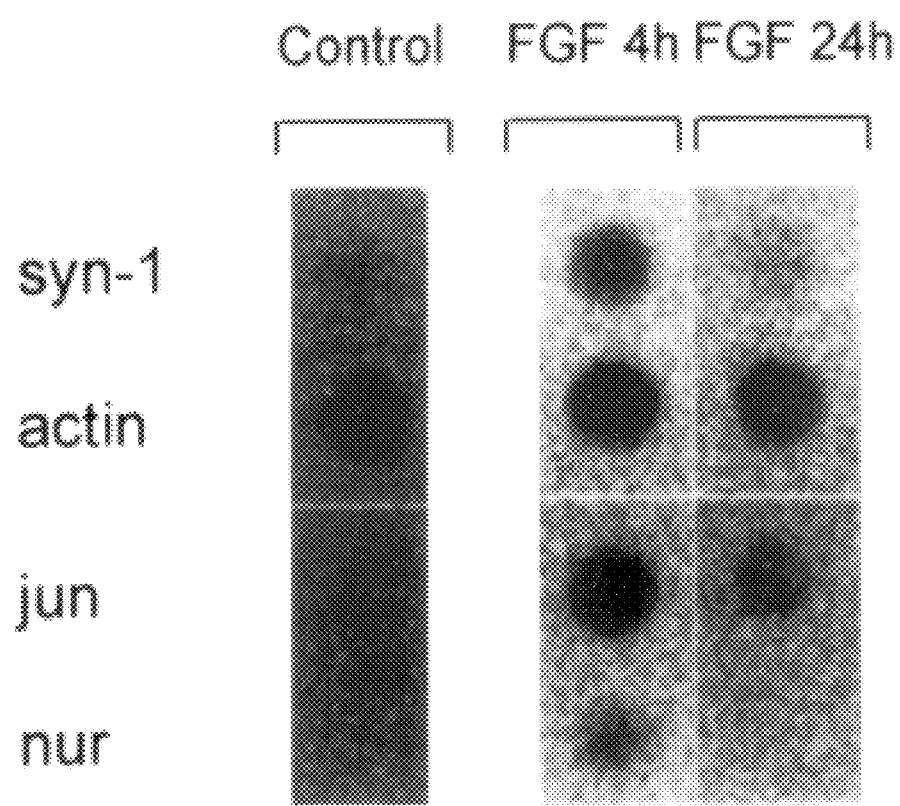
FIG. 11D.

Various constructs were made containing different fragments of the 11.5 kb syndecan upstream regulatory region together with the 1.1 kb segment containing the proximal promoter of the syndecan-1 gene. Plasmid pXb6CAT contains an XbaI fragment from −9.4 kb to −11.6 kb operably linked to the proximal promoter sequence, which in turn is operably linked to the CAT gene. Plasmid pXb4CAT contains an XbaI restriction fragment from −5.0 to −9.4 kb linked to the segment containing the proximal promoter, which is operably linked to the CAT gene. Plasmid pXb2/5' CAT contains anXbaI fragment from −2.4 kb to −4.4 kb linked to the segment containing the proximal promoter, which is operably linked to the CAT gene. Plasmid p-2.5 CAT contains a HindIII-XhoI fragment from −1.3 kb to −2.4 kb linked to the segment containing the proximal promoter, which is operably linked to the CAT gene. Plasmid pSyn Prom CAT contains no enhancer segment, but contains the proximal promoter segment operably linked to the CAT gene. The structure of these plasmids is shown in FIG. 11B. In each of these constructs the distance between the potential enhancer activity and the Syn Pro segment is conserved; about 2.5 kb separates the fragments containing the potential enhancer from the SynPro segment.

Each of these plasmids was transiently transfected into 3T3NIH cells, using the calcium phosphate precipitation method (Chen and Okayama, Mol. Cell Biol. 7:2745–2752 (1987)) as follows. For transient transfections NIH3T3 cells were plated at equal density on six-well plates (Falcon) two days before transfection. Plasmid DNA was transfected into cells by calcium phosphate method (Chen and Okayama, Mol. Cell Biol. 7:2745–2752 (1987)). A β-galactosidase expressing plasmid (pSV-β-galactosidase, Promega) was co-transfected with CAT constructs to monitor transfection efficiencies. Three parallel transfections were used in every assay. Directly after transfection growth factors were added, media change the next day and cells were harvested after two days. CAT activities were measured by liquid scintillation and β-galactosidase activities spectrophotometrically at 420 nm as described by Vihinen et al., J. Biol. Chem. 268:17261–17269 (1993)). As a control, other samples of the cells transfected with each plasmid were treated with buffer without FGF-2 for the same time periods. Only plasmid pXb6 responded to FGF-2 treatment with an increase in CAT gene expression. See FIG. 11B. The cells transiently transfected with the other plasmids showed no significant difference in CAT gene expression with FGF-2 treatment and without FGF-2 treatment. These results indicate that enhancer activity is localized to within the region between −9.4 kb to −11.6 kb upstream of syndecan transcription initiation site.

This region of the syndecan upstream regulatory region was further cleaved into smaller fragments and assayed similarly. See FIG. 11C. Specifically, plasmid pXSp2 contains a 1.14 kb XbaI-SphI restriction fragment from −11.6 kb to −10.5 kb. Plasmid pXSp1 contains a 1.05 kb SphI-XbaI restriction fragment from −10.5 kb to −9.4 kb. Plasmid pXS2 contains a 0.36 kb SphI-EarII fragment from −10.5 kb to −10.1 kb. pXB3 comprises a 0.30 kb EarI-EarI restriction fragment segment of the enhancer region from −10.1 kb to −9.8 kb of pXB6. pXX1 is a 0.39 kb EarI-XbaI restriction fragment of the enhancer region from −9.8 kb to −9.4 kb of pXb6. pFiRE comprises a 0.28 kb PstI-StyI restriction fragment of the enhancer region from −10.3 kb to −10.0 of pXb6. pFiRE$_{REV}$ contains the fragment of enhancer region from pXb6 inserted in the opposite orientation.

For the gene expression analysis the fragments of the syndecan-1 upstream region were subcloned from mouse genomic clones into the XbaI site of the pCATProm vector in which a mouse syndecan-1 promoter region (−1310 to +140) was fused to the CAT reporter gene (Vihinen et al., J. Biol. Chem. 271:12532–12541 (1996)). The pX-HIIICAT plasmid was prepared by cloning HindIII-XhoI promoter fragment (−2400 to +140 bp) into the promoterless pCAT basic vector (Promega). For pXSp1 and 2 plasmids, SphI fragments −11.4 to −10.5 kb and −10.5 to −9.4 kb, respectively) were deleted from pXb6CAT (−11.6 to −9.4 kb). Constructs pXS2, pXB3 and pXX1 were generated by ligating SphI-EarI/blunt (−10.5 to −10.1 kb), EarI/blunt fragment (−10.1 to −9.8 kb) and EarI/blunt-XbaI (−9.8 to −9.4 kb) from pXSpI into SphI-AccI/blunt, AccI/blunt or XbaI-SphI/blunt sites, respectively, into the pCATProm vector. Blunt ended fragments were made by T4 polymerase (Promega). For FiRE and FiRE$_{rev}$ a PstI-StyI/blunt fragment was subdloned into PstI-EcoRV or PstI-SmaI sites of the pBluescript vector and then transfected to Xba-SphI sites in pCATProm vector. These constructs were then used to transient transfect NIH3T3 cells as described supra, and CAT activity was measured.

The 280 base pair element inserted into pFiRE retained full FGF-2 dependent enhancement of CAT expression. See FIG. 11C. This enhancement was also maintained when the 0.28 kb fragment was inserted in the opposite orientation (pFiRE$_{REV}$). In addition, plasmid pXSp1, which encompasses the sequence of pFiRE, also exhibited a FGF-2 dependent enhancement in CAT expression. These results localize the enhancer element to a 280 bp region from nucleotide −10,280 to nucleotide −10,000 with the first nucleotide at the translation initiation site numbered as +1.

EXAMPLE IX

Effect of Various Growth Factors on Enhancer Activation in NIH3T3 Cells. Plasmid pFiRE was transfected into 3T3NIH cells as described, supra. The cells were starved in DMEM medium supplemented with 5% fetal calf serum to about 70% confluence. Fetal calf serum was then replaced with 2% carboxy-methyl-Sephadex eluted fetal calf serum (CMS) 12 hrs before adding the growth factors. Various growth factors in the same medium, 5% fetal calf serum (FCS) supplemented medium or a control containing the medium, without any added growth factors were incubated with the transfected cells for 2 days, and CAT activity was measured. The effect of 10 ng/ml of FGF-2, FGF-1, FGF-4, FGF-7 (KGF), EGF, IGF1, TGFα, IFNγ, and PDGF and 2 ng/ml TGF-β were tested. The human recombinant growth factors were purchased from Peprotech (FGF-1, −2, and −7), Boehringer (FGF-2) or from Calbiochem (PDGF) TGF-β was purchased from Sigma. The effect of the added growth factors and FCS on DNA synthesis was also tested by a 1 25-IdU incorporation assay. This cell proliferation assay was carried out by incubating cells for 4–6 hrs with 0.25 μCi/ml 5-[$^{125}$I]iodo-2'-deoxyuridine (IdU, Amersham), washed several times with PBS and solubilized in 1 M NaOH. Radioactivity was measured using a gamma counter (Wallac).

Figure 12A:
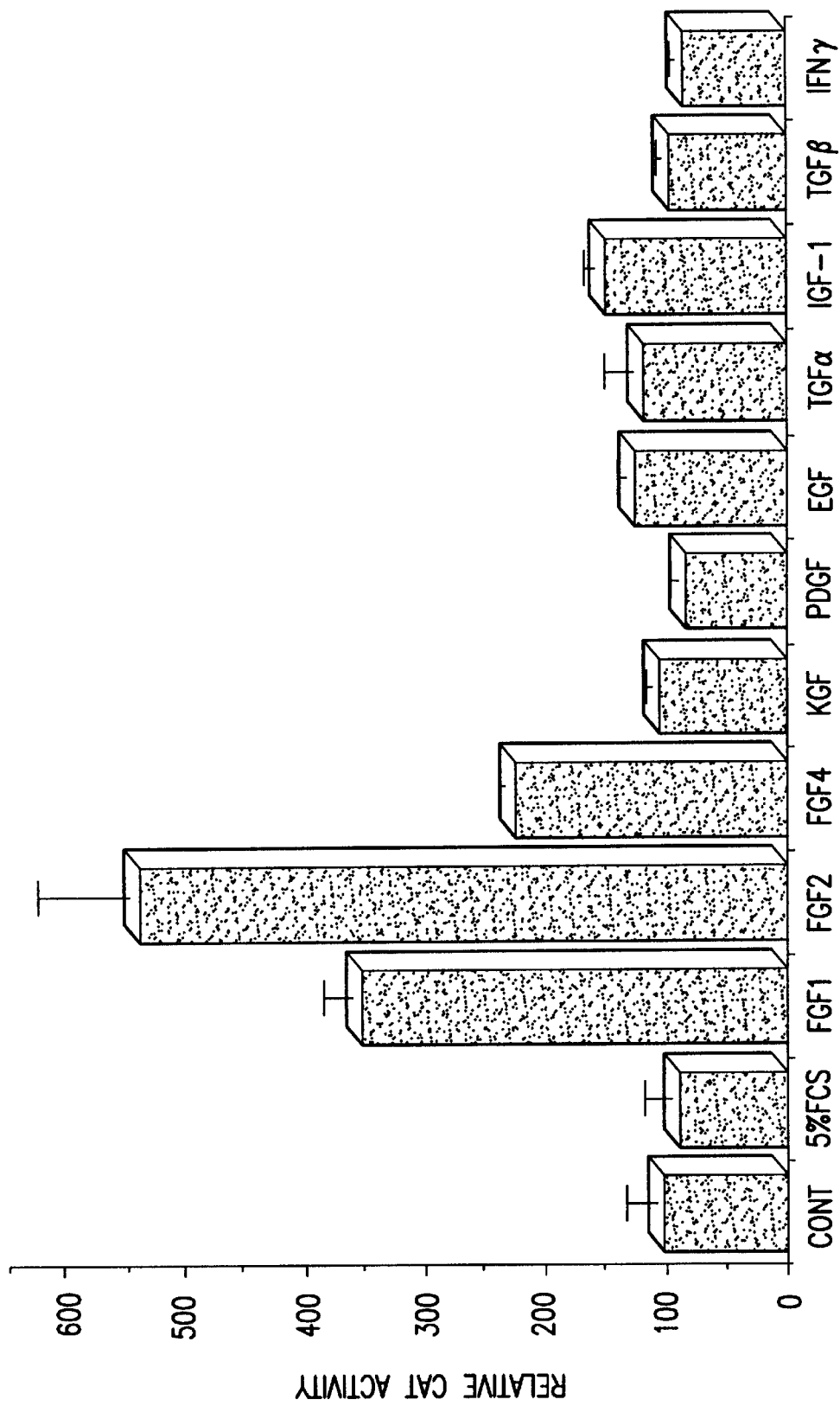
Figure 12B:
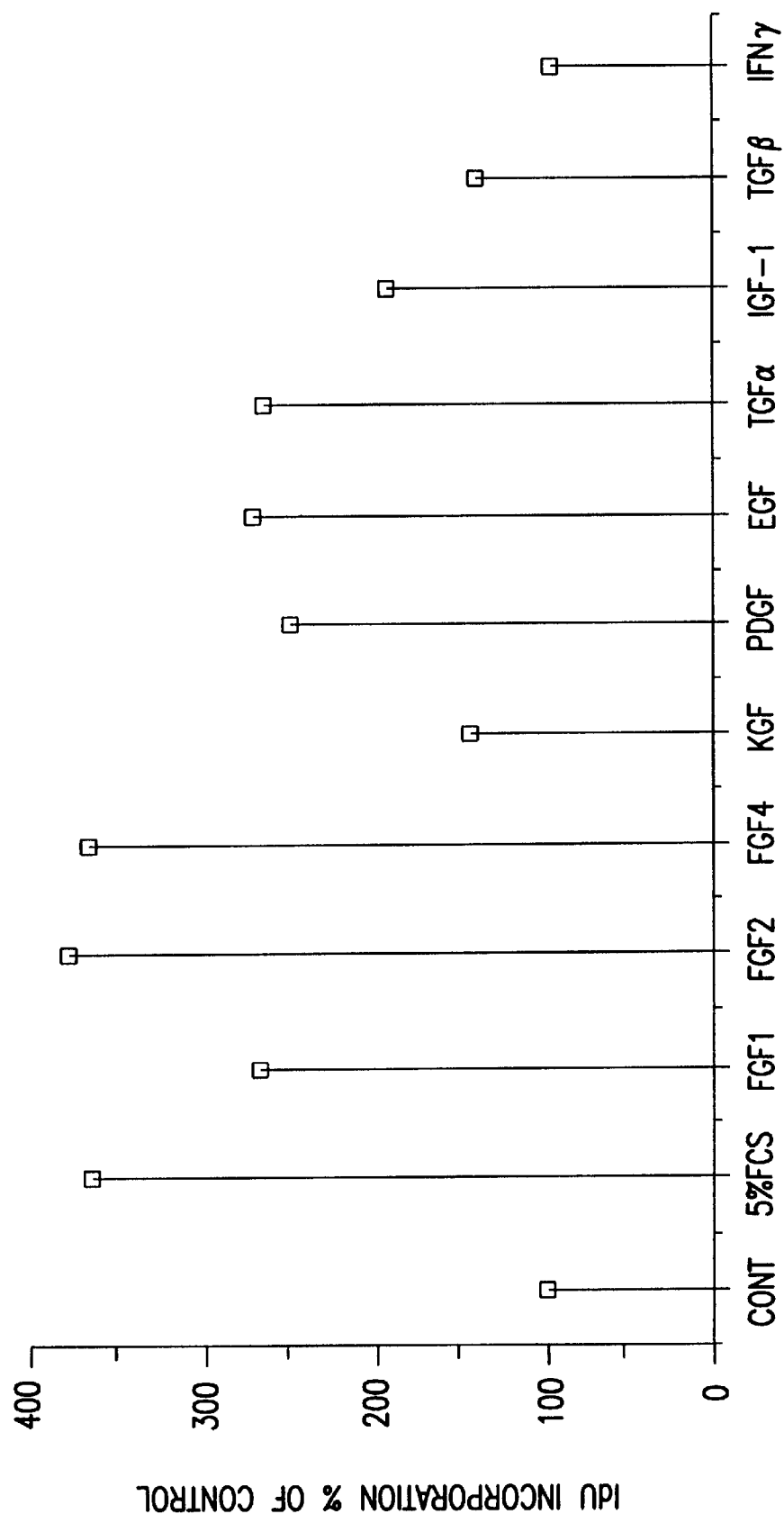

The results of this experiment are reported in FIG. 12. The results indicate that all of the tested growth factors significantly increase the level of incorporation of 125-IdU above that of the control, indicating that the growth factors were taken up by the transfected 3T3 NIH cells and were functional (FIG. 12B). Although all of the growth factors known to act on 3T3 cells stimulated 3T3 proliferation, FGFs were the only growth factors to clearly increase reporter gene activity (FIG. 12A). FGF-1 and FGF-4 had a lower effect those FGF-2 (FIG. 12A). FGF-7, known to act only on epithelial cells, had no effect. Some FGF-1 preparations, from the different commercial sources, lacked the ability to activate FiRE, while still inducing cell proliferation. Only FGF-2 revealed clear enhancer activation. However, 5% FCS slightly stimulated the enhancer.

In addition, 5% FCS only induced a small response despite containing several growth factors. PDGF, IGF and EGF enhanced cell proliferation to a similar extent as FGF-2, but had no effect on enhancer activity. Thus, stimulation of different tyrosine kinase receptors does not lead to activation of FiRE, nor does proliferation alone correlate with activation of FiRE. Consequently, FiRE cannot be regarded as a simple proliferation related target of growth factors.

Figure 12C:
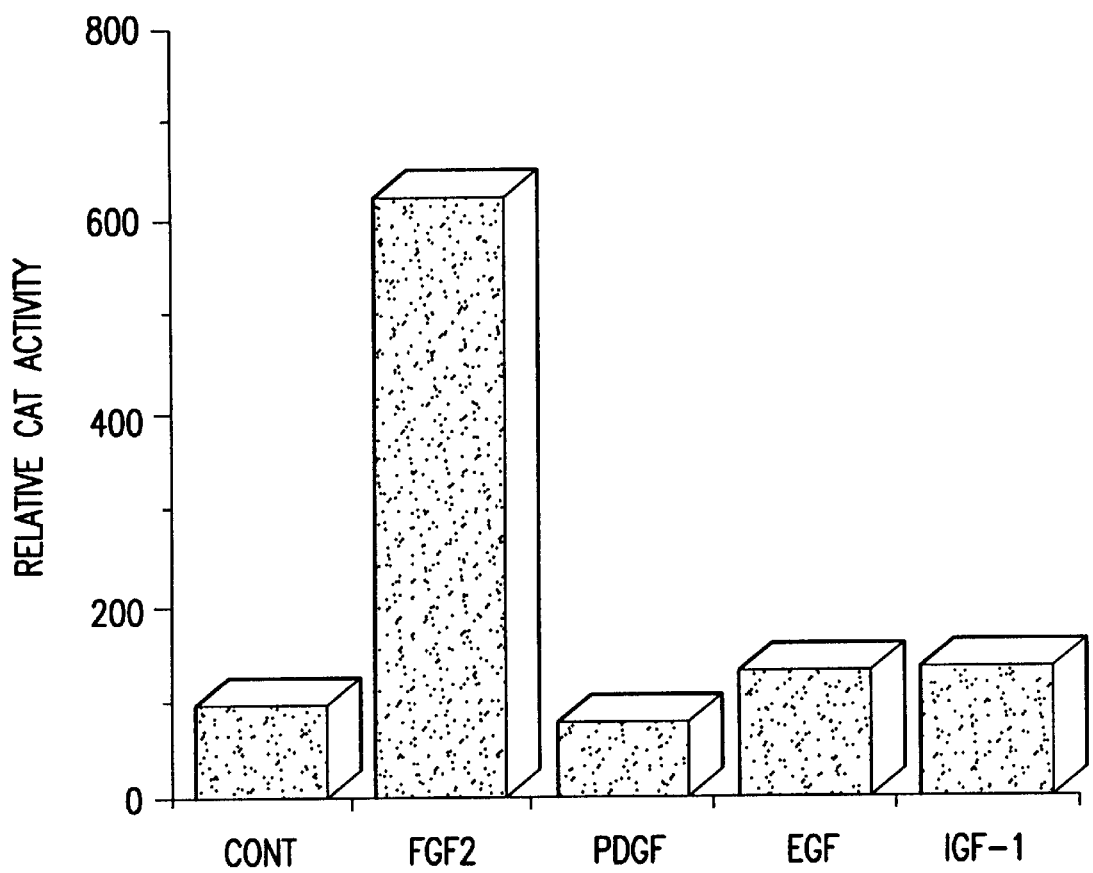

As the original construct contained over 1 kb of syndecan-1 proximal promoter, we wanted to rule out the possible suppressive action of this basal promoter on the function of the other growth factors. Therefore, nearly all of the promoter was deleted, leaving only 98 bp of the proximal promoter (p-271 CAT), which included only the putative TATA-box without any upstream regulatory elements (Vihinen et al., 1996). As shown in FIG. 12C the removal of the syndecan promoter had no effect on the pattern of growth factor induced FiRE activation, indicating that the growth factor specificity is not regulated by the proximal promoter.

EXAMPLE X

The Enhancer Comprises Five DNA Binding Motifs. Plasmid pFiRE was end-labeled using Kienow fragment and $\alpha^{22}$PdCTP. DNAse I footprinting was performed with labeled pFiRE vector alone (naked), together with FGF-induced nuclear extracts (FGF-2), and together with non-induced nuclear extracts (control). To obtain nuclear extracts, NIH3T3 cells were plated on 16 cm dishes and treated with or without FGF-2 for 1 day. Nuclear proteins were extracted using a modification described by Lee et al., Gene Anal. Techn. 5:22–31 (1988). Protein concentrations were measured by the Bradford method.

For footprinting, pBluescript containing pFiRE was cut with HindIII, end-labeled with [$\alpha^{32}$P]dCTP using Klenow DNA polymerase (Promega) and digested with XbaI. The labeled and PAGE purified DNA was incubated for 10 minutes at room temperature with about 40 mg of crude nuclear extract, 2 μg of poly-3[I-C] (Boehringer Mannheim) in a reaction buffer (10 mM TrisCl, pH 8; 5 mM MgCl$_2$, 1 mM CaCl$_2$, 2 mM DTT, 50 mg/ml BSA and 100 mM KCl) containing 0.1 or 1 unit of DNAseI (Boehringer Mannheim). The reaction was stopped after 2 minutes. A chemical G+A sequencing ladder (Maxam & Gilbert, Meth. Enzymol. 65:499–560 (1980)) was run along with the digestion products on a 6% sequencing gel. The results are shown in FIG. 13. Five footprinted motifs ranging from 14 to 38 bp in length in close proximity to each other and covering a total of 170 bp were revealed and are marked with numbered boxes. Binding of nuclear factors to motifs 3, 4 and 5 appear to be FGF-2 dependent, whereas binding to motifs 1 and 2 appear to be FGF-2 independent. The A+G sequence of pFiRE was run alongside the footprinting ladders.

EXAMPLE XI

Sequence of the FGF-2 Inducible Enhancer. The 280 bp fragment of pFiRE containing the syndecan enhancer was sequenced. This sequence is depicted in FIG. 13B. The footprinted motifs observed in Example X are underlined. It was determined that these footprinted motifs together restore 50–70% of the original enhancer activity. The sequence of motif 3, which contains the binding site for FGF-inducible nuclear factor FIN-1, was compared to consensus binding sites for transcription factors. No significant homology between this motif and the consensus sequences was observed.

EXAMPLE XII

The Enhancer is Bound by FGF-2 Inducible and Non-inducible Nuclear Factors. Gel retardation analysis for each enhancer motif (1–6) was performed with double-stranded oligonuceotides.

The double-stranded oligonucleotides were end-labeled with [$\alpha^{32}$P]dATP (ICN Biomedicals) by the polynucleotide kinase (Promega). The sequence of these oligonucleotides is:

| Motif | Sequence |
|---|---|
| 1 (SEQ ID NO:16) | 5'-dGCTGGCACACCCACCGTCACGAGAGCTTCC-3' |
| 2 (SEQ ID NO:17) | 5'-TTGGCACACCTGGGAGGATG-3' |
| 3 (SEQ ID NO:18) | 5'-AGTGGTTCAGGGTGACTCT-3' |
| 4 (SEQ ID NO:19) | 5'-AGGAGTGAGCCATGCCACC-3' |
| 5 (SEQ ID NO:10) | 5'-CTGGGTCATTGATGACTG-3' |

In a 12 μl reaction, 5 μg of the nuclear extracts were incubated with labeled oligonucleotide, 2 μg of poly-d[I-C] and 2× reaction buffer, i.e., 30 min Tris, pH 7.5; 100 mM NaCl; 2 mM EDTA; and 10% glycerol for 15 minutes at room temperature. Non-labeled competitor oligonucleotides were used at 100-fold molar excess. The complexes were analyzed by electrophoresis in a 4.5% polyacrylamide gel. For supershifts, 0.1 μg of specific antibody was added to the reaction 15 minutes before the labeled oligonucleotide.

Each motif element was treated with nuclear extracts derived from FGF-2 treated (f or FGF) or untreated (C or control) 3T3 cells. An SPI consensus oligo was used as a control to test the functionality of the nuclear extracts. The results are given in FIG. 14A. Binding of at least two protein complexes for each motif were observed. The results indicate that enhancer motifs 3, 4 and 5 bind to a factor present in nuclear extracts from FGF-2 treated 3T3 cells. However, binding of enhanced proteins to motifs 1 and 2 were evident in stable FGF-2 stimulated and nonstimulated 3T3 cells.

Figure 14A:
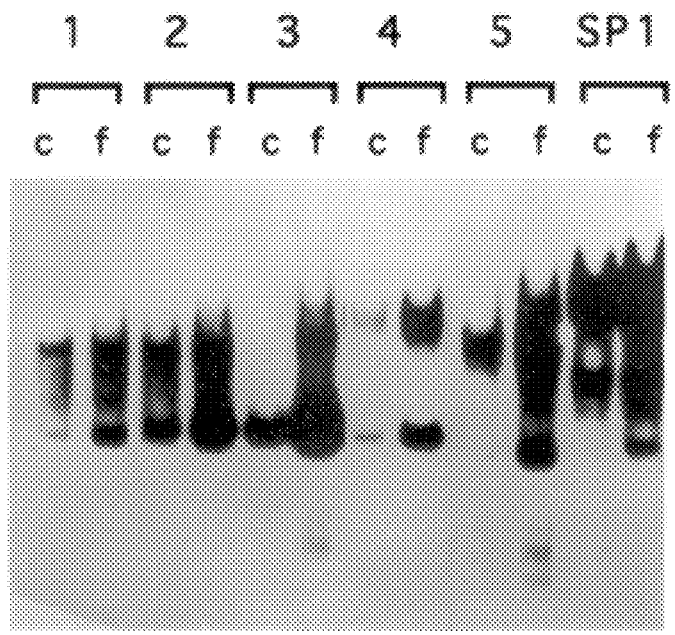
FIGS. 14A–F.
Figure 14B:
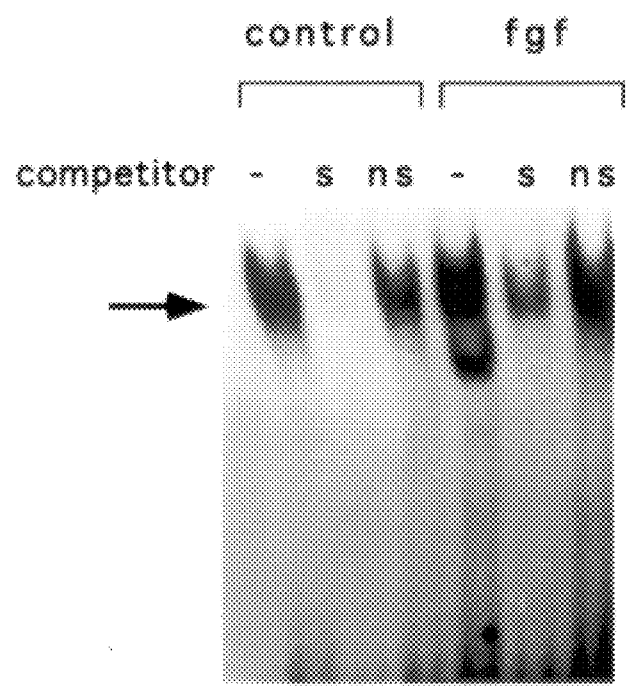
Figure 14C:
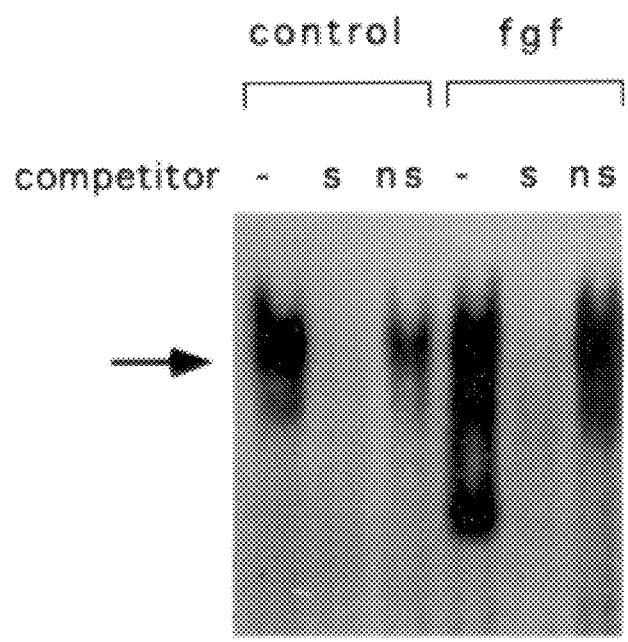
Figure 14D:
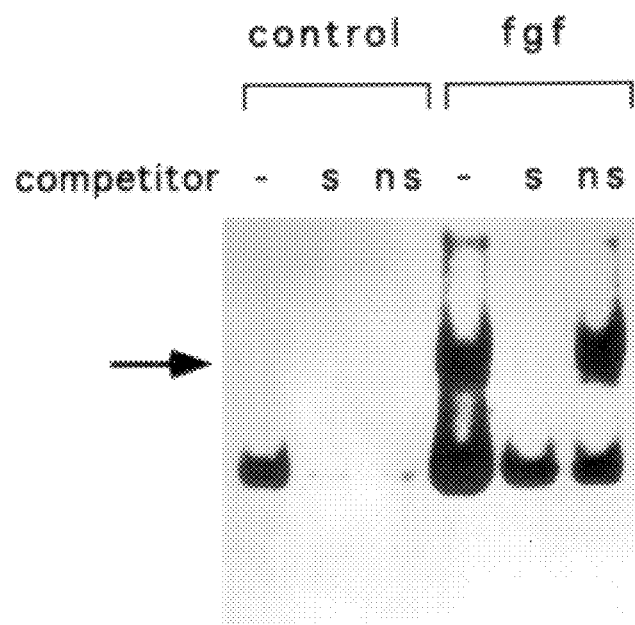
Figure 14E:
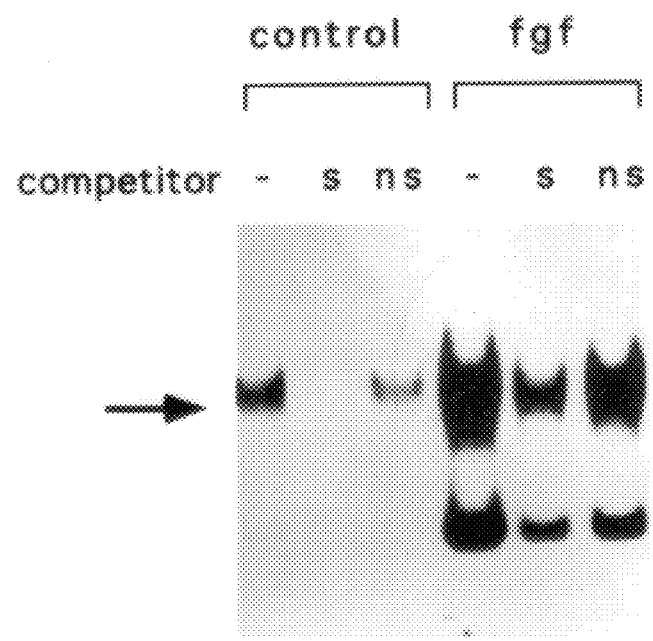
Figure 14F:
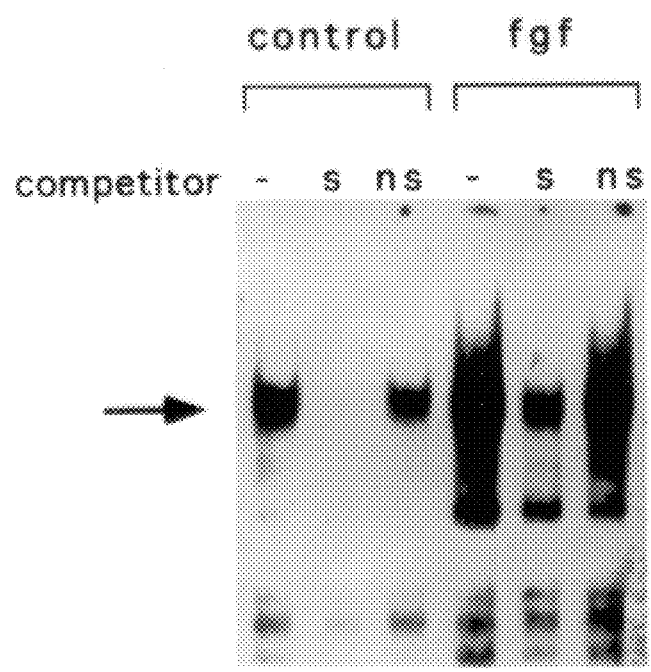

These motifs was further analyzed by competing the binding of nuclear factors with a molar excess of specific (s) and non-specific (ns) oligonucleotides. The non-specific oligonucleotide for motifs 3, 4 and 5 was the motif-1 sequence, while the non-specific oligonucleotide for motifs 1 and 2 was the motif 3 sequence. The resulting complexes were analyzed by the gel retardation analysis described above. The results are depicted in FIGS. 14B (motif 1), 14C (motif 2), 14D (motif 3), 14E (motif 4) and 14F (motif 5). Specific binding is indicated by an arrow. The result indicated that all motifs shifted at least one specific band in the gel retardation assay. The results also show that motifs 3, 4, and 5 bind at least one specific FGF-2 inducible nuclear protein. Motifs 1 and 2 do not show binding to an FGF-2 inducible factor. From these results it can be concluded that all 5 motifs are in use. Motifs 1 and 2 are occupied constitutively by nuclear proteins, while motifs 3, 4, and 5 are occupied only after FGF exposure of 3T3 cells.

EXAMPLE XIII

Figure 21:
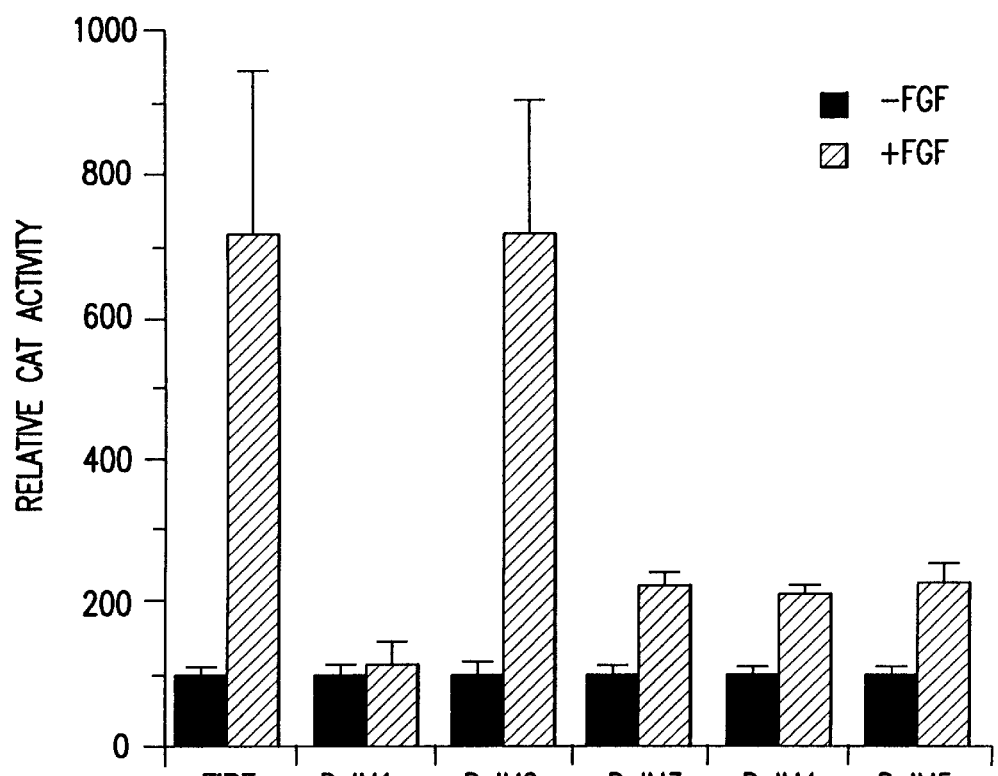
FIG. 21.

Deletion Mutants of FiRE. To determine whether all binding sites are required for enhanced activation, deletion mutants for each motif were generated by PCR. For motif 1, the 3' end of FiRE was deleted by generating a PCR product ranging from the 5' end of FiRE to motif 2. For motif 2, the E-Box was replaced by aKpnI restriction site. For motifs 3 and 4, a central 10 bp sequence was replaced with a 10 bp SpeI restriction site. For motif 5, a PCR product from motif 4 to motif 1 was generated. The mutant DNA was ligated into a CAT reporter plasmid as described supra. Cells were treated with FGF-2 and CAT assays were performed as described. The results of this experiment are depicted in FIG. 21. The modification of motifs 1, 3, 4 and 5 resulted in the loss of a significant reduction of FiRE transcriptase activation. However, the modification of motif 2 has little or no effect on transcriptional activation. This result supports the involvement of 4 of the 5 motifs in the activation of FiRE by FGF. Furthermore, it shows that at least two fos-jun complexes (AP-1) are required, but alone they are not sufficient to activate FGF induced transcription.

Figures 22A, 22B, 22C, 22D:
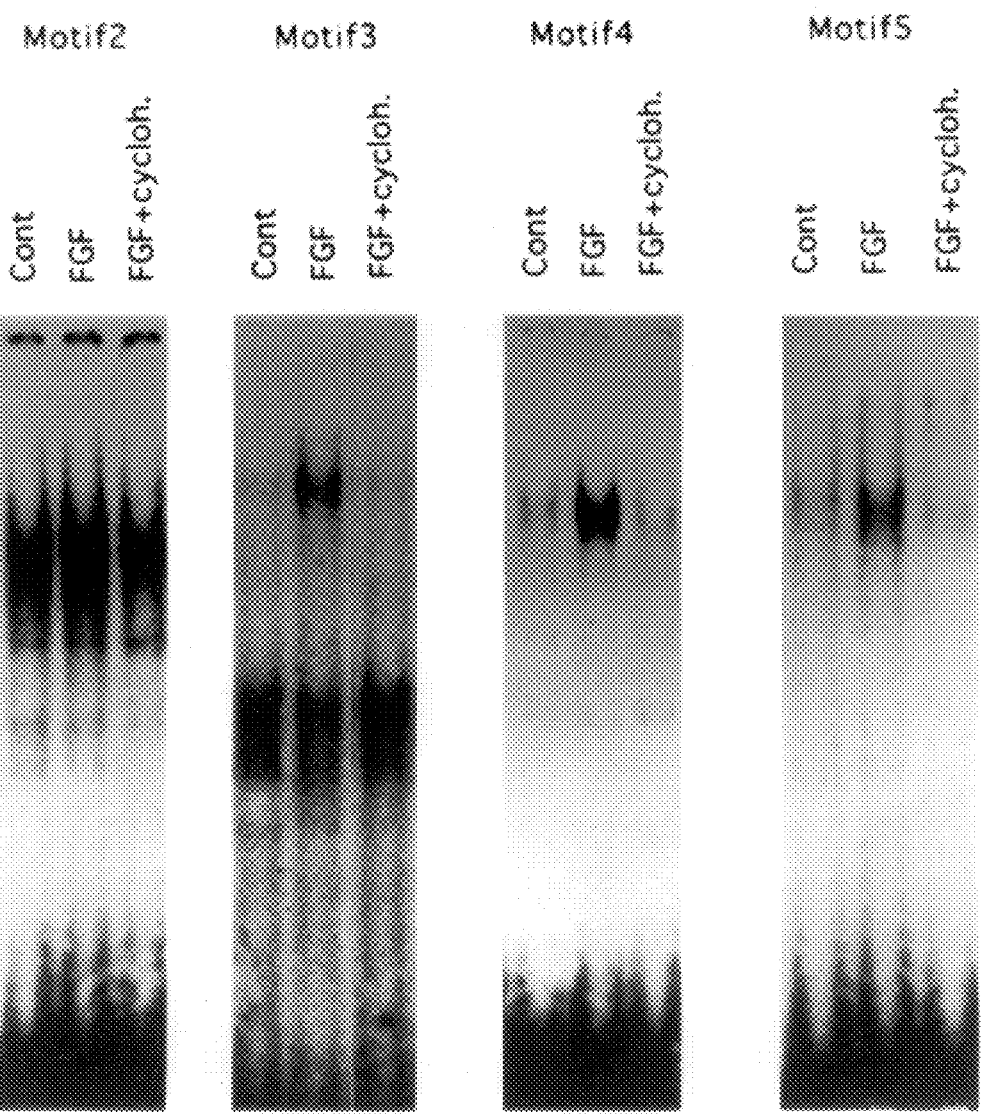
FIG. 22a–d.
Figure 23:
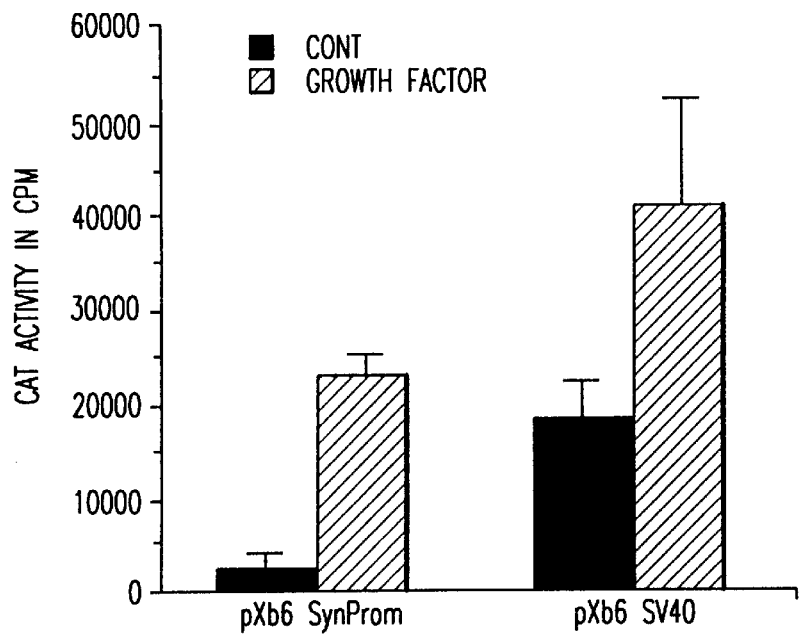
FIG. 23.

To determine whether the different inducible components of FiRE are due to direct post-translational modifications or whether they are newly synthesized, simultaneous cycloheximide and FGF treatment and subsequent protein extraction were performed. As shown in FIG. 22, the FGF-induced binding of AP-1s to motifs 4 and 5 as well as the binding of FIN-1 to motif 3 was blocked by cycloheximide. This indicates that all inducible proteins involved in FiRE require de novo protein synthesis, and that FiRE represents a secondary response element in FGF initiated signalling.

EXAMPLE XIV

Characterization of FiRE Binding Nuclear Proteins. The nucleotide sequences of FiRE (FIG. 13B) was compared to known sequences of different transcription factors stored in the Transcription Factor Database (TFD Sites) (Nisse). Motif 2 showed significant homology to a known transcription factor binding consensus site: an E-box. Motif 4 contained an AP-1-like consensus binding site with one mismatch, and motif 5 has two AP-1-like consensus sites. Motifs 1 and 3 do not contain known consensus sequences for transcription factors.

Various commercial consensus oligonucleotides, including AP-1, AP-2, AP-3, Ets, GATA, SIE, CRE, MEF-1, MEF-2, Max-Myc, AP-1, NFkB, and cEBP were used to test for competition with the nuclear factor-enhanced binding in order to reveal possible protein binding outside the established consensus sequence. The result of this experiment is reported in FIG. 15. A Max-Myc consensus oligonucleotide was able to abolish binding of nuclear factors to motif 2. (FIG. 15D). AP-1 consensus oligos were able to compete binding of nuclear factors to motifs 4 and 5. (FIGS. 15A and 15B). Binding of nuclear factors to motif 3 were unexpectedly abolished by an AP-2 oligonucleotide even though there is no AP-2 consensus site on motif 3. (FIG. 15C). Binding of nuclear factors to motif 1 could not be competed with any of the consensus oligonucleotides tested. These results indicate that motifs 4 and 5 bind an AP-1 complex, motif 3 binds an AP-2 complex, motif 2 binds a basic helix-loop-helix (bHLH) factor such as myc/mad, and motif 1 binds an unknown nuclear factor.

In order to further confirm the results obtained from the competition experiments, the effect of adding specific antibodies to the gel retardation reactions was tested. Antibodies to c-fos and c-jun were able to remove specific binding to motifs 4 and 5 and to produce supershifts. Anti-USF or anti-ATF-3 antibodies analyzed at the same time, had no effect. Thus, the nuclear factors that bind to motifs 4 and 5 are AP-1 fos and jun proteins.

The effect of an AP-2 on binding to motif 3 was tested. While the AP-2 consensus oligonucleotide was able to abolish binding to motif 3, the AP-2 antibody had no effect (FIG. 15C). The ability of this antibody to bind antigen was tested with labeled AP-2 oligonucleotide using FGF-2 induced 3T3 cell nuclear extracts. It produced a supershift, showing that it was finctional. Thus, the protein that binds motif 3 is an AP-2 related transcription factor, which is distinct from AP-2. This protein has been named FIN-1 for FGF inducible nuclear factor.

For motif 2, neither factor Max nor Myc antibodies had obliterating or supershifting effects. However, another bHLH protein, USF, is known to be constitutively expressed in 3T3 cells (Millerberger et al., *Cell Biol.* 5(5):2527–2535 (1995)). USF was shown to occupy motif 2 on USF antibody removed the bond specific for binding to this motif without affecting the binding to other motifs (FIG. 15D).

EXAMPLE XV

Mass Analysis of the Enhancer Binding Nuclear Factors. A gel retardation experiment as described in Example XII was carried out, and the gel containing the oligonucleotides bound to proteins was exposed to UV light to crosslink the protein to the oligonucleotide. Specifically, the gel mobility assays were run as described supra. After the gel was run, it was exposed to 245 nm UV-light (3600J/em$^2$) in a Strategene crosslinker. The gel was exposed for several hours, the specific bands were cut out, eluted overnight at 4° C., precipitated with ethanol, resuspended in Laemmli buffer, denatured at 95° C. for 5 minutes, and loaded onto a 10% SDS-PAGE together with a $^{14}$C-labeled molecular weight markers to analyze their molecular weights. The SDS-PAGE gel is shown in FIG. 15C, with the position of the molecular weight markers shown at the left. Lanes 1–5 correspond to motifs 1–5, respectively. The molecular weights of the nuclear factors were estimated after subtracting the mass of the oligonucleotide from the complex mass as indicated below:

| Motif | MW Oligo + Factor (FIG. 17) | MW Oligo | MW Factor |
|---|---|---|---|
| 1 | 66 kDa | 20 kDa | 46 kDa |
| 3 | 62 kDa; 90 kDa | 12 kDa | 50 kDa; 78 kDa |

This experiment shows a reproducible 46 kDa band for motif 1 and two bands, 78 kDa and 50 kDa, for motif 3. These values have a margin of error of about ±3 kDa.

EXAMPLE XVI

The Enhancer is Not Functional in 3T3 Cells Expressing High Levels ofSyndecan-1. Syndecan-1 transfected 3T3 cells (3T3 1.5) and wild type 3T3 cells were transiently transfected with the pFiRE construct, treated with FGF or a negative control, and analyzed for reporter gene (CAT) expression. The results are depicted in FIG. 16. The closed columns indicate relative CAT activity in control cells (without FGF treatment) while the labeled columns depict relative CAT activity in FGF-treated cells. The results indicate that activation of CAT expression by FGF-2 is significantly reduced in 3T3 1.5 cells which express high levels of syndecan.

EXAMPLE XVII

Targeting a Reporter Gene (lacZ) to Healing Wounds of Mouse Skin Using the FiRE Enhancer. To demonstrate the utility of the FiRE enhancer in targeting a desired gene product to sites of healing wounds, transgenic mice harboring the enhancer operably linked to the syndecan-1 proximal promoter and a reporter gene (lacZ) were produced. Two separate plasmid constructs were made. The first construct contained a 2.25 kb (XhoI-StuI fragment) of the syndecan-1 basic promoter region linked to β-galactosidase reporter gene (pTRG Syn Prom). This plasmid is depicted in FIG. 17. The second plasmid also contained an additional 280 bp (PstI-StyI fragment) encoding the enhancer element operably linked to the basic syndecan promoter (pTRG ENH). This plasmid is depicted in FIG. 18. Constructs were released from vector sequences by Not digestion; separated in agarose gels, and electroeluted. The constructs were then dissolved in injection buffer (10 mM Tris-HCl, pH 7.5 and 0.2 mM EDTA) dialyzed extensively for 3 days against the same buffer and the concentration was adjusted to 2 µg/l.

Transgenic mice were generated by microinjecting (C57B1/6*DBA/2) fertilized eggs using standard methods (Hogan et al., supra). Founder animals were identified based on PCR analysis of tail DNA (Honley and Merle, *Biotechniques* 10:56 (1991)). Transgenic mouse lines were generated by mating founder animals to (C57B1/6*DBA/2) F1 males or females.

The Syn Prom insert resulted in 6 DNA positive and the ENH insert in 12 positive founder animals. DNA positive offspring were produced for further analysis. This analysis was targeted to wounded skin, where syndecan-1 expression is unregulated. Wounds were made to the mice tails and the wounded tissue was cut off 2 days later and stained with X-Gal. All 7 mice with the Syn Prom construct, without FiRE, showed no positive staining. However, all of the 12 FiRE containing mice were found to have staining at the wound sites. See FIG. 22. The intact skin did not show specific staining for either Syn Prom or FiRE. The most intense staining was seen in the wound edge keratinocytes. Further away from the incision site the staining rapidly faded. The staining was first seen at the edge of the incision site on the sheet of keratinocytes starting migration toward the bottom of the wound. The leading edge of the migratory keratinocytes was also heavily stained closer to the end of the incision. Where the keratinocytes that had reached the bottom under the clot were stratifying, the staining was still robust. In the keratinocytes surrounding the hair follicles close to the wound, which are putative cells for a migration start point, revealed strong staining. This portion of staining corresponds with the proposed target cells of FGF-2 and/or FGF-7. However, FGF-7 is a stronger inducer of migration of keratinocytes and is the more probable inducer of FiRE in those cells. The pattern is superimposable with the syndecan-1 expression pattern. For example, in situ hybridization and antibody staining detect proliferating and migrating keratinocytes in stratifying epithelium as well as hair follicle keratinocytes close to the wound site. (Elenius et al. *J. Biol. Chem.* 267: 6435–6441 (1992)). This example can be extrapolated to other gene products, which have replaced the lacZ-gene to target expression of these genes to wound sites as a therapeutic means.

FiRE is Induced Selectively by FGF-7 in Keratinocytes. The ability of FiRE to enhance transcription was tested in the mouse keratinocyte cell line MCA3D (Kuliz-Martin et al., *Carcinogenesis* 4:1367–1377 (1983)). MCA3D cells were transfected as described supra for mouse NIH3T3 cells. Following transfection, the cells were treated with fetal calf serum, PDGF, FGF-1, FGF-2, and FGF-7 as described supra for the NIH3T3 cells. Surprisingly, FGF-2 only slightly activated FiRE although it stimulated cell proliferation. Serum, PDGF, and FGF-1 did not activate FiRE. However, FGF-7 strongly activated FiRE in these cells. Moreover, syndecan-1 mRNA expression is strongly induced by FGF-7. This shows that FiRE can be selectively activated by different members of the FGF family in different cell types.

The Syn Prom construct showed no activation with any growth factors when transfected into MCA3D mouse keratinocytes. In another epithelial cell line derived from mouse mammary gland epithelium (NMuMg), which is negative for FGFRs, none of the tested growth factors had an effect on the FiRE construct. This indicates that FiRE is both cell specific and activated through FGFRs.

EXAMPLE XVIII

Figure 24:
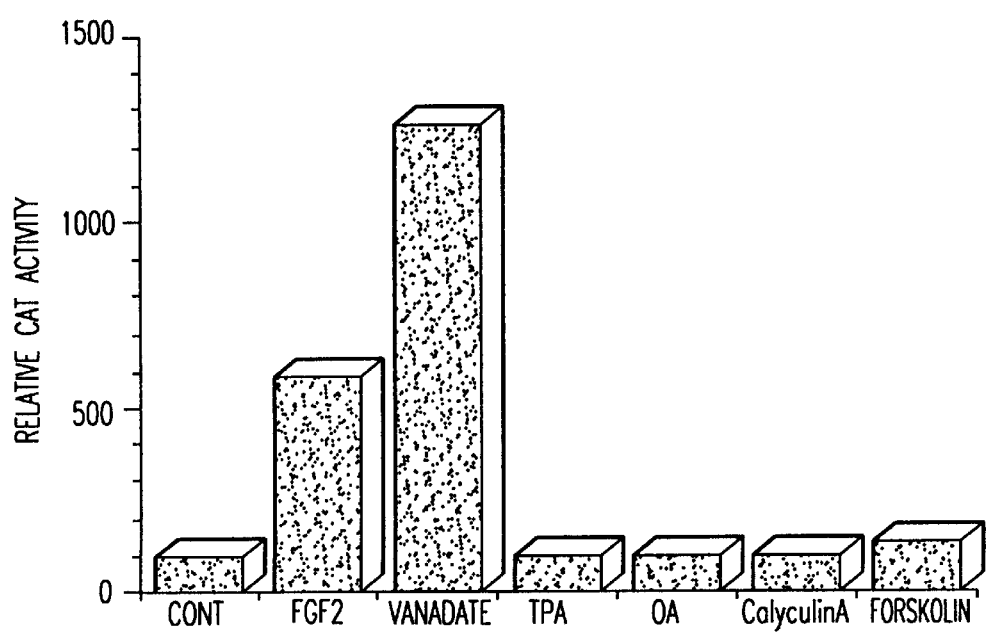
FIG. 24.

Agents Activating AP-1 Are Not Sufficient for FiRE Activation. Since FIRE contains AP-1 transcription factors, whose activation is well characterized, we tested chemicals known to cause AP-1 dependent gene activation. These included the protein kinase C (PKC) activator 12-O-tetradecanoylphorpol-13-acetate (TPA), protein-phosphate −1 and −2 inhibitors okadaic acid and calyculin A, cAMP activator forskolin and tyrosine kinase phosphatase inhibitor orthovanadate (FIG. 24A). Inhibition of the tyrosine kinase phosphatase, causing continuous activation of tyrosine kinases, resulted in activation of FiRE. This suggests, that all the nuclear factors bound to FiRE could be activated by tyrosine kinase activation. Surprisingly however, none of the other compounds known to induce immediate early genes fos and jun and AP-1 driven promoters, were able to activate FiRE. This suggests that more than simple activation of the pathways elicited by these agents, e.g., PKC or cAMP dependent pathways, is required for the response on FiRE, induced by FGF.

All documents, e.g., scientific articles, cited herein are fully incorporated herein by reference. The contents of U.S. application Ser. No. 08/206,186, filed Mar. 7, 1994 and of U.S. application Ser. No. 07/988,247, filed Dec. 1, 1992 are expressly incorporated herein by reference. Having now fully described the invention, it will be understood by those with skill in the art that the scope may be performed within a wide and equivalent range of conditions, parameters and the like, without affecting the spirit or scope of the invention or any embodiment thereof.

What is claimed is:

1. A purified DNA molecule comprising an enhancer element, wherein said enhancer element comprises the sequence of SEQ ID No.5:

1 TGCAGATAGT CTCTCATCTT GGTGCCCTTC CCACAGAGGC TGGGGCGGCA

51 GGAGGGAGCC TGGACAGCTC AGACACTGGG TCATTGATGA CTGTTGTGTG

101 GGATACCTGC CGGGGCGCAG GAGTGAGCCA TGCCACCCCA GGAAGTGGTT

151 CAGGGTGACT CTTCTTGGCA CACCTGGGAG GATGTAGCTG GTGCTGGCAC

201 ACCCACCGTC ACGAGAGCTT CCTGTCCAAA CCTTCAACAA AGGCGGCTTC

251 TTGAGACAGG CTAGACTGAA GTCACCAGCC TTG.

2. The purified DNA molecule of claim 1, wherein said enhancer element consists of said sequence of SEQ ID No.5.

3. A purified DNA molecule comprising an enhancer element, wherein said enhancer element comprises each of the following sequences:
   (a) TGGCACACCCACCGTCACGAGAGCT (SEQ ID No. 11);
   (b) TGGCACACCTGGGAG (SEQ ID No. 12);
   (c) TGGTTCAGGGTGACT (SEQ ID No. 13);
   (d) AGGAGTGAGCCATGCCACC (SEQ ID No. 9); and
   (e) CTGGGTCATTGATGACTG (SEQ ID No. 10).

4. A purified DNA molecule comprising an enhancer element, wherein said enhancer element comprises each of the following sequences:

(a) TGGCACACCCACCGTCACGAGAGCT (SEQ ID No. 11);
   (b) TGGTTCAGGGTGACT (SEQ ID No. 13);
   (c) AGGAGTGAGCCATGCCACC (SEQ ID No. 9); and
   (d) CTGGGTCATTGATGACTG (SEQ ID No. 10).

5. The purified DNA molecule of any one of claims 1–4, wherein said DNA molecule further comprises a promoter operably linked to said enhancer element.

6. The purified DNA molecule of claim 5, wherein said DNA molecule further comprises the coding sequence of a heterologous gene operably linked to said promoter.

7. The purified DNA molecule of claim 5, wherein said promoter is not the syndecan promoter.

8. The purified DNA molecule of claim 5, wherein said promoter is the SV40 promoter.

9. A method of making a DNA molecule that is capable of expressing a heterologous gene, wherein said method comprises:
   a) providing the purified DNA of any one of claims 1–4, and
   b) operably linking said enhancer element to a promoter and to the coding sequence of said gene.

10. A purified DNA molecule comprising a sequence selected from the group consisting of:
   (a) TGGCACACCCACCGTCACGAGAGCT (SEQ ID No. 11);
   (b) TGGCACACCTGGGAG (SEQ ID No. 12);
   (c) AGGAGTGAGCCATGCCACC (SEQ ID No. 9);
   (d) CTGGGTCATTGATGACTG (SEQ ID No. 10) and
   (e) TGGTTCAGGGTGACT (SEQ ID No. 13).

11. The purified DNA molecule of claim 10, wherein said sequence is said (a): TGGCACACCCACCGTCACGAGAGCT (SEQ ID No. 11).

12. The purified DNA molecule of claim 10, wherein said sequence is said (b): TGGCACACCTGGGAG (SEQ ID No. 12).

13. The purified DNA molecule of claim 10, wherein said sequence is said (c): AGGAGTGAGCCATGCCACC (SEQ ID No. 9).

14. The purified DNA molecule of claim 10, wherein said sequence is said (d): CTGGGTCATTGATGACTG (SEQ ID No. 10).

15. The purified DNA molecule of claim 10, wherein said molecule is said (e) TGGTTCAGGGTGACT (SEQ ID No. 13).

16. The purified DNA of claim 15, wherein said DNA molecule further comprises a promoter operably linked to said molecule.

17. The purified DNA of claim 16, wherein said DNA molecule further comprises a structural heterologous gene operably linked to said promoter.

18. The purified DNA of claim 16, wherein said promoter is not the syndecan promoter.

19. The purified DNA of claim 16, wherein said promoter is the SV40 promoter.

20. A recombinant vector, wherein said vector comprises a DNA enhancer element, wherein said enhancer element comprises the sequence of SEQ ID No.5:

```
  1 TGCAGATAGT CTCTCATCTT GGTGCCCTTC
    CCACAGAGGC TGGGGCGGCA
 51 GGAGGGAGCC TGGACAGCTC AGACACTGGG
    TCATTGATGA CTGTTGTGTG
101 GGATACCTGC CGGGGCGCAG GAGTGAGCCA
    TGCCACCCCA GGAAGTGGTT
151 CAGGGTGACT CTTCTTGGCA CACCTGGGAG
    GATGTAGCTG GTGCTGGCAC
201 ACCCACCGTC ACGAGAGCTT CCTGTCCAAA
    CCTTCAACAA AGGCGGCTTC
251 TTGAGACAGG CTAGACTGAA GTCACCAGCC
    TTG.
```

21. The recombinant vector of claim 20, wherein said enhancer element consists of said sequence of SEQ ID No.5.

22. A recombinant vector comprising a DNA enhancer element, wherein said enchancer element comprises each of the following sequences:

(a) TGGCACACCCACCGTCACGAGAGCT (SEQ ID No. 11);

(b) TGGCACACCTGGGAG (SEQ ID No. 12);

(c) TGGTTCAGGGTGACT (SEQ ID No. 13);

(d) AGGAGTGAGCCATGCCACC (SEQ ID No. 9); and (e) CTGGGTCATTGATGACTG (SEQ ID No. 10).

23. A recombinant vector comprising a DNA enhancer element, wherein said enhancer element comprises each of the following sequences:

(a) TGGCACACCCACCGTCACGAGAGCT (SEQ ID No. 11);

(b) TGGTTCAGGGTGACT (SEQ ID No. 13);

(c) AGGAGTGAGCCATGCCACC (SEQ ID No. 9); and (d) CTGGGTCATTGATGACTG (SEQ ID No. 10).

24. A recombinant vector comprising a DNA sequence selected from the group consisting of:

(a) TGGCACACCCACCGTCACGAGAGCT (SEQ ID No. 11);

(b) TGGCACACCTGGGAG (SEQ ID No. 12);

(c) AGGAGTGAGCCATGCCACC (SEQ ID No. 9);

(d) CTGGGTCATTGATGACTG (SEQ ID No. 10) and (e) TGGTTCAGGGTGACT (SEQ ID No. 13).

25. The recombinant vector of claim 24, wherein said sequence is said (a): TGGCACACCCACCGTCACGAGAGCT (SEQ ID No. 11).

26. The recombinant vector of claim 24, wherein said sequence is said (b) TGGCACACCTGGGAG (SEQ ID No. 12).

27. The recombinant vector of claim 25, wherein said sequence is said (c) AGGAGTGAGCCATGCCACC (SEQ ID No. 9).

28. The recombinant vector of claim 24, wherein said sequence is said (d) CTGGGTCATTGATGACTG (SEQ ID No. 10).

29. A recombinant host cell containing said recombinant vector of any one of claims 20–28.

30. The recombinant vector of claim 24, wherein said sequence is said (e) TGGTTCAGGGTGACT (SEQ ID No. 13).

31. A recombinant host cell containing said recombinant vector of claim 30.

32. The recombinant vector of any one of claims 20–23, wherein said DNA molecule further comprises a promoter operably linked to said enhancer element.

33. The recombinant vector of claim 32, wherein said promoter is not the syndecan promoter.

34. The recombinant vector of claim 32, wherein said promoter is the SV40 promoter.

35. A recombinant host cell containing said recombinant vector of claim 32.

36. The recombinant vector of claim 32, wherein said DNA molecule further comprises the coding sequence of a heterologous gene operably linked to said promoter.

37. A recombinant host cell containing said recombinant vector of claim 33.

38. A recombinant host cell containing said recombinant vector of claim 34.

39. A recombinant host cell containing said recombinant vector of claim 36.

40. A method for the enhancement of the expression of a gene, said method comprising
a) culturing the recombinant host cell of claim 39;
b) activating said enhancer element; and
c) enhancing expression of said gene as a result of part (b).

41. The method of claim 40, wherein said enhancer element is activated by FIN-1 binding.

42. The method of claim 40, wherein said host cell is a mesenchymal cell.

43. The method of claim 40, wherein said host cell is a keratinocyte.

44. The method of claim 40, wherein said enhancer element is activated by a FGF.

45. The method of claim 44, wherein said FGF is FGF-2.

46. The method of claim 44, wherein said FGF is FGF-7.

* * * * *

UNITED STATES PATENT AND TRADEMARK OFFICE
CERTIFICATE OF CORRECTION

PATENT NO. : 6,017,727
DATED : January 25, 2000
INVENTOR(S) : Jalkanen et al.

Figure 3:
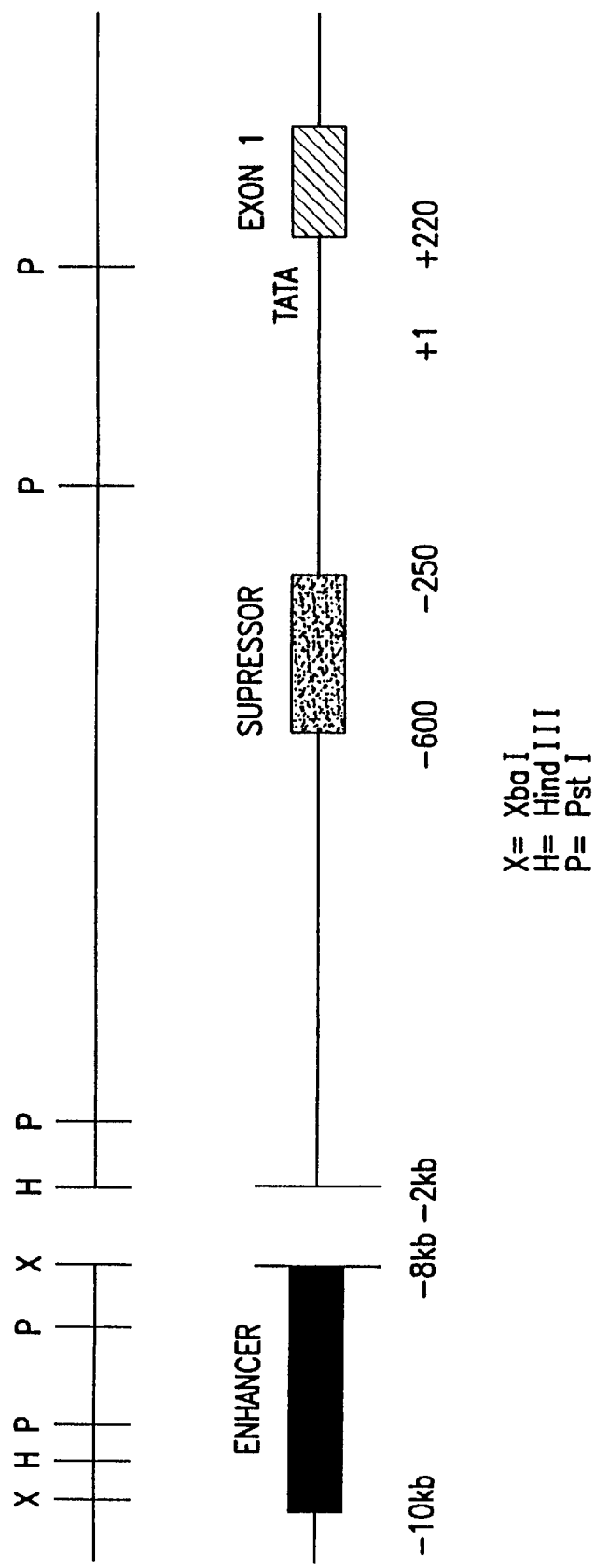

It is certified that error appears in the above-identified patent and that said Letters Patent is hereby corrected as shown below:

Drawings,
Sheet containing Figure 3, please delete the term "SUPRESSOR" and replace with -- SUPPRESSOR --.
Sheet containing Figures 5a-5d, please delete the term "FIG. 5d" and replace with -- FIG. 5b -- and delete the term "FIG. 5b" and replace with -- FIG. 5d --.
Sheet containing Figures 9a and 9b, please delete the current Figure 9b:

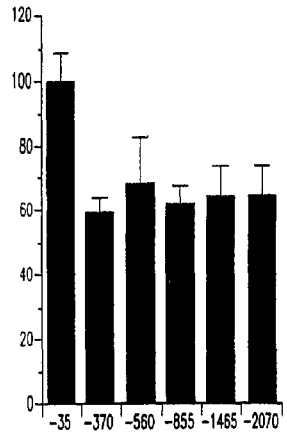

FIG.9b

UNITED STATES PATENT AND TRADEMARK OFFICE
CERTIFICATE OF CORRECTION

PATENT NO. : 6,017,727
DATED : January 25, 2000
INVENTOR(S) : Jalkanen et al.

Figure 9B:
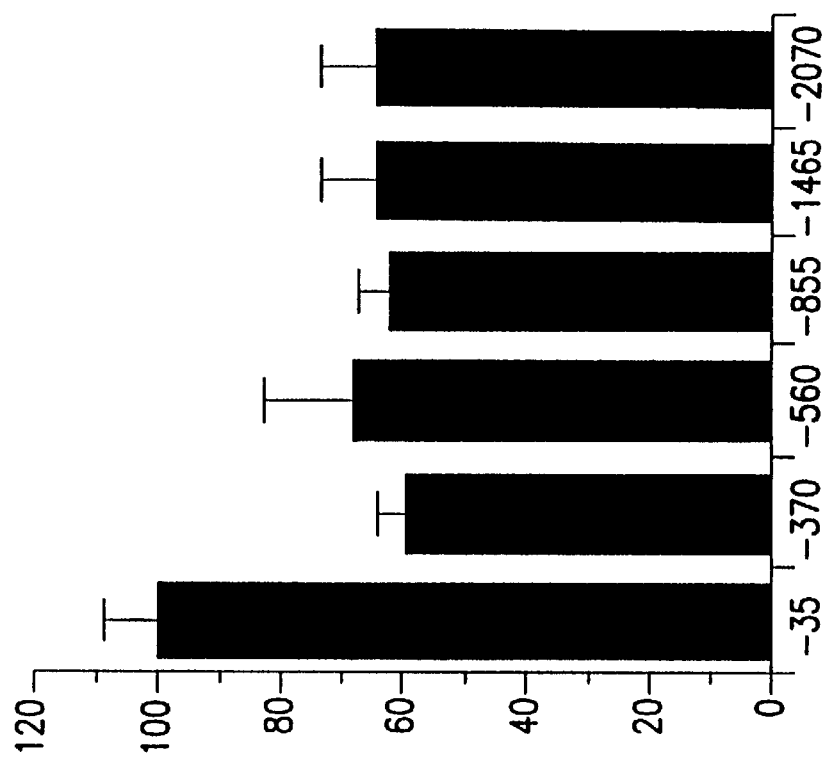
FIGS. 9A and 9B.
Figure 9A:
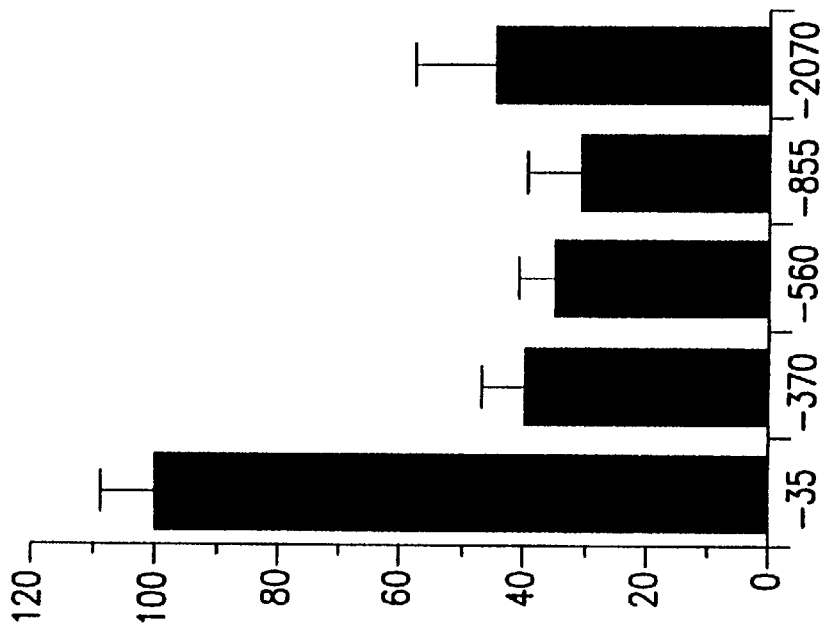

It is certified that error appears in the above-identified patent and that said Letters Patent is hereby corrected as shown below:

and replace with the corrected Figure 9b:

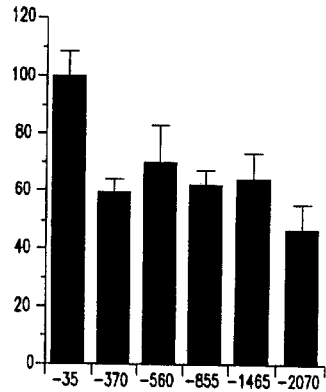

FIG.9b

Signed and Sealed this

Twelfth Day of November, 2002

*Attest:*

*Attesting Officer*

JAMES E. ROGAN
*Director of the United States Patent and Trademark Office*